United States Patent [19]

Chakravarty et al.

[11] Patent Number: 5,162,325
[45] Date of Patent: Nov. 10, 1992

[54] ANGIOTENSIN II ANTAGONISTS INCORPORATING A SUBSTITUTED BENZYL ELEMENT

[75] Inventors: Prasun K. Chakravarty, Edison; Malcolm MacCoss, Freehold; Nathan Mantlo; Thomas F. Walsh, both of Westfield, all of N.J.

[73] Assignee: Merck & Co., Inc., Rahway, N.J.

[21] Appl. No.: 697,169

[22] Filed: May 7, 1991

[51] Int. Cl.$^5$ ............... A61K 31/505; C07D 401/10; C07D 401/12; C07D 279/04
[52] U.S. Cl. ........................ 514/259; 514/80; 514/86; 514/222.2; 514/226.5; 514/226.8; 514/227.8; 514/228.2; 514/228.8; 514/232.2; 252/232.5; 252/235.8; 252/236.5; 252/253; 252/269; 252/274; 544/3; 544/54; 544/55; 544/57; 544/58.6; 544/60; 544/62; 544/63; 544/80; 544/82; 544/96; 544/116
[58] Field of Search ............... 544/244, 284, 290, 333, 544/295, 296, 54, 55, 57, 62, 116, 243; 514/232.2, 253, 269, 274

[56] References Cited

FOREIGN PATENT DOCUMENTS 0411766 2/1991 European Pat. Off. .

Primary Examiner—Mukund J. Shah
Assistant Examiner—Y. N. Gupta
Attorney, Agent, or Firm—Valerie J. Camara; William H. Nicholson; Joseph F. DiPrima

[57] ABSTRACT

Substituted heterocycles attached through a methylene bridge to novel substituted phenyl derivatives of the Formula I are useful as angiotensin II antagonists.

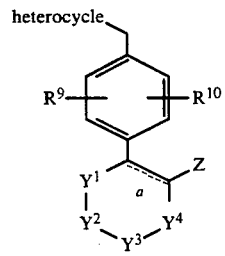

13 Claims, No Drawings

ANGIOTENSIN II ANTAGONISTS INCORPORATING A SUBSTITUTED BENZYL ELEMENT

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804 and in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed within this application or in any U.S. Patent, European Applications or literature publication are of the type containing substituted heterocycles bonded through an alkyl bridge to a novel substituted phenyl of the type disclosed herein. The quinazolin4(1H)-ones, triazolinones, triazolinimines, and pyrimidinones have been disclosed in earlier U.S. Patent applications focusing on the heterocyclic fragment of the antagonist design. The Ser. Nos. of these applications are 351,508; 358,971; 375,655; 360,673; 375,217; and 386,328 and are hereby incorporated by reference.

BRIEF DESCRIPTION OF THE INVENTION

This invention is directed to substituted heterocycles attached through a methylene bridge to novel substituted phenyl derivatives to give compounds of the Formula I, which are angiotensin II antagonists and are useful in the treatment of hypertension and congestive heart failure. The compounds of the invention are useful as ocular antihypertensives.

Specifically, the compounds of this invention contain a heterocyclic moiety which is substituted at the specified positions and to which a methylene bridge connecting a novel substituted phenyl group as defined by the lower portion of Formula I, is attached. Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of the general Formula I:

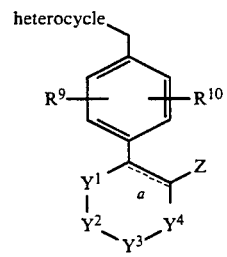

wherein the heterocycle is defined as:

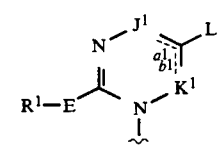

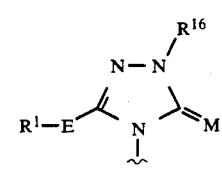

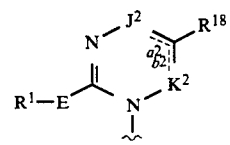

$R^1$ is:
   (a) $(C_1-C_6)$-alkyl, $(C_2-C_6)$-alkenyl or $(C_2-C_6)$-alkynyl each of which is unsubstituted or substituted with a substituent selected from the group consisting of:
      i) aryl as defined below,
      ii) $(C_3-C_7)$-cycloalkyl,
      iii) Cl, Br, I, F,
      iv) OH,
      v) $NH_2$,
      vi) $NH(C_1-C_4)$-alkyl,
      vii) $N[(C_1-C_4)\text{-alkyl}]_2$,
      viii) $NHSO_2R^2$,
      ix) $CF_3$,
      x) $COOR^2$, or
      xi) $SO_2NHR^2$;
   (b) aryl, wherein aryl is defined as phenyl or naphthyl unsubstituted or substituted with 1 or 2 substituents selected from the group consisting of:
      i) Br, I, Cl, F,
      ii) $(C_1-C_4)$-alkyl,
      iii) $(C_1-C_4)$-alkoxy,
      iv) $NO_2$,
      v) $CF_3$,
      vi) $SO_2NR^2R^2$,
      vii) $(C_1-C_4)$-alkylthio,
      viii) hydroxy,
      ix) amino,
      x) $(C_3-C_7)$-cycloalkyl,
      xi) $(C_3-C_{10})$-alkenyl,
      xii) $CO_2H$, or
      xiii) $CO_2-(C_1-C_4)$-alkyl;
   (c) heteroaryl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
      i) Cl, Br, I, or F,
      ii) OH,
      iii) SH,
      iv) $NO_2$,
      v) $(C_1-C_4)$-alkyl,
      vi) $(C_2-C_4)$-alkenyl,
      vii) $(C_2-C_4)$-alkynyl,
      viii) $(C_1-C_4)$-alkoxy,
      ix) $CF_3$,
      x) $CO_2-(C_1-C_4)$-alkyl,
      xi) $NH_2$,
      xii) $NH[(C_1-C_4)\text{-alkyl}]$, or
      xiii) $N[(C_1-C_4)\text{-alkyl}]_2$, or
   (d) perfluoro-$(C_1-C_4)$-alkyl;
E is:
   (a) a single bond,
   (b) $-S(O)_n(CH_2)_s-$, or
   (c) $-O-$;
n is 0 to 2;
s is 0 to 5;
$J^1$ is (a) $-C(=M)-$, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{7b}$, $R^{8a}$ and $R^{8b}$;
(a) $-C(=M)-$, (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a 6-membered aromatic ring containing one nitrogen atom, substituted on the carbon atoms with $R^{7a}$, $R^{7b}$ and $R^{8b}$;
one of $a^1$ or $b^1$ is a double bond in structures Ia provided that when $J^1$ is $-C(=M)-$ then $b^1$ is a double bond and when $K^1$ is $-C(=M)-$ then $a^1$ is a double bond;
$J^2$ is (a) $-C(=M)-$, or (b) $-C(R^{17})-$;
$K^2$ is (a) $-C(=M)-$, or (b) $-C(R^{17})-$, provided that one and only one of $J^2$ and $K^2$ is $-C(=M)-$;
one of $a^2$ or $b^2$ is a double bond in structure Ic provided that when $J^2$ is $-C(=M)-$ then $b^2$ is a double bond and when $K^2$ is $-C(=M)-$ then $a^2$ is a double bond;
M is O, S or $NR^{15}$;
$R^2$ is:
   (a) H,
   (b) $(C_1-C_6)$-alkyl,
   (c) $-CH_2-O-C(O)CH_3$,
   (d) $CH_2$-aryl, or
   (e) aryl;
$R^{7a}$ and $R^{7b}$ are independently
   (a) H,
   (b) $(C_1-C_6)$-alkyl, $(C_2-C_6)$-alkenyl or $(C_2-C_6)$-alkynyl,
   (c) Cl, Br, I, F,
   (d) $CF_3$, or
   (e) when $R^{7a}$ and $R^{7b}$ are bonded to adjacent carbon atoms, they can be joined to form a phenyl or naphthyl ring;
$R^{8a}$ and $R^{8b}$ are independently
   (a) H,
   (b) aryl-$(C_1-C_4)$-alkyl,
   (c) heteroaryl-$(C_1-C_4)$-alkyl,
   (d) $(C_1-C_6)$-alkyl, which is unsubstituted or substituted with a substituent selected from the group consisting of: $-CON(R^2)_2$, -heteroaryl, $-S(O)_x-R^{21}$, -tetrazol-5-yl, $-CONHSO_2R^{21}$, $-SO_2NH$-heteroaryl, $-SO_2NHCOR^{21}$, $-PO(OR^2)_2$, $-PO(OR^2)_2$, $-SO_2NH-CN$, $-NR^2COOR^{21}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^2$, $-CONHR^2$, $-O-COR^2$, or phenyl or naphthyl,
   (e) $-CO$-aryl,
   (f) $(C_3-C_7)$-cycloalkyl,
   (g) Cl, Br, I, F,
   (h) $-OH$,
   (i) $-OR^{21}$,
   (j) $-SH$,
   (k) $-S(O)_n-(C_1-C_4)$-alkyl,
   (l) $-COR^2$,
   (m) $-CO_2H$,
   (n) $-CO_2-(C_1-C_4)$-alkyl,
   (o) $-SO_3H$,
   (p) $-NR^2R^{21}$,
   (q) $-NR^2COR^{21}$,
   (r) $-NR^2COOR^{21}$,
   (s) $-SO_2NHR^2$,
   (t) $-SO_2NR^2R^2$,
   (u) $-NO_2$,
   (v) $-NHSO_2CF_3$,
   (w) $-CONR^2R^2$,
   (x) $-(C_1-C_4)$-perfluoroalkyl,
   (y) $-COOR^2$,
   (z) $-SO_3H$,
   (aa) $-N(R^2)SO_2R^{21}$,
   (bb) $-NR^2CONR^4R^{21}$,
   (cc) $-OC(=O)NR^{21}R^2$,
   (dd) -aryl, (ee) —NHSO$_2$CF$_3$,
(ff) —SO$_2$NH-heteroaryl,
(gg) —SO$_2$NHCOR$^{21}$,
(hh) —CONHSO$_2$R$^{21}$,
(ii) —PO(OR$^2$)$_2$,
(jj) -tetrazol-5-yl,
(kk) —CONH(tetrazol-5-yl),
(ll) —SO$_2$NHCN, or
(mm) -heteroaryl;

—Y$^1$—Y$^2$—Y$^3$—Y$^4$— is:
(a) —N—CR$^{11}$—CR$^{11}$=CR$^{11}$—,
(b) —CR$^{11}$=N—CR$^{11}$=CR$^{11}$—,
(c) —CR$^{11}$=CR$^{11}$—N=CR$^{11}$—,
(d) —CR$^{11}$=CR$^{11}$—CR$^{11}$=N—,
(e) —N=CR$^{11}$—N=CR$^{11}$—,
(f) —CR$^{11}$=N—CR$^{11}$=N—,
(g) —N=N—CR$^{11}$=CR$^{11}$—,
(h) —CR$^{11}$=N—N=CR$^{11}$—,
(i) —CR$^{11}$=CR$^{11}$—N=N—,
(j) —N=CR$^{11}$—CR$^{11}$=N—,

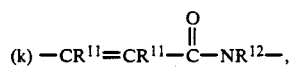

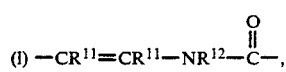

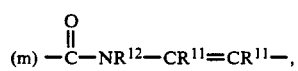

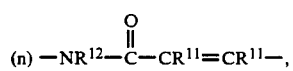

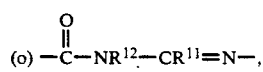

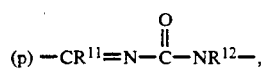

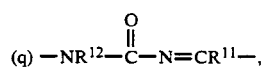

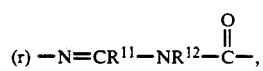

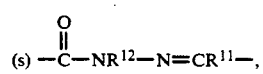

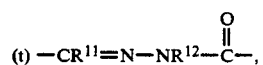

wherein a represents a double bond in each of the above definitions [(a) thru (t)]

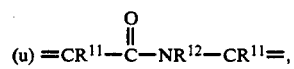

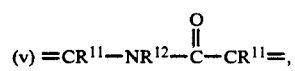

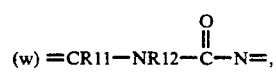

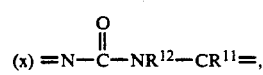

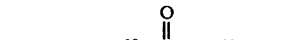

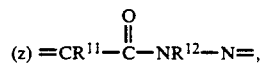

wherein a represents a single bond in each of the above definitions [(u) thru (z)];

R$^9$ and R$^{10}$ are each independently:
(a) H,
(b) Cl, Br, I, F,
(c) NO$_2$,
(d) (C$_1$–C$_6$)-alkyl,
(e) (C$_1$–C$_6$)-acyloxy,
(f) (C$_3$–C$_6$)-cycloalkyl,
(g) (C$_1$–C$_6$)-alkoxy,
(h) —NHSO$_2$R$^2$,
(i) hydroxy-(C$_1$–C$_4$)-alkyl,
(j) aryl-(C$_1$–C$_4$)-alkyl,
(k) (C$_1$–C$_4$)-alkylthio,
(l) (C$_1$–C$_4$)-alkylsulfinyl,
(m) (C$_1$–C$_4$)-alkylsulfonyl,
(n) NH$_2$,
(o) (C$_1$–C$_4$)-alkylamino,
(p) (C$_1$–C$_4$)-dialkylamino,
(q) CF$_3$,
(r) —SO$_2$NHR$^2$,
(s) furyl,
(t) aryl, or
(u) when R$^9$ and R$^{10}$ are bonded to adjacent carbon atoms, they can be joined to form a phenyl or naphthyl ring;

R$^{11}$ is:
(a) H,
(b) Cl, Br, I, F,
(c) NO$_2$,
(d) NH$_2$,
(e) (C$_1$–C$_4$)-alkylamino,
(f) di-(C$_1$–C$_4$-alkyl)amino
(g) SO$_2$NHR$^2$,
(h) CF$_3$,
(i) (C$_1$–C$_4$)-alkyl,
(j) (C$_1$–C$_4$)-alkoxy, or
(k) when two R$^{11}$ substituents are bonded to adjacent carbon atoms, they can be joined to form a phenyl or naphthyl ring;

R$^{12}$ is:
(a) H,
(b) (C$_1$–C$_4$)-alkyl, or
(c) phenyl or —CH$_2$-phenyl, in which the phenyl is unsubstituted or substituted with one or two substituents selected from the group consisting of: Cl, Br, I, F, (C$_1$–C$_4$)-alkyl, or (C$_1$–C$_4$)-alkoxy, CF$_3$, NH[(C$_1$–C$_4$)-alkyl], N[(C$_1$–C$_4$)-alkyl]$_2$, NH$_2$ or CO$_2$R$^2$;

Z is:
(a) —CO$_2$R$^2$,
(b) —SO$_3$R$^{13}$,
(c) —NHSO$_2$R$^{14}$,
(d) —PO(OR$^{13}$)$_2$,
(e) —SO$_2$NHR$^2$,
(f) —CONHOR$^{13}$,

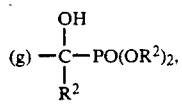
(h) —CN,
(i) —SO$_2$NH—heteroaryl,
(j) —CH$_2$SO$_2$NH—heteroaryl,
(k) —SO$_2$NHC(O)R$^{14}$,
(l) —CH$_2$SO$_2$NHC(O)R$^{14}$,
(m) —C(O)NHSO$_2$R$^{14}$,
(n) —CH$_2$C(O)NHSO$_2$R$^{14}$,
(o) —NHSO$_2$NHC(O)R$^{14}$,
(p) —NHC(O)NHSO$_2$R$^{14}$,

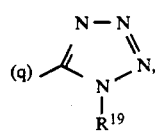

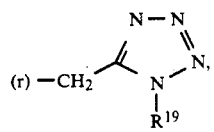

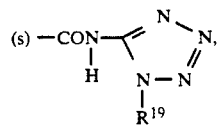

(t) —CONHNHSO$_2$CF$_3$,

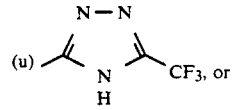

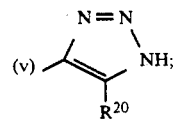

$R^{13}$ is H, —CH$_2$-phenyl or —CH(R$^4$)—O—C(O)R$^4$;
$R^{14}$ is
 (a) aryl,
 (b) heteroaryl,
 (c) (C$_3$-C$_7$)-cycloalkyl,
 (d) (C$_1$-C$_4$)-alkyl, unsubstituted or substituted with a substituent selected from the group consisting of: aryl, heteroaryl, —OH, —SH, (C$_1$-C$_4$)-alkyl, (C$_1$-C$_4$)-alkoxy, (C$_1$-C$_4$)-alkylthio, —CF$_3$, Cl, Br, F, I, —NO$_2$, —CO$_2$H, CO$_2$—(C$_1$-C$_4$)-alkyl, —NH$_2$, —N[(C$_1$-C$_4$)-alkyl]$_2$, —NH[(C$_1$-C$_4$)-alkyl], —PO$_3$H or PO(OH) (C$_1$-C$_4$)-alkyoxy, or
 (e) (C$_1$-C$_4$)-perfluoroalkyl;
$R^{15}$ is
 (a) H,
 (b) aryl;
 (c) (C$_1$-C$_6$)-alkyl, (C$_2$-C$_6$)-alkenyl or (C$_2$-C$_6$)-alkynyl each of which is unsubstituted or substituted with one or more substituents selected from the group consisting of: aryl, (C$_3$-C$_7$)-cycloalkyl, Cl, Br, I, F, —OH, —NH$_2$, —NH[(C$_1$-C$_4$)-alkyl], —N[(C$_1$-C$_4$)-alkyl]$_2$, —NH—SO$_2$R$^2$, —COOR$^2$, —SO$_2$NHR$^2$; or
 (d) heteroaryl;
$R^{16}$ is
 (a) (C$_1$-C$_{10}$)-alkyl;
 (b) substituted (C$_1$-C$_{10}$)-alkyl in which one or two substituent(s) selected from the group consisting of:
  (1) I, Br, Cl, F,
  (2) hydroxy,
  (3) (C$_1$-C$_{10}$)-alkoxy,
  (4) (C$_1$-C$_5$)-alkoxycarbonyl,
  (5) (C$_1$-C$_5$)-acyloxy,
  (6) (C$_3$-C$_8$)-cycloalkyl,
  (7) phenyl, unsubstituted or substituted with V and W,
  (8) naphthyl, unsubstituted or substituted with V and W,
  (9) (C$_1$-C$_{10}$)-alkyl-S(O)$_n$,
  (10) (C$_3$-C$_8$)-cycloalkyl-S(O)$_n$,
  (11) phenyl-S(O)$_n$,
  (12) substituted phenyl-S(O)$_n$, in which the substituents are V and W,
  (13) oxo,
  (14) carboxy,
  (15) NR$^2$R$^2$,
  (16) (C$_1$-C$_5$)alkylaminocarbonyl
 (c) (C$_1$-C$_4$)-perfluoroalkyl
 (d) (C$_2$-C$_{10}$)-alkenyl,
 (e) (C$_2$-C$_{10}$)-alkynyl,
 (f) (C$_3$-C$_8$)-cycloalkyl,
 (g) substituted (C$_3$-C$_8$)-cycloalkyl, in which the substituent is selected from: (C$_1$-C$_5$)-alkyl or (C$_1$-C$_5$)-alkoxy;
 (h) phenyl, unsubstituted or substituted with V and W,
 (i) naphthyl, unsubstituted or substituted with V and W,
 (j) phenyl-(CH$_2$)$_r$—(M$_1$)$_z$—(CH$_2$)$_r$—, in which the phenyl group is unsubstituted or substituted with V and W,
 (k) naphthyl-(CH$_2$)$_r$—(M$_1$)$_z$—(CH$_2$)$_r$—, in which the naphthyl group is unsubstituted or substituted with V and W,

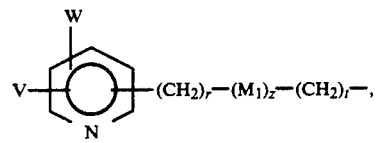

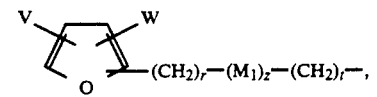

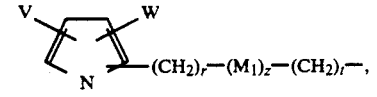

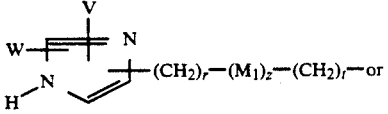

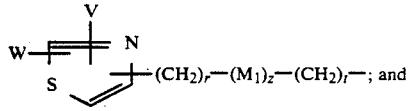

(q) —[($C_1$–$C_4$)-alkyl]$NR^2R^{21}$,
(r) —[($C_1$–$C_4$)-alkyl]$NR^2COR^{21}$,
(s) —[($C_1$–$C_4$)-alkyl]$NR^2COOR^{21}$,
(t) —[($C_1$–$C_4$)-alkyl]$CONR^2R^2$,
(u) —[($C_1$–$C_4$)-alkyl]$N(R^2)SO_2R^{21}$,
(v) —[($C_1$–$C_4$)-alkyl]$NR^2CONR^2R^{21}$, or
(w) —[($C_1$–$C_4$)-alkyl]$OC(=O)NR^{21}R^2$; and V and W are each independently selected from:
(a) H,
(b) ($C_1$–$C_5$)-alkoxy,
(c) ($C_1$–$C_5$)-alkyl,
(d) hydroxy,
(e) ($C_1$–$C_5$)-alkyl-$S(O)_n$,
(f) —CN,
(g) —$NO_2$,
(h) —$NR^2R^2$,
(i) ($C_1$–$C_5$)-acyl-$NR^2R^2$,
(j) —$CO_2R^2$,
(k) ($C_1$–$C_5$)-alkyl-carbonyl,
(l) ($C_1$–$C_5$)-perfluoroalkyl,
(m) I, Br, Cl, F,
(n) hydroxy-($C_1$–$C_4$)-alkyl-,
(o) carboxy-($C_1$–$C_4$)-alkyl-,
(p) -tetrazol-5-yl,
(q) —NH—$SO_2CF_3$, or
(r) aryl;

$M_1$ is M or —C(O)—;
z is 0 or 1;
r and t are 0 to 2;

$R^{17}$ and $R^{18}$ are each independently selected from:
(a) H,
(b) aryl-($C_1$–$C_4$)-alkyl-,
(c) heteroaryl-($C_1$–$C_4$)-alkyl-,
(d) ($C_1$–$C_4$)-alkyl unsubstituted or substituted with a substituent selected from the group consisting of —OH, —$NH_2$, guanidino, ($C_1$–$C_4$)-alkoxy, ($C_1$–$C_4$)-alkylthio, ($C_1$–$C_4$)-alkylamino, ($C_1$–$C_4$)-dialkylamino, —$COOR^2$, —$CONHR^2$, —O—$COR^2$, $CF_3$;
(e) ($C_1$–$C_4$)-alkenyl,
(f) —CO-aryl,
(g) ($C_3$–$C_7$)-cycloalkyl,
(h) Cl, Br, I, F,
(i) —OH,
(j) —O—($C_1$–$C_4$)-alkyl,
(k) —($C_1$–$C_4$)-perfluoroalkyl,
(l) —SH,
(m) —$S(O)_n$—($C_1$–$C_4$)-alkyl,
(n) —CHO,
(o) —$CO_2R^2$,
(p) —$SO_3H$,
(q) —$NH_2$,
(r) —NH[($C_1$–$C_4$)-alkyl],
(s) —N[($C_1$–$C_4$)-alkyl]$_2$,
(t) —$NHCO_2$—($C_1$–$C_4$)-alkyl,
(u) —$SO_2NR^2R^2$,
(v) —$CH_2OCOR^2$
(w) —NH—$SO_2$—($C_1$–$C_4$)-alkyl,
(x) 5 or 6 membered saturated heterocycle containing one nitrogen atom and optionally containing one other heteroatom selected from N, O, or S, such as pyrrolidine, morpholine, or piperazine,
(y) aryl,
(z) heteroaryl,
(aa) tetrazol-5-yl,
(bb) —[($C_1$–$C_4$)-alkyl]$NR^2R^{21}$,
(cc) —[($C_1$–$C_4$)-alkyl]$NR^2COR^{21}$,
(dd) —[($C_1$–$C_4$)-alkyl]$NR^2COOR^{21}$,
(ee) —[($C_1$–$C_4$)-alkyl]$CONR^2R^2$,
(ff) —[($C_1$–$C_4$)-alkyl]$N(R^2)SO_2R^{21}$,
(gg) —[($C_1$–$C_4$)-alkyl]$NR^2CONR^2R^{21}$, or
(hh) —[($C_1$–$C_4$)-alkyl]$OC(=O)NR^{21}R^2$; and $R^{19}$ is:
(a) H,
(b) ($C_1$–$C_6$)-alkyl,
(c) ($C_2$–$C_4$)-alkenyl,
(d) ($C_1$–$C_4$)-alkoxyalkyl,
(e) —$CH_2$—O—$C(O)CH_3$, or
(f) —$CH_2$-phenyl, wherein the phenyl is unsubstituted or substituted with a substituent selected from the group consisting of: —$NO_2$, —$NH_2$, —OH or —$OCH_3$;

$R^{20}$ is:
CN, $NO_2$, $CO_2R^2$, ($C_1$–$C_6$)-perfluoroalkyl or $CF_3$; and $R^{21}$ is:
(a) aryl, or
(b) ($C_1$–$C_4$)-alkyl, is unsubstituted or substituted with:
  i) $NH_2$,
  ii) NH[($C_1$–$C_4$)-alkyl],
  iii) N[($C_1$–$C_4$)-alkyl]$_2$,
  iv) $CO_2H$,
  v) $CO_2$($C_1$–$C_4$)-alkyl,
  vi) OH,
  vii) $SO_3H$, or
  viii) $SO_2NH_2$;

or a pharmaceutically acceptable salt thereof.

One embodiment of the novel compounds is that wherein:

$R^1$ is:
(a) ($C_1$–$C_6$)-alkyl, ($C_2$–$C_6$)-alkenyl or ($C_2$–$C_6$)-alkynyl each of which can be unsubstituted or substituted with a substituent selected from the group consisting of:
  i) aryl, wherein aryl is defined as phenyl or naphthyl, unsubstituted or substituted with 1 or 2 substituents selected from the group consisting of: Cl, Br, I, F, ($C_1$–$C_4$)-alkyl, ($C_1$–$C_4$)-alkoxy, $NO_2$, $CF_3$, $SO_2NR^2R^2$, ($C_1$–$C_4$)-alkylthio, hydroxy, amino, ($C_3$–$C_7$)-cycloalkyl, $CO_2H$, $CO_2$—($C_1$–$C_4$)-alkyl, or ($C_3$–$C_{10}$)-alkenyl,
  ii) ($C_3$–$C_7$)-cycloalkyl,
  iii) Cl, Br, I, F,
  iv) OH,
  v) $NH_2$,
  vi) NH($C_1$–$C_4$)-alkyl,
  vii) N[($C_1$–$C_4$)-alkyl)]$_2$,
  viii) $NHSO_2R^2$,
  ix) $CF_3$,
  x) $COOR^2$, or
  xi) $SO_2NHR^2$,
(b) ($C_1$–$C_4$)-perfluoroalkyl, or
(c) ($C_3$–$C_7$)-cycloalkyl, which can be substituted or unsubstituted with a substitutent selected from the group consisting of: ($C_1$–$C_4$)-alkyl, ($C_1$–$C_4$)-perfluoroalkyl, Cl, Br, I or F;

E is:
(a) single bond, (b) —S—, or
(c) —O—;

n is 0, 1, or 2;

$J^1$ is (a) —C(=M)—, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{7b}$, $R^{8a}$ and $R^{8b}$;

$K^1$ is (a) —C(=M)—, or (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a six-membered aromatic ring containing one nitrogen atom substituted with $R^{7a}$, $R^{7b}$ and $R^{8a}$ provided that one and only one of $J^1$ and $K^1$ is —C(=M)—;

one of $a^1$ or $b^1$ is a double bond in structure Ia provided that when $J^1$ is —C(=M)— then $b^1$ is a double bond and when $K^1$ is —C(=M)— then $a^1$ is a double bond;

$J^2$ is (a) —C(=M)—, or (b) —C($R^{17}$)—;

$K^2$ is (a) —C(=M)—, or (b) —C($R^{17}$)—, provided that one and only one of $J^2$ and $K^2$ is —C(=M)—; one of $a^2$ or $b^2$ is a double bond in structure Ic provided that when $J^2$ is —C(=M)— then $b^2$ is a double bond and when $K^2$ is —C(=M)— then $a^2$ is a double bond;

M is O, S or $NR^{15}$;

$R^2$ is:
 (a) H,
 (b) $(C_1-C_6)$-alkyl,
 (c) —$CH_2$—O—C(O)$CH_3$,
 (d) $CH_2$-aryl, or
 (e) aryl;

$R^{7a}$ and $R^{7b}$ are independently
 (a) H,
 (b) $(C_1-C_6)$-alkyl, $(C_2-C_6)$-alkenyl or $(C_2-C_6)$-alkynyl,
 (c) Cl, Br, I, F,
 (d) $CF_3$, or
 (e) when $R^{7a}$ and $R^{7b}$ are bonded to adjacent carbon atoms, they can be joined to form a phenyl or naphthyl ring;

$R^{8a}$ and $R^{8b}$ are independently
 (a) H,
 (b) aryl-$(C_1-C_4)$-alkyl,
 (c) heteroaryl-$(C_1-C_4)$-alkyl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, or F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy,
  ix) $CF_3$,
  x) $CO_2$—$(C_1-C_4)$-alkyl,
  xi) $NH_2$,
  xii) NH[$(C_1-C_4)$-alkyl], or
  xiii) N[$(C_1-C_4)$-alkyl]$_2$,
 (d) $(C_1-C_6)$-alkyl, is unsubstituted or substituted with a substituent selected from the group consisting of: —CON($R^2$)$_2$, -heteroaryl, —S(O)$_x$—$R^{21}$, -tetrazol-5-yl, —CONHSO$_2R^{21}$, —SO$_2$NH-heteroaryl, —SO$_2$NHCOR$^{21}$, —PO(OR$^2$)$_2$, —PO(OR$^2$)$_2$, —SO$_2$NH—CN, —NR$^2$COOR$^{21}$, —OH, —NH$_2$, guanidino, $(C_1-C_4)$-alkoxy, $(C_1-C_4)$-alkylthio, $(C_1-C_4)$-alkylamino, $(C_1-C_4)$-dialkylamino, —COOR$^2$, —CONHR$^2$, —O—COR$^2$, or aryl,
 (e) —CO-aryl,
 (f) $(C_3-C_7)$-cycloalkyl,
 (g) Cl, Br, I, F,
 (h) —OH,
 (i) —OR$^{21}$,
 (j) —SH,
 (k) —S(O)$_n$—$(C_1-C_4)$-alkyl,
 (l) —COR$^2$,
 (m) —CO$_2$H,
 (n) —CO$_2$—$(C_1-C_4)$-alkyl,
 (o) —SO$_3$H,
 (p) —NR$^2R^{21}$,
 (q) —NR$^2$COR$^{21}$,
 (r) —NR$^2$COOR$^{21}$,
 (s) —SO$_2$NR$^2$,
 (t) —SO$_2$NR$^2R^2$,
 (u) —NO$_2$,
 (v) —NHSO$_2$CF$_3$,
 (w) —CONR$^2R^2$,
 (x) —$(C_1-C_4)$-perfluoroalkyl,
 (y) —COOR$^2$,
 (z) —SO$_3$H,
 (aa) —N($R^2$)SO$_2R^{21}$,
 (bb) —NR$^2$CONR$^2R^{21}$,
 (cc) —OC(=O)NR$^{21}R^2$,
 (dd) -aryl,
 (ee) —NHSO$_2$CF$_3$,
 (ff) —SO$_2$NH-heteroaryl,
 (gg) —SO$_2$NHCOR$^{21}$,
 (hh) —CONHSO$_2R^{21}$,
 (ii) —PO(OR$^2$)$_2$,
 (jj) -tetrazol-5-yl,
 (kk) —CONH(tetrazol-5-yl),
 (ll) —SO$_2$NHCN, or
 (mm) -heteroaryl;

—$Y^1$—$Y^2$—$Y^3$—$Y^4$— is:
 (a) —N=CR$^{11}$—CR$^{11}$=CR$^{11}$—,
 (b) —CR$^{11}$=N—CR$^{11}$=CR$^{11}$—,
 (c) —CR$^{11}$=CR$^{11}$—N=CR$^{11}$—, or
 (d) —CR$^{11}$=CR$^{11}$—CR$^{11}$=N—,
wherein a represents a double bond in each of the above definitions [(a) thru (d)];

$R^9$ and $R^{10}$ are each independently:
 (a) H,
 (b) Cl, Br, I, F,
 (c) CF$_3$,
 (d) $(C_1-C_6)$-alkyl,
 (e) $(C_1-C_6)$-acyloxy,
 (f) $(C_3-C_6)$-cycloalkyl,
 (g) $(C_1-C_6)$-alkoxy,
 (h) hydroxy-$(C_1-C_4)$-alkyl,
 (i) aryl-$(C_1-C_4)$-alkyl,
 (j) $(C_1-C_4)$-alkylthio,
 (k) $(C_1-C_4)$-alkylsulfinyl,
 (l) $(C_1-C_4)$-alkylsulfonyl, or
 (m) when $R^9$ and $R^{10}$ are bonded to adjacent carbon atoms, they can be joined to form a phenyl or naphthyl ring;

$R^{11}$ is:
 (a) H,
 (b) Cl, Br, I, F,
 (c) NO$_2$,
 (d) NH$_2$, (e) ($C_1$-$C_4$)-alkylamino,
(f) di-($C_1$-$C_4$-alkyl)amino
(g) $SO_2NHR^2$,
(h) $CF_3$,
(i) ($C_1$-$C_4$)-alkyl,
(j) ($C_1$-$C_4$)-alkoxy, or
(k) when two $R^{11}$ substituents are bonded to adjacent carbon atoms, they can be joined to form a phenyl or naphthyl ring;

$R^{12}$ is:
(a) H,
(b) ($C_1$-$C_4$)-alkyl, or
(c) phenyl or —$CH_2$—phenyl, in which the phenyl is unsubstituted or substituted with one or two substituents selected from the group consisting of: Cl, Br, I, F, ($C_1$-$C_4$)-alkyl, or ($C_1$-$C_4$)-alkoxy, $CF_3$, NH[($C_1$-$C_4$)-alkyl], N[($C_1$-$C_4$)-alkyl]$_2$, $NH_2$ or $CO_2R^2$;

Z is:
(a) —$CO_2R^2$,
(b) —CN,
(c) —$SO_2$NH-heteroaryl,
(d) —$CH_2SO_2$NH-heteroaryl,
(e) —$SO_2$NHC(O)$R^{14}$,
(f) —C(O)NHSO$_2R^{14}$,
(g) —NHSO$_2R^{14}$, or
(h) -1H-tetrazol-5-yl;

$R^{14}$ is:
(a) aryl,
(b) heteroaryl,
(c) ($C_3$-$C_7$)-cycloalkyl,
(d) ($C_1$-$C_4$)-alkyl, unsubstituted or substituted with a substituent selected from the group consisting of: aryl, heteroaryl, —OH, —SH, ($C_1$-$C_4$)-alkyl, ($C_1$-$C_4$)-alkoxy, ($C_1$-$C_4$)-alkylthio, —$CF_3$, Cl, Br, F, I, —$NO_2$, —$CO_2H$, $CO_2$—($C_1$-$C_4$)-alkyl, —$NH_2$, —N[($C_1$-$C_4$)-alkyl]$_2$, —NH[($C_1$-$C_4$)-alkyl], —$PO_3H$, PO(OH)($C_1$-$C_4$)-alkyoxy, or
(e) ($C_1$-$C_4$)-perfluoroalkyl;

$R^{15}$ is:
(a) H,
(b) aryl,
(c) ($C_1$-$C_6$)-alkyl, ($C_2$-$C_6$)-alkenyl or ($C_2$-$C_6$)-alkynyl each of which is unsubstituted or substituted with one of more substituents selected from the group consisting of: aryl, ($C_3$-$C_7$)-cycloalkyl, Cl, Br, I, F, —OH, —$NH_2$, —NH[($C_1$-$C_4$)-alkyl], —N[($C_1$-$C_4$)-alkyl]$_2$, —NH—SO$_2R^2$, —$COOR^2$, —$SO_2NHR^2$, or
(d) heteroaryl;

$R^{16}$ is:
(a) ($C_1$-$C_{10}$)-alkyl;
(b) substituted ($C_1$-$C_{10}$)-alkyl in which one or two substituent(s) is (are) selected from:
(1) hydroxy,
(2) ($C_1$-$C_5$)-alkoxy,
(3) ($C_1$-$C_5$)-alkoxycarbonyl,
(4) phenyl,
(5) carboxy,
(6) C(=O)NH—($C_1$-$C_5$)-alkyl,
(c) phenyl unsubstituted or substituted with V and W, or
(d) naphthyl unsubstituted or substituted with V and W;

V and W are selected from:
(a) H,
(b) ($C_1$-$C_5$)-alkoxy,
(c) ($C_1$-$C_5$)-alkyl,
(d) hydroxy,
(e) —CN,
(f) —$NO_2$,
(g) —$NR^2R^2$,
(h) —$CO_2R^2$,
(i) —($C_1$-$C_5$)-perfluoroalkyl,
(j) I, Br, Cl, F,
(k) hydroxy-($C_1$-$C_4$)-alkyl-,
(l) tetrazol-5-yl,
(m) —NH—$SO_2CF_3$,
(n) —[($C_1$-$C_4$)-alkyl]$NR^2R^{21}$,
(o) —[($C_1$-$C_4$)-alkyl]$NR^2COR^{21}$,
(p) —[($C_1$-$C_4$)-alkyl]$NR^2COOR^{21}$,
(q) —[($C_1$-$C_4$)-alkyl]$CONR^2R^2$,
(r) —[($C_1$-$C_4$)-alkyl]N($R^2$)$SO_2R^{21}$,
(s) —[($C_1$-$C_4$)-alkyl]$NR^2CONR^4R^{21}$, or
(t) —[($C_1$-$C_4$)-alkyl]OC(=O)$NR^{21}R^2$; and $R^{17}$ and $R^{18}$ are independently
(a) H,
(b) aryl-($C_1$-$C_4$)-alkyl-,
(c) heteroaryl-($C_1$-$C_4$)-alkyl-,
(d) ($C_1$-$C_4$)-alkyl, unsubstituted or substituted with a substituent selected from the group consisting of: —OH, —$NH_2$, guanidino, ($C_1$-$C_4$)-alkoxy, ($C_1$-$C_4$)-alkylthio, ($C_1$-$C_4$)-alkylamino, ($C_1$-$C_4$)-dialkylamino, —$COOR^2$, —$CONHR^2$, or —O—$COR^2$, $CF_3$,
(e) ($C_1$-$C_4$)-alkenyl,
(f) —CO—aryl,
(g) ($C_3$-$C_7$)-cycloalkyl,
(h) Cl, Br, I, F,
(i) —OH,
(j) —O—($C_1$-$C_4$)-alkyl,
(k) —($C_1$-$C_4$)-perfluoroalkyl,
(l) —SH,
(m) —S(O)$_n$—($C_1$-$C_4$)-alkyl,
(n) —CHO,
(o) —$CO_2R^2$,
(p) —$SO_3H$,
(q) —$NH_2$,
(r) —NH[($C_1$-$C_4$)-alkyl],
(s) —N[($C_1$-$C_4$)-alkyl]$_2$,
(t) —$NHCO_2$—($C_1$-$C_4$)-alkyl,
(u) —$SO_2NR^2R^2$,
(v) —$CH_2OCOR^2$,
(w) —NH—$SO_2$—($C_1$-$C_4$)-alkyl,
(x) 5 or 6 membered saturated heterocycle containing one nitrogen atom and optionally containing one other heteroatom selected from N, O, or S, such as pyrrolidine, morpholine, or piperazine,
(y) aryl,
(z) heteroaryl,
(aa) tetrazol-5-yl, or
(bb) —[($C_1$-$C_4$)-alkyl]$NR^2R^{21}$,
(cc) —[($C_1$-$C_4$)-alkyl]$NR^2COR^{21}$,
(dd) —[($C_1$-$C_4$)-alkyl]$NR^2COOR^{21}$,
(ee) —[($C_1$-$C_4$)-alkyl]$CONR^2R^2$,
(ff) —[($C_1$-$C_4$)-alkyl]N($R^2$)$SO_2R^{21}$,
(gg) —[($C_1$-$C_4$)-alkyl]$NR^2CONR^2R^{21}$, or
(hh) —[($C_1$-$C_4$)-alkyl]OC(=O)$NR^{21}R^2$; and $R^{21}$ is:
(a) aryl, or
(b) ($C_1$-$C_4$)-alkyl which is unsubstituted or substituted with:
i) $NH_2$,
ii) NH[($C_1$-$C_4$)-alkyl],
iii) N[($C_1$-$C_4$)-alkyl]$_2$,
iv) $CO_2H$, v) $CO_2(C_1-C_4)$-alkyl,
vi) OH,
vii) $SO_3H$, or
viii) $SO_2NH_2$, or a pharmaceutically acceptable salt thereof.

Another embodiment of the invention is that wherein:

$R^1$ is:
   (a) $(C_1-C_6)$-alkyl $(C_2-C_6)$-alkenyl or $(C_2-C_6)$-alkynyl each of which is unsubstituted or substituted with a substituent selected from the group consisting of:
      i) $(C_1-C_4)$-alkylthio,
      ii) $(C_1-C_4)$-alkoxy,
      iii) $CF_3$,
      iv) $CF_2CF_3$, or
      v) $(C_3-C_5)$-cycloalkyl,
   (b) perfluoro-$(C_1-C_4)$-alkyl, or
   (c) $(C_3-C_7)$-cycloalkyl, which can be substituted or unsubstituted with a substitutent selected from the group consisting of: $(C_1-C_4)$-alkyl, $(C_1-C_4)$-perfluoroalkyl, Cl, Br, I or F;

E is a single bond;
n is 0 to 2;
$J^1$ and L are connected together to form a 6-carbon aromatic ring substituted with $R^{7a}$, $R^{7b}$, $R^{8a}$ and $R^{8b}$; or $J^1$ and L are connected together to form a 6-membered aromatic ring containing one nitrogen atom not at $J^1$, substituted with $R^{7a}$, $R^{7b}$, $R^{8a}$ and $R^{8b}$;
$K^1$ is —C(=M)—;
$a^1$ is a double bond;
$J^2$ is —C($R^{17}$)—;
$K^2$ is —C(=M)—;
$a^2$ is a double bond;
M is O, or $NR^{15}$;

$R^2$ is:
   (a) H,
   (b) $(C_1-C_6)$-alkyl,
   (c) —$CH_2$—O—C(O)$CH_3$,
   (d) benzyl, or
   (e) phenyl;

$R^{7a}$ and $R^{7b}$ are independently
   (a) H,
   (b) $(C_1-C_6)$-alkyl, $(C_2-C_6)$-alkenyl or $(C_2-C_6)$-alkynyl,
   (c) Cl, Br, I, F,
   (d) $CF_3$, or
   (e) when $R^{7a}$ and $R^{7b}$ are bonded to adjacent carbon atoms, they can be joined to form a phenyl ring;

$R^{8a}$ and $R^{8b}$ are independently
   (a) H,
   (b) aryl-$(C_1-C_4)$-alkyl, wherein aryl is defined as phenyl or naphthyl unsubstituted or substituted with 1 or 2 substituents selected from the group consisting of:
      i) Br, I, Cl, F,
      ii) $(C_1-C_4)$-alkyl,
      iii) $(C_1-C_4)$-alkoxy,
      iv) $NO_2$,
      v) $CF_3$,
      vi) $SO_2NR^2R^2$,
      vii) $(C_1-C_4)$-alkylthio,
      viii) hydroxy,
      ix) amino,
      x) $(C_3-C_7)$-cycloalkyl,
      xi) $(C_3-C_{10})$-alkenyl,
      xii) $CO_2H$, or
      xiii) $CO_2$—$(C_1-C_4)$-alkyl;
   (c) heteroaryl-$(C_1-C_4)$-alkyl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
      i) Cl, Br, I, or F,
      ii) OH,
      iii) SH,
      iv) $NO_2$,
      v) $(C_1-C_4)$-alkyl,
      vi) $(C_2-C_4)$-alkenyl,
      vii) $(C_2-C_4)$-alkynyl,
      viii) $(C_1-C_4)$-alkoxy,
      ix) $CF_3$,
      x) $CO_2$—$(C_1-C_4)$-alkyl,
      xi) $NH_2$,
      xii) NH[$(C_1-C_4)$-alkyl], or
      xiii) N[$(C_1-C_4)$-alkyl]$_2$,
   (d) $(C_1-C_6)$-alkyl, unsubstituted or substituted with a substitutent selected from the group consisting of: —CON($R^2$)$_2$, -heteroaryl, —S(O)$_n$—$R^{21}$, -tetrazol-5-yl, —CONHSO$_2R^{21}$, —SO$_2$NH-heteroaryl, —SO$_2$NHCOR$^{21}$, —PO(OR$^2$)$_2$, —PO(OR$^2$)$_2$, —SO$_2$NH—CN, —NR$^2$COOR$^{21}$, —OH, —NH$_2$, guanidino, $(C_1-C_4)$-alkoxy, $(C_1-C_4)$-alkylthio, $(C_1-C_4)$-alkylamino, $(C_1-C_4)$-dialkylamino, —COOR$^2$, —CONHR$^2$, —O—COR$^2$, or aryl,
   (e) —CO—aryl,
   (f) $(C_3-C_7)$-cycloalkyl,
   (g) Cl, Br, I, F,
   (h) —OH,
   (i) —OR$^{21}$,
   (j) —SH,
   (k) —S(O)$_n$—$(C_1-C_4)$-alkyl,
   (l) —COR$^2$,
   (m) —$CO_2H$,
   (n) —$CO_2$—$(C_1-C_4)$-alkyl,
   (o) —$SO_3H$,
   (p) —NR$^2R^{21}$,
   (q) —NR$^2$COR$^{21}$,
   (r) —NR$^2$COOR$^{21}$,
   (s) —$SO_2NR^2$,
   (t) —$SO_2NR^2R^2$,
   (u) —$NO_2$,
   (v) —$NHSO_2CF_3$,
   (w) —$CONR^2R^2$,
   (x) —$(C_1-C_4)$-perfluoroalkyl,
   (y) —COOR$^2$,
   (z) —$SO_3H$,
   (aa) —N(R$^2$)SO$_2R^{21}$,
   (bb) —NR$^2$CONR$^2R^{21}$,
   (cc) —OC(=O)NR$^{21}R^2$,
   (dd) -aryl,
   (ee) —$NHSO_2CF_3$,
   (ff) —$SO_2$NH-heteroaryl,
   (gg) —$SO_2$NHCOR$^{21}$,
   (hh) —$CONHSO_2R^{21}$,
   (ii) —PO(OR$^2$)$_2$,
   (jj) -tetrazol-5-yl,
   (kk) —CONH(tetrazol-5-yl),
   (ll) —$SO_2$NHCN, or
   (mm) -heteroaryl;

—$Y^1$—$Y^2$—$Y^3$—$Y^4$— is:
   (a) —N—CR$^{11}$=CR$^{11}$=CR$^{11}$—,
   (b) —CR$^{11}$=N—CR$^{11}$=CR$^{11}$—,
   (c) —CR$^{11}$=CR$^{11}$—N=CR$^{11}$—, or (d) —$CR^{11}$=$CR^{11}$—$CR^{11}$=N—,
wherein a represents a double bond in each of the above definitions [(a) thru (d)];

$R^9$ and $R^{10}$ are each independently:
(a) H,
(b) Cl, Br, I, F,
(c) $CF_3$,
(d) $(C_1-C_6)$-alkyl,
(e) $(C_1-C_6)$-acyloxy,
(f) $(C_3-C_6)$-cycloalkyl,
(g) $(C_1-C_6)$-alkoxy,
(h) hydroxy-$(C_1-C_4)$-alkyl,
(i) aryl-$(C_1-C_4)$-alkyl,
(j) $(C_1-C_4)$-alkylthio,
(k) $(C_1-C_4)$-alkylsulfinyl,
(l) $(C_1-C_4)$-alkylsulfonyl, or
(m) when $R^9$ and $R^{10}$ are bonded to adjacent carbon atoms, they can be joined to form a phenyl or naphthyl ring;

$R^{11}$ is:
(a) H,
(b) Cl, Br, I, F,
(c) $NO_2$,
(d) $NH_2$,
(e) $(C_1-C_4)$-alkylamino,
(f) di-$(C_1-C_4$-alkyl)amino,
(g) $SO_2NHR^2$,
(h) $CF_3$,
(i) $(C_1-C_4)$-alkyl,
(j) $(C_1-C_4)$-alkoxy, or
(k) when two $R^{11}$ substituents are bonded to adjacent carbon atoms, they can be joined to form a phenyl or naphthyl ring;

$R^{12}$ is:
(a) H,
(b) $(C_1-C_4)$-alkyl, or
(c) phenyl or —$CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, NH[$(C_1-C_4)$-alkyl], N[$(C_1-C_4)$-alkyl]$_2$, $NH_2$ or $CO_2R^2$;

Z is:
(a) —$CO_2R^2$,
(b) —CN,
(c) —$SO_2$NH-heteroaryl,
(d) —$CH_2SO_2$NH-heteroaryl,
(e) —$SO_2NHC(O)R^{14}$,
(f) —$C(O)NHSO_2R^{14}$,
(g) —$NHSO_2R^{14}$, or
(h) -1H-tetrazol-5-yl;

$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, —OH, —SH, $(C_1-C_4)$-alkyl, $(C_1-C_4)$-alkoxy, $(C_1-C_4)$-alkylthio, —$CF_3$, Cl, Br, F, I, —$NO_2$, —$CO_2H$, $CO_2$—$(C_1-C_4)$-alkyl, —$NH_2$, —N[$(C_1-C_4)$-alkyl]$_2$, —NH[$(C_1-C_4)$-alkyl], —$PO_3H$, PO(OH)$(C_1-C_4)$-alkyoxy, or
(e) $(C_1-C_4)$-perfluoroalkyl;

$R^{15}$ is:
(a) H,
(b) aryl,
(c) $(C_1-C_6)$-alkyl, $(C_2-C_6)$-alkenyl or $(C_2-C_6)$-alkynyl each of which is unsubstituted or substituted with one or more substituents selected from the group consisting of aryl as defined above, $(C_3-C_7)$-cycloalkyl, Cl, Br, I, F, —OH, —$NH_2$, —NH[$(C_1-C_4)$-alkyl], —N[$(C_1-C_4)$-alkyl]$_2$, —NH—$SO_2R^2$, —$COOR^2$, —$SO_2NHR^2$; or
(d) heteroaryl;

$R^{16}$ is
(a) $(C_1-C_{10})$-alkyl;
(b) substituted $(C_1-C_{10})$-alkyl in which one or more substituent(s) is selected from
(1) hydroxy,
(2) $(C_1-C_5)$-alkoxy,
(3) $(C_1-C_5)$-alkoxycarbonyl,
(4) phenyl,
(5) carboxy,
(6) C(=O)NH—$(C_1-C_5)$-alkyl,
(c) phenyl, unsubstituted or substituted with V and W, or
(d) naphthyl, unsubstituted or substituted with V and W;

V and W are selected from:
(a) H,
(b) $(C_1-C_5)$-alkoxy,
(c) $(C_1-C_5)$-alkyl,
(d) hydroxy,
(e) —CN,
(f) —$NO_2$,
(g) —$NR^2R^2$,
(h) —$CO_2R^2$,
(i) —$CF_3$,
(j) I, Br, Cl, F,
(k) hydroxy-$(C_1-C_4)$-alkyl-,
(l) -1H-tetrazol-5-yl, or
(m) —NH—$SO_2CF_3$;

$R^{17}$ and $R^{18}$ are independently:
(a) H,
(b) aryl-$(C_1-C_4)$-alkyl-,
(c) heteroaryl-$(C_1-C_4)$-alkyl-,
(d) $(C_1-C_4)$-alkyl, unsubstituted or substituted with a substituent selected from the group consisting of: —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^2$, —$CONHR^2$, —O—$COR^2$, $CF_3$;
(e) $(C_1-C_4)$-alkenyl,
(f) —CO-aryl,
(g) $(C_3-C_7)$-cycloalkyl,
(h) Cl, Br, I, F,
(i) —OH,
(j) —O—$(C_1-C_4)$-alkyl,
(k) —$(C_1-C_4)$-perfluoroalkyl,
(l) —SH,
(m) —$S(O)_n$—$(C_1-C_4)$-alkyl,
(n) —CHO,
(o) —$CO_2R^2$
(p) —$SO_3H$,
(q) —$NH_2$,
(r) —NH[$(C_1-C_4)$-alkyl],
(s) —N[$(C_1-C_4)$-alkyl]$_2$,
(t) —$NHCO_2$—$(C_1-C_4)$-alkyl,
(u) —$SO_2NR^2R^2$,
(v) —$CH_2OCOR^2$
(w) —NH—$SO_2$—$(C_1-C_4)$-alkyl,
(x) 5 or 6 membered saturated heterocycle containing one nitrogen atom and optionally containing one other heteroatom selected from N, O, or S, such as pyrrolidine, morpholine, or piperazine,
(y) aryl, (z) heteroaryl, or
(aa) tetrazol-5-yl; and $R^{21}$ is:
(a) aryl, or
(b) $(C_1-C_4)$-alkyl which is unsubstituted or substituted with:
   i) $NH_2$,
   ii) $NH[(C_1-C_4)$-alkyl],
   iii) $N[(C_1-C_4)$-alkyl]$_2$,
   iv) $CO_2H$,
   v) $CO_2(C_1-C_4)$-alkyl,
   vi) OH,
   vii) $SO_3H$, or
   viii) $SO_2NH_2$;
or a pharmaceutically acceptable salt thereof.

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

DETAILED DESCRIPTION OF THE INVENTION

GENERAL METHODS FOR PREPARATION OF COMPOUNDS OF FORMULA I

The methods described in PART I AND PART II below illustrate the preparation of angiotensin II antogonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formula I and a substituted benzyl substituent which is attached to the heterocyclic component at a nitrogen atom. Thus, two generally applicable approaches to antagonists of formula I are these:

1. A heterocycle, designated above in Formula I is prepared as described in PART I below. Then the heterocycle is alkylated at a nitrogen atom with a substituted benzyl halide or pseudohalide giving an alkylated heterocycle in the Schemes below, this alkylating agent is often designated as "Ar—$CH_2$Q" where Q is a halide (—Cl,Br,I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar—$CH_2$Q"), but here the alkylation step is followed by subsequent steps which are required to assemble the substituted benzyl element of the antagonist of Formula I. The alkylation steps and subsequent steps used to prepare antagonists of Formula I, are described in PART II below.

The compounds of this invention maybe resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention. Abbreviations used in the schemes and examples are listed in Table 1.

TABLE 1

| Reagents | |
|---|---|
| NBS | N-bromosuccinimide |
| AIBN | Azo(bis) isobutyronitrile |
| DDQ | Dichlorodicyanoquinone |
| $Ac_2O$ | acetic anhydride |
| TEA | triethylamine |
| DMAP | 4-dimethylaminopyridine |
| $PPh_3$ | triphenylphosphine |
| TFA | trifluroacetic acid |
| TMS—Cl | trimethylsilyl chloride |
| Im | imidazole |
| AcSK | potassium thioacetate |
| p-TsOH | p-toluenesulfonic acid |
| FMOC—Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | $OSO_2CF_3$ |
| Ph | phenyl |
| FAB-MS (FSBMS) | Fast atom bombardment mass spectroscopy |
| NOE | Nuclear Overhauser Effect |
| $SiO_2$ | silica gel |
| trityl | triphenylmethyl |

PART I: Preparation of the heterocycles shown in Formulas Ia, Ib, and Ic

A. Preparation of quinazolinones (Formula Ia)

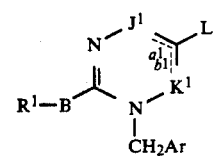

Scheme I-1 illustrates the preparation of 1,2-disubstituted quinazolin-4(1H)-ones of Formula Ia wherein $J^1$=—C(O)— and B is a single bond. An appropriately substituted anthranilonitrile is acylated using the requisite acyl chloride. The resulting amide is alkylated with sodium hydride and the appropriate alkyl halide (or pseudohalide). The resulting tertiary amide is then rearranged/cyclized with basic hydrogen peroxide[1].

SCHEME I-1

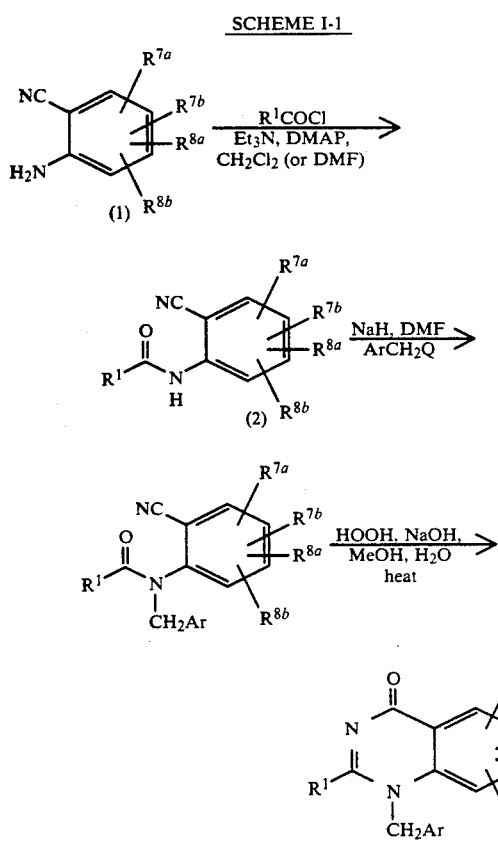

Q = Br, I, OTs, OTf
Ar = is as defined as in the generic structure Formula I

2-Substituted quinazolinones may be prepared from substituted anthranilonitriles as described in the literature and illustrated in Scheme I-2. The appropriately substituted anthranilonitrile is acylated using the requisite acyl chloride then cyclized using basic hydrogen peroxide.[1]

SCHEME I-2

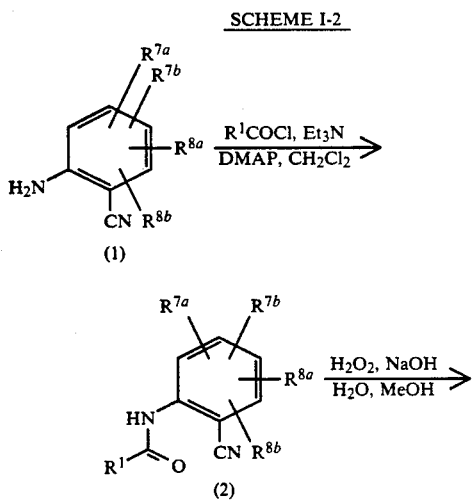

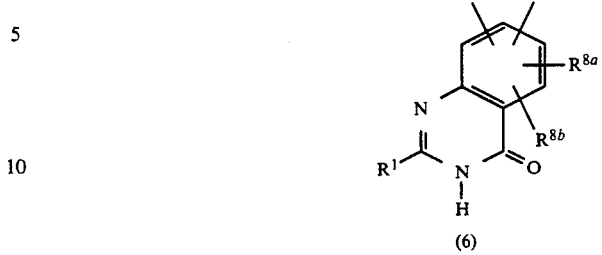

Scheme I-3 shows an alternate preparation of 2-substituted quinazolinones starting with the corresponding anthranilic acid. The appropriately substituted anthranilic acid is treated with two equivalents of the requisite acyl chloride in DMF with triethylamine and DMAP at 0° C. This is then heated to 110° C. for two hours after which time excess ammonium carbonate is added.[2]

SCHEME I-3

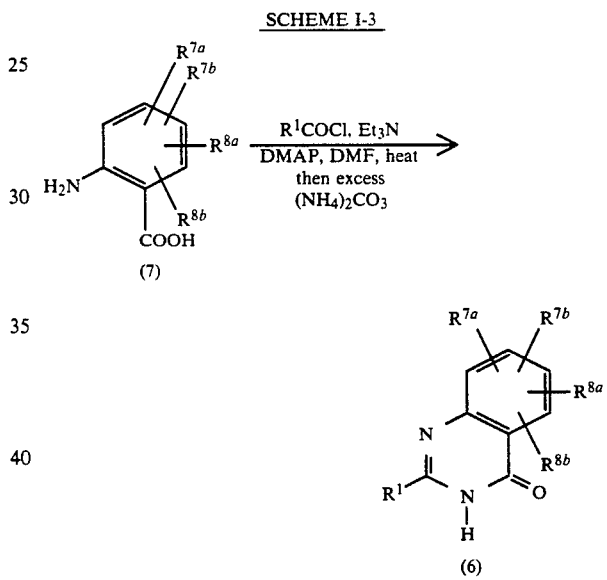

Scheme I-4 illustrates the general preparation of 2,3-disubstituted quinazolin-4-(3H)-ones of Formula Ia, wherein B is a single bond and $K^1$ is —C(O)—. An appropriately substituted 2-substituted quinazolinone (see Scheme I-2 or Scheme I-3) is alkylated using sodium hydride and the appropriate alkyl halide (or pseudohalide). This reaction sometimes gives some O-alkylated product, generally less than 20% of the isolated reaction products.

SCHEME I-4

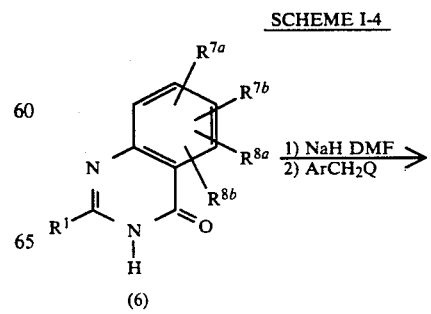

SCHEME I-4 -continued

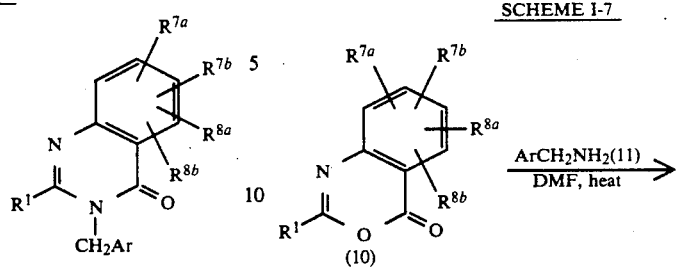

Schemes I-5, I-6, and I-7 provide an alternate route to compounds of Formula Ia, wherein B is a single bond and $K^1$ is —C(O)—.

Two methods for preparing 3,1,4-benzoxazones are illustrated in Scheme I-5. Substituted anthranilic acids may be acylated and cyclized by heating them in DMF with an acyl chloride, triethylamine and DMAP.[3] Alternatively, they may also be prepared by heating an appropriately substituted anthranil with an acyl chloride in pyridine.[4]

The necessary alkyl amine may then be prepared from the alkyl halide (or pseudohalide) using the standard literature procedures (Scheme I-6).[5] Then, the amine and the 3,1,4-benzoxazone are heated together to give the desired 2,3-disubstituted quinazolinone 2 (Scheme I-7).

SCHEME I-5

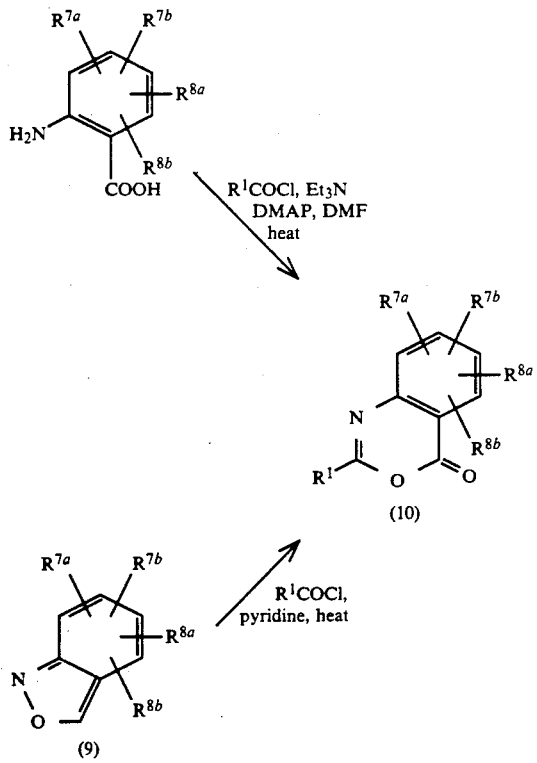

SCHEME I-6

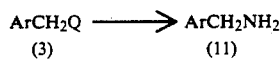

SCHEME I-7

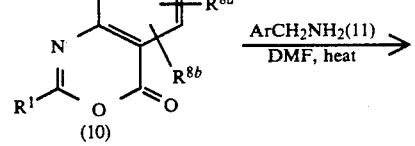

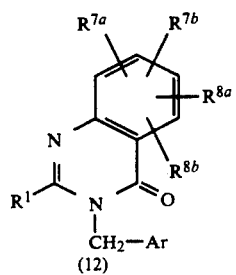

Substituted 2-alkylthioquinazolin-4(3H)-ones wherein $K^1$ is —C(O)— and E is —S— may be prepared from their corresponding substituted anthranilic acids as shown in Scheme I-8. The amine from Scheme I-6 can be converted to its isothiocyanate upon treatment with thiophosgene. This may then be reacted with an appropriately substituted anthranilic acid to give the desired 3-alkyl-2-mercapto-quinazolin-4(3H)-one.[6] A second alkylation of the mercapto group then gives the desired 2-alkylthio-3-alkylquinazolin-4(3H)-one.[7]

SCHEME I-8

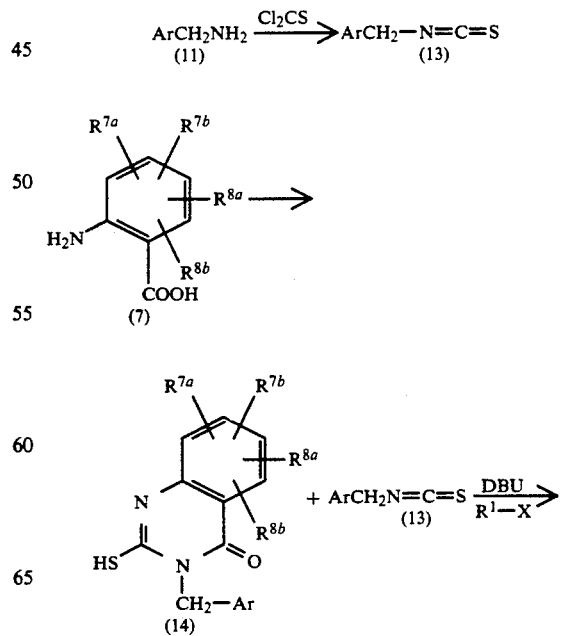

-continued
SCHEME I-8

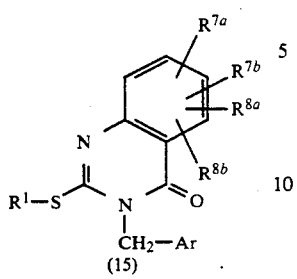
(15)

Similarly, 2-alkoxyquinazolin-4(3H)-ones wherein $K^1$ is —C(O)— and B is —O— may be prepared from their corresponding substituted anthranilic acids as shown in Scheme 9.[8] Alkylation with the appropriate alkyl halide according to the methods developed by Lange and Sheibley[9] then gives the final product 17.*

SCHEME I-9

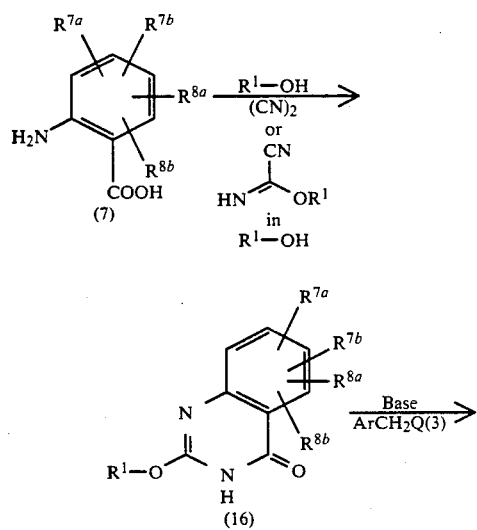

Scheme I-10 illustrates a possible route to the isomeric 1,2-disubstituted quinazolin-4(1H)-ones wherein $J^1$ is —C(O)— and where B is —S— or —O—. An anthranilonitrile can be acylated with an alkyl haloformate or an alkylthiol haloformate.[10] This may then be deprotonated and alkylated with the appropriate alkyl halide to give the intermediate carbamate nitrile shown.[11] Conversion of the intermediate then could occur when the material is treated with basic hydrogen peroxide to yield the desired product 20.

SCHEME I-10

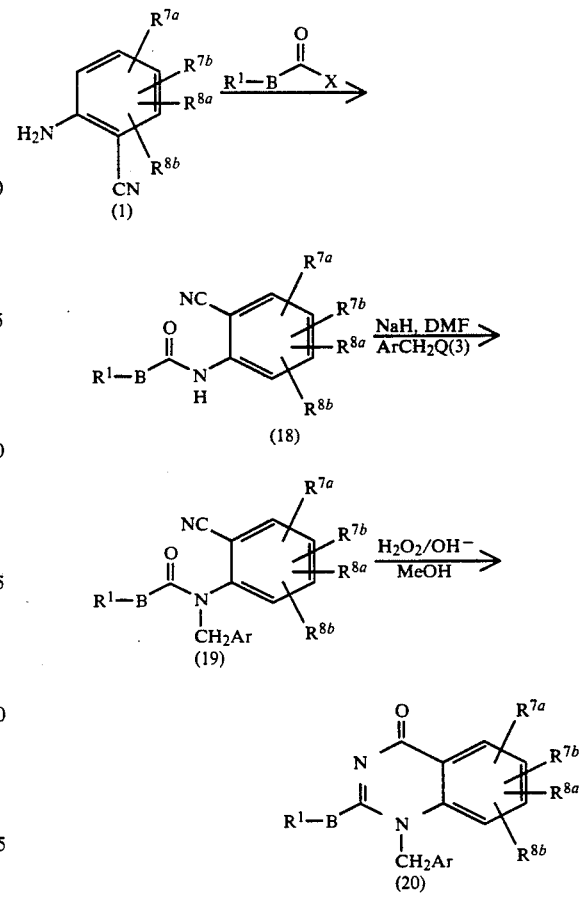

Scheme I-11 illustrates the method by which a 2-amino-3-alkylquinazolinone can be made. The 2-mercaptoquinazolinone (14) shown in Scheme I-8 can be treated with sulfuryl chloride to give the corresponding 2-chloroquinazolinone.[12] Displacement of the chloride with an $R^1$ amine then gives 20 with B=NH.[13]

SCHEME I-11

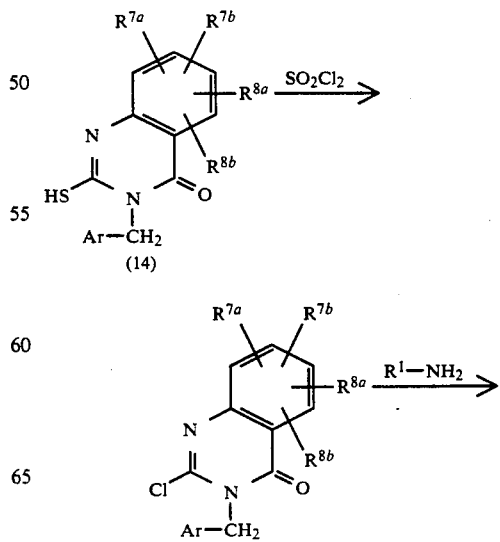

SCHEME I-11

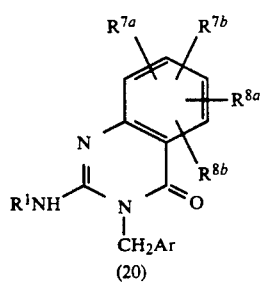

Scheme I-12 illustrates the method by which a 2-amino-1-alkylquinazolinone can be made. The products from Scheme I-10 can be used as a synthetic intermediate if the initial $R^1$ is a protecting group such as benzyl or t-butyl.[14] Deprotection and subjection of the resulting 2-mercapto-1-alkyl-quinazolinone to the same conditions used in Scheme I-11 will result in the formation of the desired 2-amino-1-alkylquinazolin-4(1H)-one. Alternatively, the sulfide may be displaced directly by an $R^1$ amine as shown in Scheme I-13 ($R^1$—S— and $R^1$—NH$_2$ may or may not have the same $R^1$).

SCHEME I-12

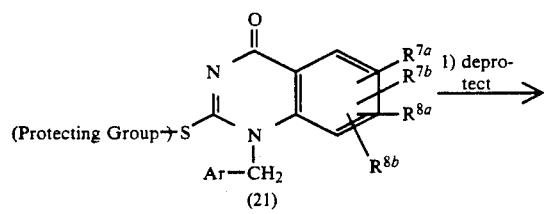

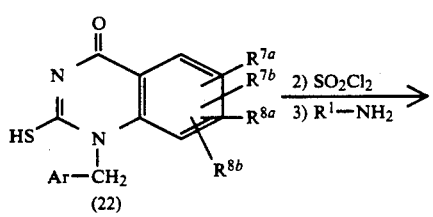

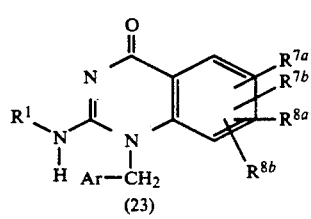

SCHEME I-13

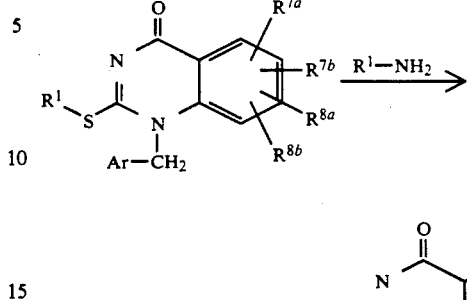

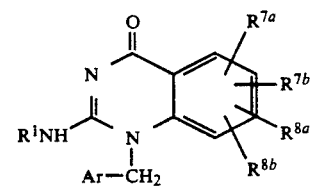

The preparation of quinazolinones of general Formula Ia bearing substituted C-6 amino groups may be accomplished as illustrated in Schemes I-14 through I-16. In order to prepare these derivatives, the amide group of a 6-nitroquinazolin-4(3H)-one is usually first protected with an acid labile protecting group as shown in Scheme I-14. For instance, reaction of the generalized 6-nitroquinazolin-4(3H)-one (24) with a base such as sodium hydride in DMF followed by addition of bis(4-methoxyphenyl)methyl chloride affords the N-protected derivative 25. The nitro group of 25 may be reduced to the amine 26 by reduction with hydrogen over palladium on carbon. The amine (26) may then be reacted with a variety of reagents known to form derivatives of amines such as alkyl- or aryl-carboxylic acid chlorides, chloroformates, sulfonyl and sulfamoyl chlorides, isocyanates and isothiocyanates. Scheme I-14 illustrates the derivatization of amine 26 with a generalized chloroformate to afford substituted carbamates such as 27. The acylation of amine 26 with a chloroformate is best carried out in the presence of a strong base such as sodium hydride to deprotonate the amine. This anion then reacts readily with chloroformates to give the substituted carbamates 27. The carbamate (27) may be isolated, then deprotonated with lithium bis(trimethylsilyl)amide and alkylated to give the N,O-disubstituted carbamates 28. Alternatively, this process may be carried out in one flask by first deprotonating the aniline (i.e. with sodium hydride in DMF), reacting the anion with an acyl halide or chloroformate, then treating the intermediate with an equivalent of a strong base such as lithium bis(trimethylsilyl)amide and finally adding an alkylating agent to obtain 28. The carbamoyl-substituted quinazolinones 27 and 28 may be cleanly deprotected under acidic conditions such as trifluoroacetic acid-anisole to afford the heterocycles 29 and 30 respectively.

SCHEME I-14
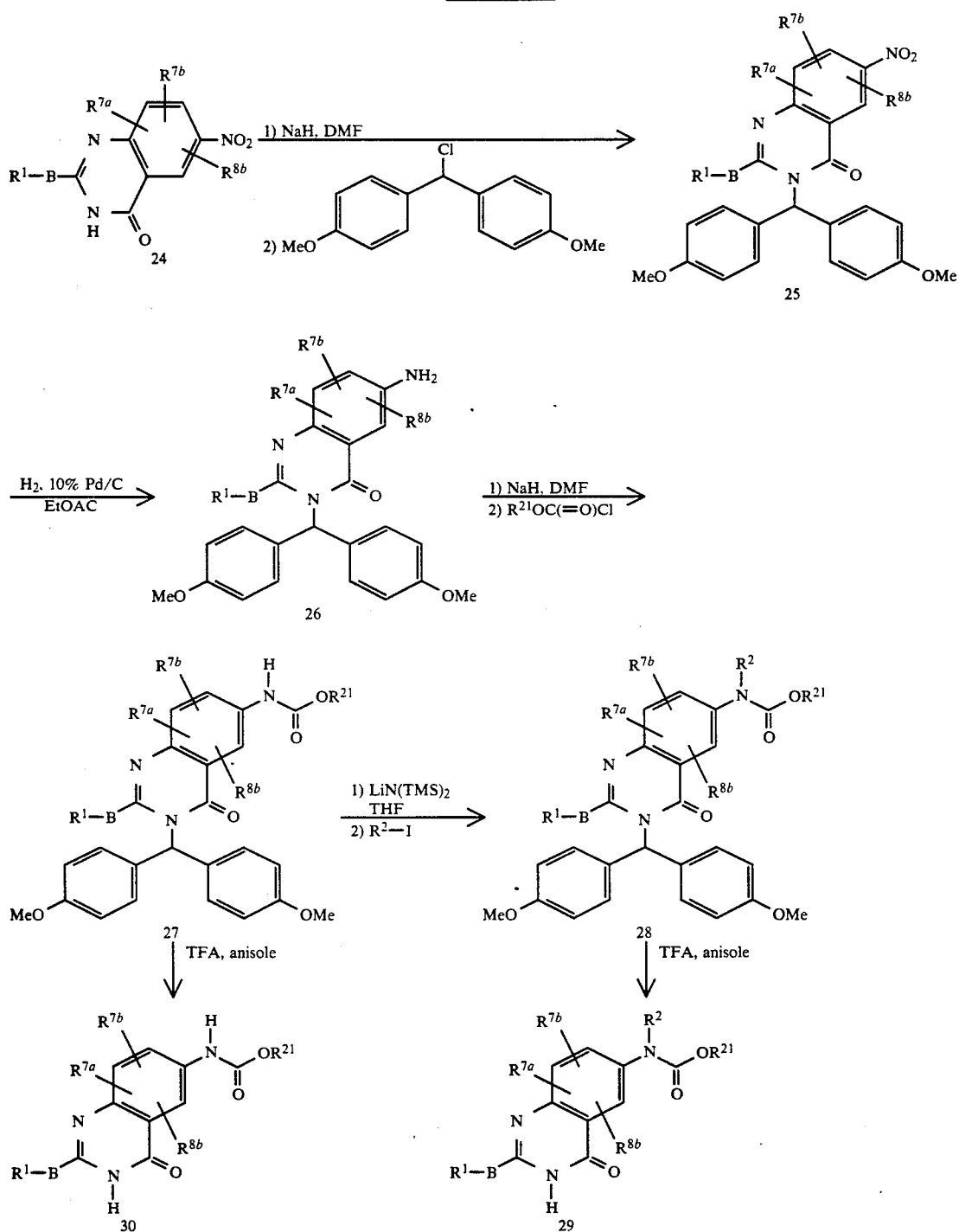

SCHEME I-15

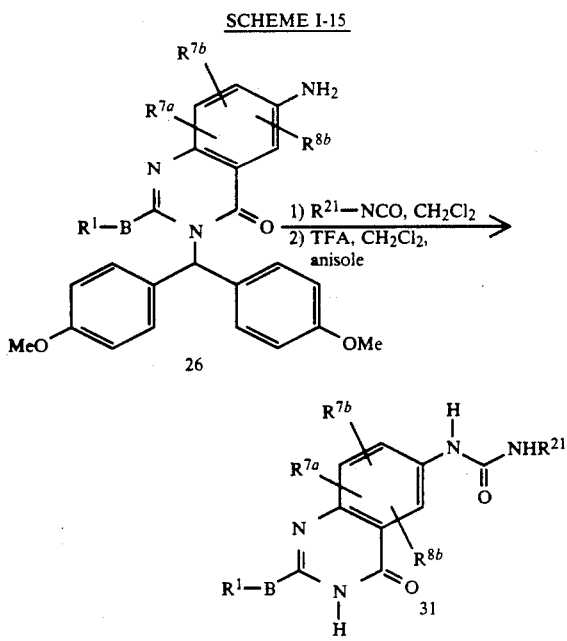

Scheme I-15 illustrates the reaction of amine 25 with isocyanates to give disubstituted ureas (31). Tetrasubstituted and trisubstituted ureas such as 34 and 35 may be prepared from the benzyl carbamate 27 as shown in Scheme I-16. Thus, treatment of 27 with the magnesium salt of a secondary amine formed from the secondary amine and methylmagnesium bromide affords the trisubstituted urea 32. Trisubstituted ureas (32) may be N-alkylated by deprotonation of the remaining hydrogen with lithium bis(trimethylsilyl)amide followed by alkylation with an alkyl iodide to give 33. The urea-substituted quinazolinones 32 and 33 may be cleanly deprotected under acidic conditions such as trifluoroacetic acid-anisole to afford the heterocycles 34 and 35 respectively. The amine 26 (Scheme I-14) may be derivatized or converted to other functional groups using chemical procedures well known to those skilled in the art. After the appropriate 6-substituent has been constructed the protecting group may be removed by treatment with trifluoroacetic acid in the presence of anisole as illustrated in Schemes I-14 through I-16. The heterocycles obtained in this manner may be incorporated into Angiotensin II Antagonists of general Formula Ia as described in Part II.

SCHEME I-16

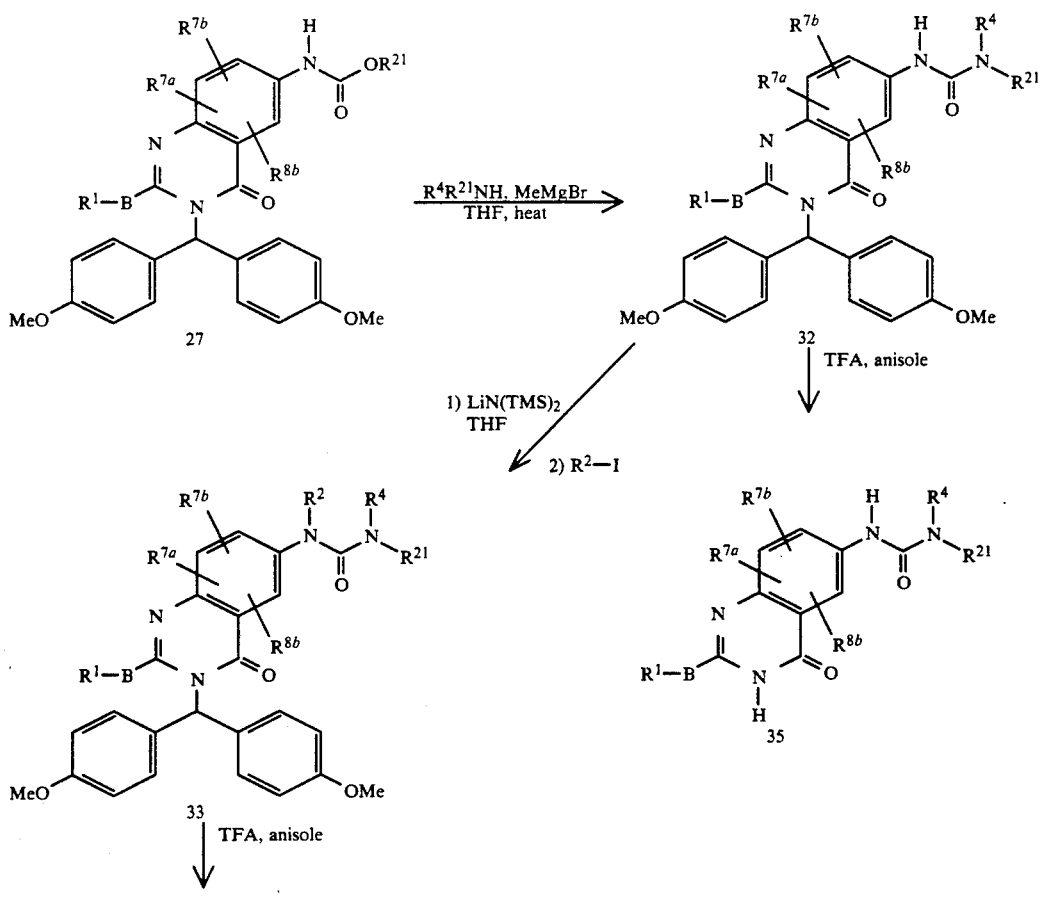

-continued
SCHEME I-16

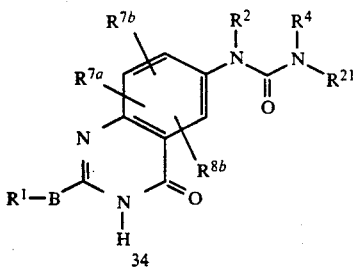

For a general review of the synthesis and reactivity of 2,3-disubstituted pyrido[2,3-d] or [3,4-d] or [3,2-d] or [4,3-d]pyrimidin-4(3HO-ones, see A. R. Katritzky, et al., *Comprehensive Heterocyclic Chemistry*, vol. 3, 201 (1984) and W. J. Irwin, et al., *Advances in Heterocyclic Chemistry*, vol. 10, 149 (1969).

QUINAZOLINONE REFERENCES

1 E. C. Taylor, R. J. Knopf, A. L. Borror, *J. Am. Chem. Soc.* (1960) 82, 3152. R. L. McKee, M. K. McKee, R. W. Bost, *J. Am. Chem. Soc.* (1946) 68, 1902. A. Khan, R. K. Saksena, *Pharmazie* (1988) 43H. 12.
2 M. T. Bogert, W. F. Hand, *J. Am. Chem. Soc.* (1906) 28, 94.
3 See A. Khan, reference 1. L. A. Errede, J. J. McBrady, H. T. Oien, *J. Org. Chem.* (1977) 42, 656. L. A. Errede, *J. Org. Chem.* (1976) 41 1763. L. A. Errede, H. T. Oien, D. R. Yarian, *J. Org. Chem.* (1977) 42, 12.
4 K. Wunsch, A. J. Boulton, *Adv. Het. Chem.* (1967) 8, pp 326-9, and references therein. I. R. Gambhir, S. S. Joshi, *J. Ind. Chem. Soc.* (1964) 41, 47.
5 Bayley, Stranding, Knowles, *Tetrahedron. Lett.* (1978) 3633. Rolla, *J. Org. Chem.* (1982) 47, 4327. Gibson, Bradshaw, *Angew. Chem. Int. Ed. Engl.* (1968) 7, 919.
6 R. G. Dave, G. S. Mewada, G. C. Amin, *J. Ind. Chem. Soc.* (1960) 37, 595.
7 J. E. McCarty, E. L. Haines, C. A. VanderWerf, *J. Am. Chem. Soc.* (1960) 82, 964. P. N. Bhargava, P. Ram, *Bull. Chem. Soc. Jap.* (1965) 38, 342. M. R. Chaurasia, A. K. Sharma, *Heterocycles* (1983) 20, 1549. K. Lempert, G. Doleschall, *Chem Ber.* (1963) 96, 1271. H. Singh, K. S. Narang, *J. Ind. Chem. Soc.* (1963) 40, 545. M. S. Dhatt, K. S. Narang, *J. Ind. Chem. Soc.* (1954) 31, 787. M. S. Dhatt, K. S. Narang, *J. Ind. Chem. Soc.* (1954) 31, 864. D. S. Bariana, H. S. Sachdev, K. S. Narang, *J. Ind. Chem. Soc.* (1955) 32, 647.
8 Griess, *Ber. Deut. Chem. Ges.* (1869) 2, 415.
9 N. A. Lang, F. E. Sheibley, *J. Am. Chem. Soc.* (1933) 55, 1188.
10 H. B. Milne, S. L. Razniak, R. P. Bayer, D. W. Fish, *J. Am. Chem. Soc.* (1960) 82, 4582. E. J. Corey, M. G. Bock, A. P. Kozikowski, A. V. R. Rao, D. Floyd, B. Lipshutz, *Tetrahedron Lett.* (1978) 1051. M. Bergmann, L. Zervas, *Ber.* (1932) 65 1192.
11 R. L. Dannley, M. Lukin, *J. Org. Chem.* (1957) 22, 268. R. Zibuck, N. J. Liverton, A. B. Smith, *J. Am. Chem. Soc.* (1986) 10,8 2451.
12 D. J. Brown, *Fused Pyrimidines*, Part I Quinazolines, (1967), J. Wiley & Sons, p. 222.
13 D. J. Brown, *Fused Pyrimidines*, Part I Quinazolines, (1967), J. Wiley & Sons, p. 323.
14 T. W. Greene, *Protective Groups in Organic Synthesis*, (1981), J. Wiley & Sons, pp. 193-217.

B. Preparation of triazolinones, triazolinethiones and triazolinimines (Formula Ib)

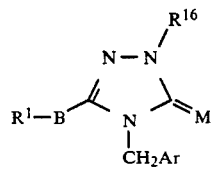

The compounds of Formula Ib can be prepared by a variety of methods typified by those described below in Schemes I-17 to I-28. General synthetic methods for 2,4,5-trisubstituted-1,2,4-triazolin-3(4H)-ones and -triazolin-3(4H)-thiones are discussed in books or review articles such as:

(1) C. Temple and J. A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365-442.

(2) J. B. Polya, *Comprehensive Heterocyclic Chemistry. The Structure, Reactions, Synthesis and Uses of Heterocyclic Compounds*, A. R. Katritzky and C. W. Rees, eds., Vol. 5, Pergamon Press, Oxford, 1984, pp. 733-790.

(3) J. H. Boyer, *Heterocyclic Compounds*, R. C. Elderfield, ed., Vol. 7, John Wiley & Sons, New York, 1961, pp. 384-461.

In general, the compounds of Formula Ib are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate or isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula Ib may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "ArCH$_2$" substituent present at $N^4$ of the triazole derivatives or in their precursors is any substituted arylmethyl moiety consistent with the definition of the $N^4$ substituent in Formula Ib or which may be transformed to such a grouping either before or after the assembly of the triazole ring system. Such transformations may involve protection and/or deprotection steps, as described above in the "General Methods" section or other modifications. It is also to be understood that in most of the Reaction Schemes, the "ArCH$_2$" (Ar=aryl) substituent is consistent with the definition of Formula I.

It is further to be understood that in the generalized schemes below, unless specified otherwise, the $R^1$ and $R^{16}$ groups represent functionalized or unfunctionalized alkyl, aryl, heteroaryl, arylalkyl, and the like. The moiety, $R^{16}Q$, represents an alkylating agent in which $R^{16}$ is typically a functionalized or unfunctionalized alkyl or aralkyl group, while Q is a leaving group such as chloro, bromo, iodo, methanesulfonate, or p-toluenesulfonate. In structures showing an "X" group double-bonded to a carbon atom (as in 22 and products derived therefrom), M is O or S.

SCHEME I-17

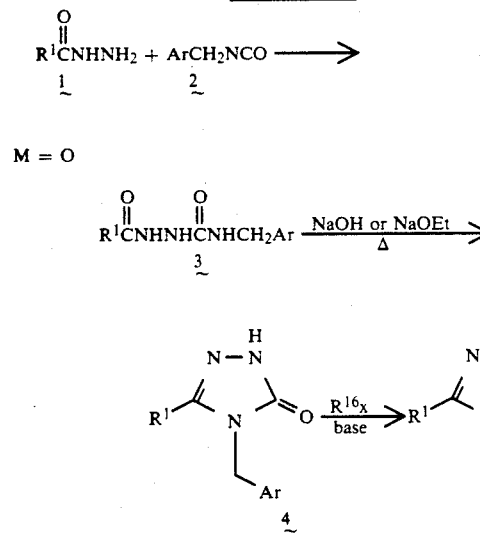

One of the most widely used routes to 2,4,5-trisubstituted-2,4-dihydro-3H-1,2,4-triazol-3-ones (2,4,5-trisubstituted-1,2,4-triazolin-3(4H)-ones) is shown in Reaction Scheme I-17 in its adaptation for the synthesis of compounds of Formula Ib. Reaction of a carboxylic acid hydrazide 1 (readily obtained from the corresponding ester) with the appropriate arylmethyl isocyanate 2 gives the 1-acyl-4-(arylmethyl)semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent $R^{16}Q$, where $R^{16}$ is alkyl, aralkyl, etc., and Q is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J. P. Yevich, U.S. Pat. No. 4,613,600 (1986), and (in part) H. Gehlen and W. Schade, *Liebigs Ann. Chem.*, 675, 180(1964), G. Palazzo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Beranek, *Collect. Czech. Chem. Commun.*, 50, 779 (1985).

REACTION SCHEME I-18

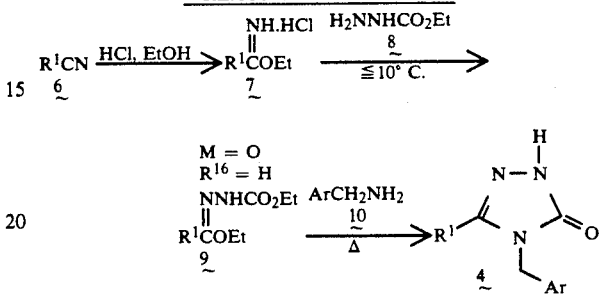

A highly useful alternative route to 4 is shown in Reaction Scheme I-18. This approach has been described by M. Pesson, S. Dupin, and M. Antoine, *Compt. Rend.*, 253, 285 (1961) and R. Un and A. Ikizler, *Chim. Acta Turc.*, 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°-150° C.). As in Reaction Scheme I-17, 4 can be alkylated to give the trisubstituted triazolinone 5.

REACTION SCHEME I-19

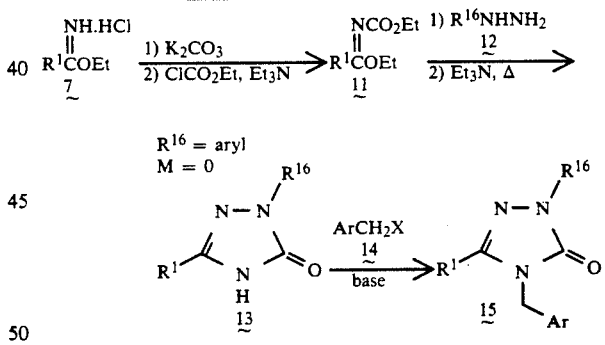

The procedures of Reaction Schemes I-17 and I-18 are not suitable for the introduction of most aryl or heteroaryl substituents at $N^2$. In contrast, the procedures of Reaction Schemes I-19 to I-22 are especially well suited for the synthesis of compounds of Formula Ib having aryl or heteroaryl substituents at $N^2$, since the triazolinone ring is constructed with the $N^2$-substituent in place, whereas the $N^4$-substituent is introduced subsequently by alkylation. Reaction Scheme I-19 presents a route patterned after that reported by K. Yabutani, K. Taninaka, M. Kajioka, K. Takagi, H. Matsui, K. Sutoh, and M. Yamamoto, European Patent Application 220, 952 (1987). The N-carbethoxy imidate 11 (obtained by reaction of 7 with ethyl chloroformate) is treated with an arylhydrazine 12 (or analog), typically at about 40°-50° C.,) in the presence of a tertiary amine such as triethylamine which effects cyclization to the triazolinone 13. In the presence of a suitable base (e.g., sodium hydride, sodium alkoxide, sodium hydroxide) treatment of 13 with the appropriate ArCH$_2$Q, where Q=bromo, iodo, chloro, methane-sulfonate, p-toluenesulfonate, and the like, yields the N$^4$-alkylated product 15. A variant of the method using a thioimidate has been described by M. Kajioka, H. Kurono, K. Okawa, and M. Harada, U.S. Pat. No. 4,318,731 (1982).

REACTION SCHEME I-20

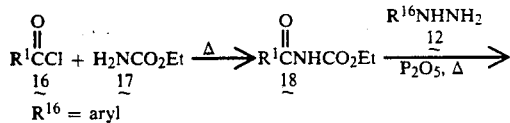

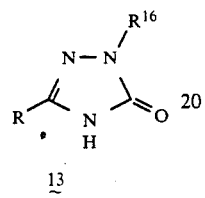

An alternative route to the N$^2$-substituted triazolinone intermediate 13 is shown in Reaction Scheme I-20. This chemistry has been described by T. N. Ghosh and M. V. Betrabet, *J. Indian Chem. Soc.*, 7, 899 (1930), S. Bellioni, *Ann. Chim. (Rome)*, 52, 187(1962), G. Palazzo and G. Picconi, *Boll. Chim. Farm.*, 105, 217 (1966), and British Patent 1,021,070 (1966). An acid chloride 16 is heated with urethane (17) (typically at 80°–100° C.), to give the acylurethane 18. Reaction of 18 with an arylhydrazine 12 and phosphorus pentoxide (usually in toluene or xylene at reflux) gives 13, which can then be further alkylated on N$^4$ as in Reaction Scheme I-19. A (thioacyl)urethane modification of this pathway has been reported by D. L. Temple, Jr., and W. G. Lobeck, Jr., U.S. Pat. No. 4,487,773 (1984).

REACTION SCHEME I-21

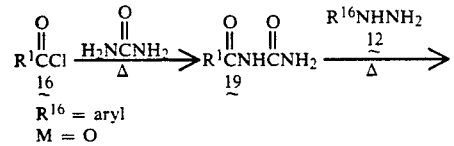

-continued
REACTION SCHEME I-21

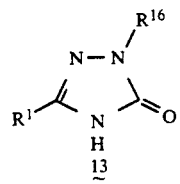

A variation of Reaction Scheme I-20, shown in Reaction Scheme I-21, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°–200° C.) is converted to the triazolinone intermediate 13.

REACTION SCHEME I-22

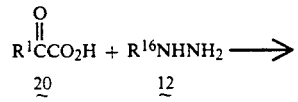

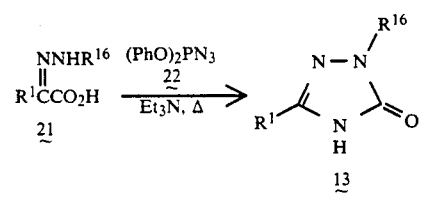

R$^{16}$ = aryl
M = O

In a quite different approach (Reaction Scheme I-22), L. Maravetz, U.S. Pat. No. 4,705,557 (1987) and G. Theodoridis, International Patent Application WO87/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°–115° C.). In the last step, an intermediate acyl azide loses nitrogen and undergoes the Curtius rearrangement to an isocyanate, which undergoes ring closure. As shown in Reaction Scheme I-19, 13 can then be alkylated on N$^4$ to give the trisubstituted triazolinone 15.

REACTION SCHEME I-23

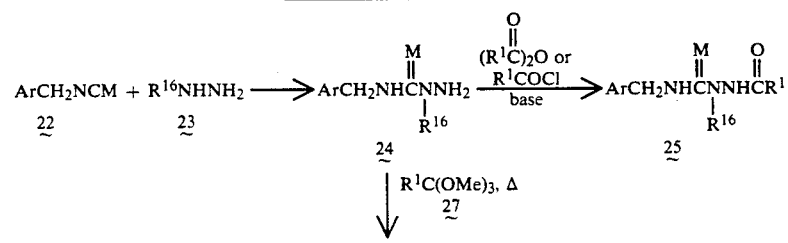

REACTION SCHEME I-23

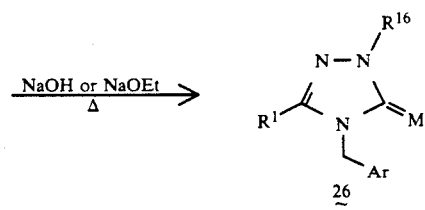

M = O or S 2,4,5-Trisubstituted-2,4-dihydro-3H-1,2,4-triazole-3-thiones (2,4,5-trisubstituted-1,2,4-triazolin-3(4H)-thiones) cannot generally be prepared by routes analogous to those in Reaction Schemes I-17 to I-22 because of the propensity for alkylation to occur on sulfur rather than on the open ring nitrogen. It is thus preferable to have all of the substituents in place at the time of the ring closure to form the heterocycle. As shown in Reaction Scheme I-23, for certain $R^{16}$ groups (e.g., $R^{16}=CH_3$), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

REACTION SCHEME I-24

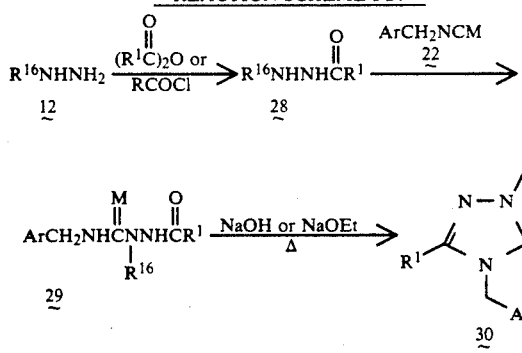

$R^{16}$ = aryl

In Reaction Scheme I-24, acylation of an aryl- or heteroaryl hydrazine gives 28, which can be reacted with the isocyanate or isothiocyanate 22 to yield the 1-acyl-2,4-disubstituted-semicarbazide or -thiosemicarbazide 29. Cyclization of 29 upon heating with hydroxide or alkoxide affords the triazolinone or triazolinethione 30. This chemistry has been described by H. Gehlen and W. Schade, *Liebigs Ann. Chem.*, 675, 180 (1964).

REACTION SCHEME I-25

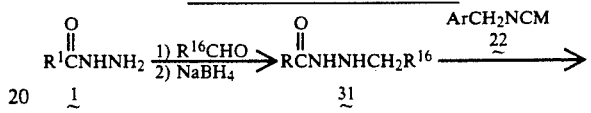

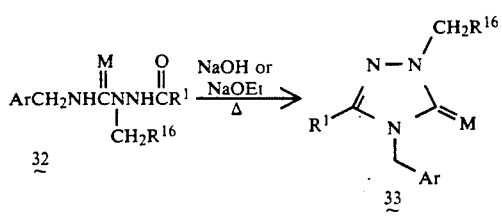

$R^{16}$ = aryl

The method of F. Russo, M. Santagati, and G. Pappalardo [*Ann. Chim. (Rome)*, 62, 351 (1972)](Reaction Scheme I-45) is useful for the synthesis of trisubstituted triazolinones and triazolinethiones having benzylic substituents at $N^2$. Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

REACTION SCHEME I-26

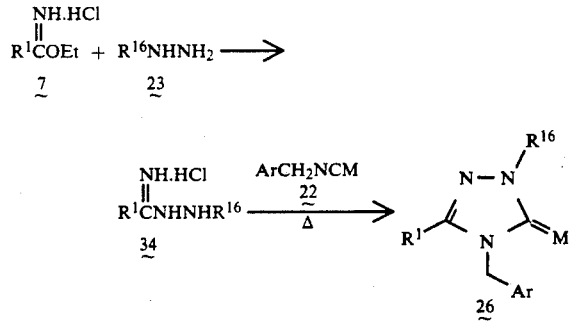

M = O or S

In another approach (Reaction Scheme I-26), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.*, 37, 293 (1980); T. Bany, *Rocz. Chem.*, 42, 247 (1968); and, T. Bany and M. Dobosz, *Ann. Univ. Mariae Curie-Sklodowska, Sect. AA*, 26/27, 23 (1971).

REACTION SCHEME I-27

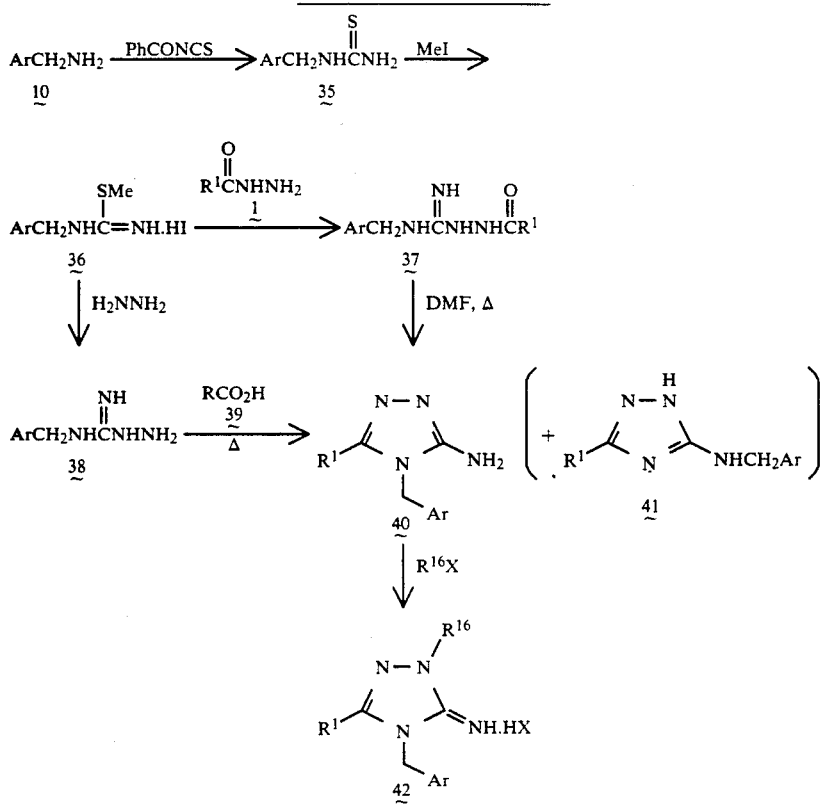

A route to 2,4,5-trisubstituted-2,4-dihydro-3H-1,2,4-triazol-3-imines (2,4,5-trisubstituted-1,2,4-triazolin-3(4H)-imines) is outlined in Reaction Scheme I-27. Reaction of the (arylmethyl)amine 10 with benzoyl isothiocyanate (or by other means) gives the substituted thiourea 35, which is methylated to prepare the isothiourea derivative 36. Compound 36 can be transformed to the acylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate Ar—CH$_2$—Q (where Q is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

REACTION SCHEME I-28

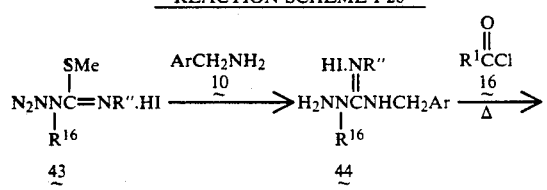

-continued
REACTION SCHEME I-28

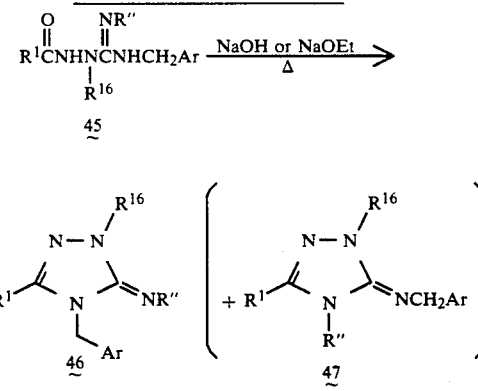

The route shown in Reaction Scheme I-28 utilizes chemistry reported by E. Akerblom, *Acta Chem. Scand.*, 19, 1135 (1965). The substituted isothiourea 43 is treated with amine 10 to give the aminoguanidine derivative 44. Acylation of 44 with the acid chloride 16 provides the intermediate 45, which can be cyclized by heating with hydroxide or alkoxide. The desired triazolinimine 46 is separated from the isomeric product 47.

C. Preparation of Pyrimidinones (Formula Ic)

The compounds of Formula Ic wherein either $J^2$ or $K^2$ is —C(O)— are synthesized as illustrated in Schemes I-49 to I-60 below.

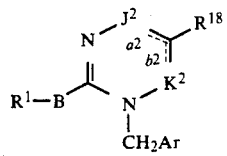

Pyrimidinones of formula Ic (wherein $J^2$ is —C(O)—) substituted in the 1,2,5, and 6-positions may be synthesized as shown in Scheme I-29. Amidines with an $R^1$ substituent may be reacted with a β-carbonyl ester to give a 4-hydroxypyrimidine. Conversion of the hydroxy group to a chloride then to an amine can be achieved by first treating the 4-hydroxypyrimidine with $POCl_3$ then with ammonia.[1] Reaction of the 4-aminopyrimidine with the appropriate alkyl halide followed by treatment with aqueous hydroxide gives the substituted pyrimidin-4(1H)-one.

SCHEME I-29

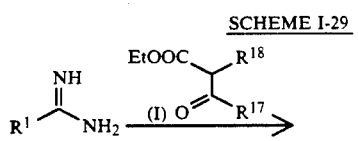

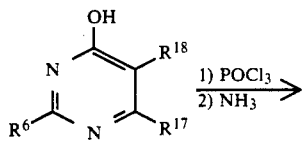

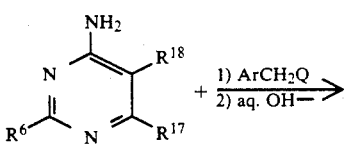

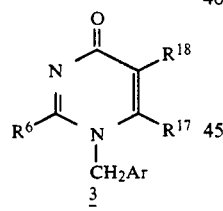

Q is leaving group (—Cl, —Br, —I, —OTs, etc.)

Scheme I-30 provides the method by which the isomeric (wherein $K^2$ is —C(O)—) 2,3,5, and 6-substituted pyrimidinones may be synthesized. A β-carbonyl ester is converted into its corresponding β-aminocrotonate with ammonia.[3] This is then acylated with an $R^1$-containing acyl chloride ($R^1COCl$) and cyclized to 3,1-oxazin-4-one. When the 3,1-oxazin-4-one is reacted with the substituted benzylamine, the desired fully substituted pyrimidinone 4 results.[4]

SCHEME I-30

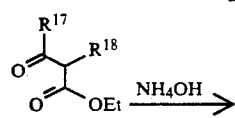

-continued
SCHEME I-30

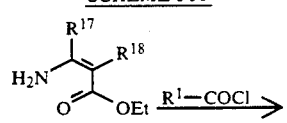

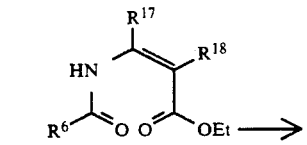

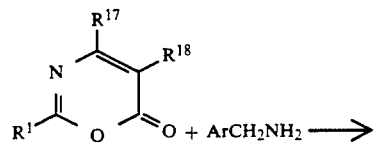

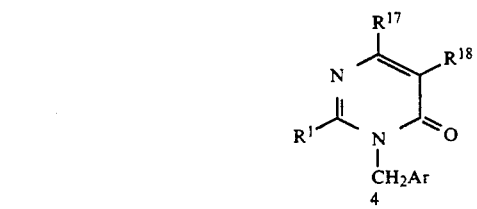

Alternatively, Scheme I-31 shows how an $R^6$ imidate may be converted to an amidine with the substituted benzylamine, followed by treatment with an appropriately substituted β-carbonyl ester to give the desired pyrimidinone 4.[5]

SCHEME I-31

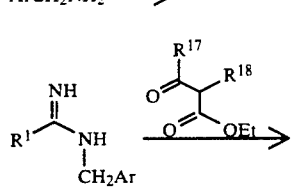

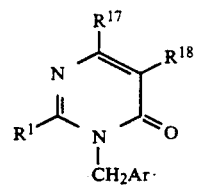

A third alternative is illustrated in Scheme I-52. A simple amidine can be reacted with an appropriately substituted β-carbonyl ester to give the 3-unsubstituted pyrimidinone. This can then be alkylated at the 3-position with KOH in methanol (or with NaH in DMF) and the appropriately substituted alkyl halide to give 4.

SCHEME I-32

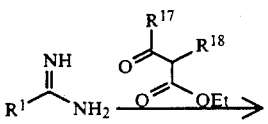

-continued
SCHEME I-32

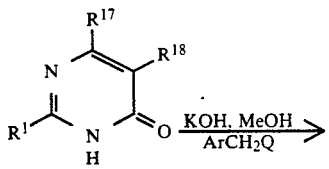

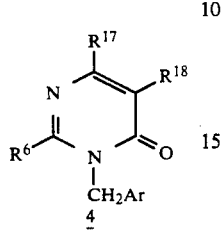

Scheme I-33 illustrates the general synthesis of pyrimidinones of Formula Ic in which B is a sulfur atom. Thiourea when condensed with a β-carbonyl ester gives the 2-thiouracil. This can be bis-trimethylsilylated using hexamethyldisilazane, then alkylated sequentially on the 1-nitrogen atom and then on the sulfur atom using chemistry developed by H. Vorbruggen and P. Strehlke.[6] By this method, one can then obtain compounds of Formula Ic wherein $J^2$ is —C(O)— and B is a sulfur atom.

SCHEME I-33

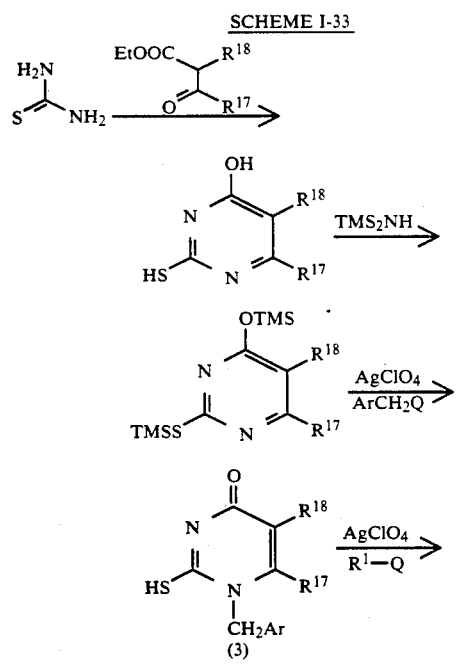

Q is Br, Cl, I, F, OTs, OTf, etc.

The isomeric 2,3-dialkylated thiouracils may be synthesized as shown in Scheme I-34. Thiourea can be condensed with an appropriately substituted β-carbonyl ester to give the 5,6-disubstituted-2-thiouracil.[7] This may then be alkylated sequentially at the sulfur with an $R^1$ halide, and then at the nitrogen atom with an appropriately substituted alkyl halide to give the desired tetrasubstituted pyrimidinone 4.

SCHEME I-34

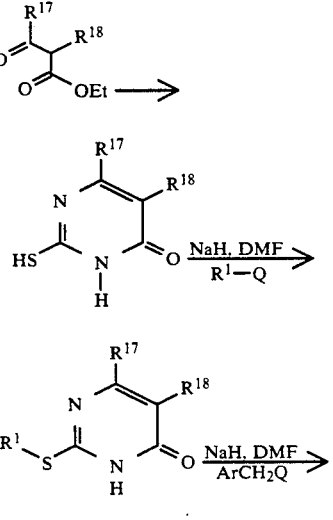

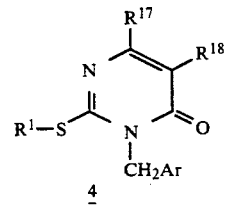

Alternatively, as illustrated in Scheme I-35, an isothiocyanate can be converted into a thiourea by the addition of ammonia.[8] This can then be condensed with the appropriately substituted β-carbonyl ester to give the 3,5,6-trisubstituted-2-thiouracil.[9] Alkylation at the sulfur atom with base and an $R^1$ halide then gives the desired pyrimidinone 4.

SCHEME I-35

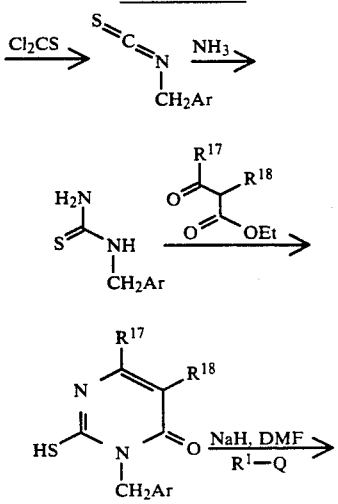

-continued
SCHEME I-35

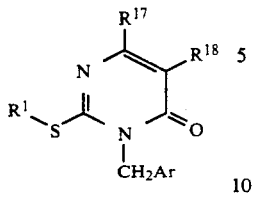

Scheme I-36 provides a method by which the 2-alkoxy-1-alkylpyrimidinones may be synthesized. An appropriately substituted β-keto amide[10] is cyclized with carbonyl diimidazole[11] and converted to the corresponding uracil upon treatment with the appropriately substituted primary amine.[12] The uracil can then be converted to the 2-alkoxy-1-alkylpyrimidinone by treatment with an R[1] orthoester.[13] Alternatively, Scheme I-37 shows how the methods of Wittenburg[14] might be employed to accomplish the same transformation.

SCHEME I-36

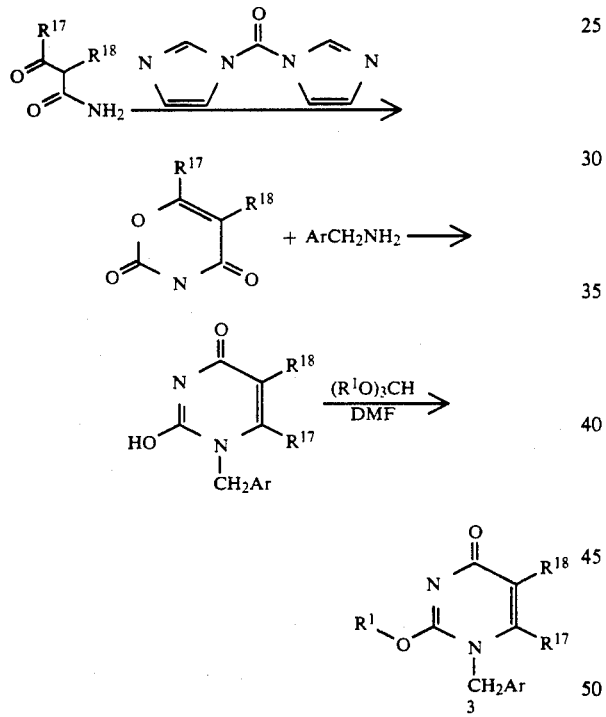

SCHEME I-37

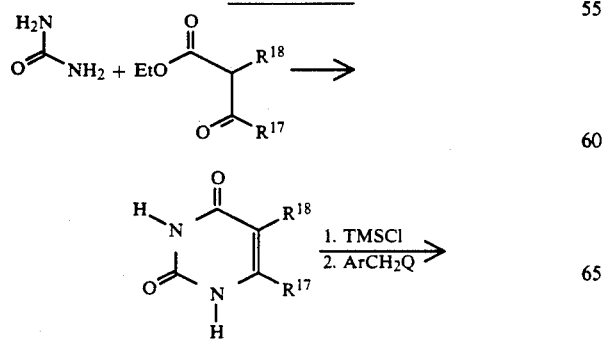

-continued
SCHEME I-37

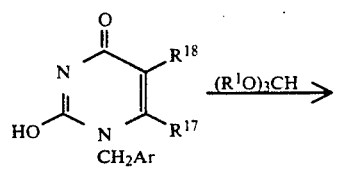

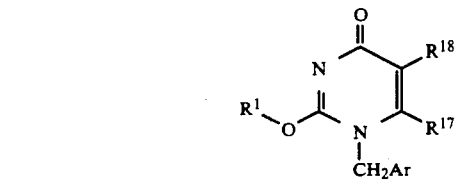

Scheme I-38 shows how the isomeric 2-alkoxy-3-alkylpyrimidinones can be prepared. The primary amine can be converted into an isocyanate[15], then converted to the corresponding urea by treatment with ammonia. Reaction of the urea with an appropriately substituted β-keto ester then gives the 3-substituted uracil.[16] Conversion of the uracil to the corresponding 2-alkoxy pyrimidinone is achieved using an R[1] orthoester.[17] Alternatively, a β-aminocrotonate can be reacted with the isocyanate, as shown in Scheme I-39[18], then alkoxylated with an R[1] orthoester.

The β-keto esters used in the preceding schemes can be synthesized readily from ethyl hydrogen malonate and an R[17] acid chloride as shown in Scheme I-40.[19] R[17] may be alkyl or aryl. Alkylation of this material with an alkyl halide (R[18]-Q) is achieved using sodium hydride in DMSO or by other classical methods. R[18] may be alkyl or aralkyl suitably protected, if necessary, so as not to react with NaH.

Scheme I-41 illustrates the preparation of the 5-alkoxycarbonyl moiety and the corresponding 5-amino derivatives.

SCHEME I-38

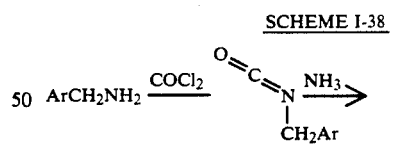

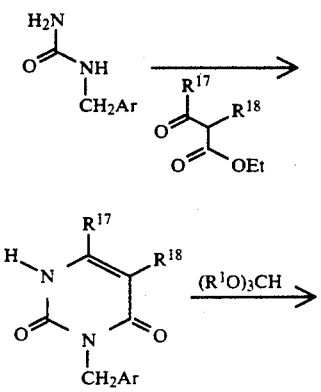

-continued
SCHEME I-38

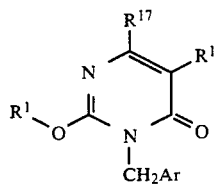

SCHEME I-39

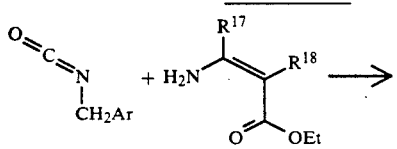

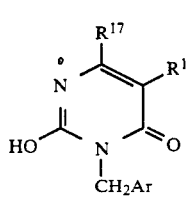

SCHEME I-40

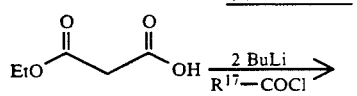

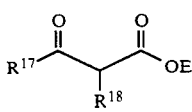

SCHEME I-41

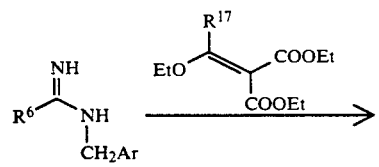

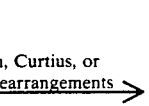

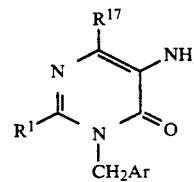

1. K. Wunsch, A. J. Boulton, *Adv. Het. Chem.* (1967), 8, 326-9 and references therein.
2. D. J. Brown, E. Hoerger, S. F. Mason, *J. Chem. Soc.* (1955) 4035.
3. V. Prelog, et al, *Ber.* (1945) 28 1684.
4. H. B. Kagan, M. Y. H. Suen, *Bull. Soc. Chim. Fr.* (1966) 1819. W. Steglich, E. Buschmann, O. Hollitzer, *Angew. Chem Int. Ed. Engl.* (1974) 13 533. F. Eiden, B. S. Nagar, *Naturwissenschaften* (1963) 50 43. A. Krantz, B. Hoppe, *J. Am. Chem. Soc.* (1975) 97 6590.
5. A. Sitte, H. Paul, *Chem. Ber.* (1969) 102 615.
6. H. Vorbruggen, P. Strehlke, *Chem. Ber.* (1973) 106 3039.
7. D. J. Brown, The Pyrimidines, (1962), J. Wiley & Sons, p. 300.
8. D. J. Brown, The Pyrimidines, (1962), J. Wiley & Sons, P. 437.
9. R. G. Dave, G. S. Mewada, G. C. Amin, *J. Ind. Chem. Soc.* (1960) 37 595. M. Sano, *Chem. Pharm. Bull.* (1962) 10 313. C. Piantadosi, V. G. Skulason, J. L. Irvin, J. M. Powell, L. Hall, *J. Med. Chem.* (1964) 7 337. 10. M. K. Jain, *Ind. J. Chem.* (1963) 1 274. P. C. Kuzma, L. E. Brown, T. M. Harris, *J. Org. Chem.* (1984) 49 2015.
11. S. De Bernardo, M. Weigele, *J. Org. Chem.* (1977) 42 109.
12. T. Kinoshita, H. Tanaka, S. Furukawa, *Chem. Pharm. Bull.* (1986) 34 1809.
13. F. Yoneda, T. Nagamatsu, M. Takamoto, *Chem. Pharm. Bull.* (1983) 31 344.
14. Wittenburg, *Angew. Chem.* (1965) 77 1043.
15. S. Ozaki, *Chem. Rev.* (1972) 72 457.
16. Gabriel, Colman, *Ber.* (1904) 37 3657.
17. F. Yoneda, T. Nagamatsu, M. Takamoto, *Chem. Pharm. Bull.* (1983) 31 344.
18. R. Behrend, F. C. Meyer, Y. Buckholz, *Liebigs Ann. Chem.* (1901) 314 200.
19. W. Wierenga, H. I. Skulnick, *Org. Syn.* (91983) 61, 5.

PART II: Preparation of nitrogen containing phenyl derivatives and coupling to the heterocycle described in Part II Alkylating agents of type 2a, where $Z^1$ represents a precursor or a protected form of Z, can be prepared by treatment of tolyl derivatives of type 1 with under reaction conditions such as N-bromosuccinimide in the presence of a radical initiator such as dibenzoylperoxide (DBPO) or azo-bis-isobutyrylnitrile (AIBN). Alternatively, alcohols of type 3 can be converted to alkylating agents of type 2b by treatment with activating agents such as methanesulfonyl chloride (MsCl) or p-toluenesulfonyl chloride (TsCl), as described in Scheme II-1.

Tolyl derivatives of type 1 can be prepared by coupling heteroaryl halides or triflates (OTf) of type 5 with aryl zinc, magnesium, trialkyltin, boronic acids, or boronic esters of type 5 in the presence of catalysts such as bistriphenylphosphine nickel chloride or tetrakistriphenylphosphine palladium in solvents such as THF, or DMF. Alternatively, heteroaryl zinc, magnesium, trialkyltin, boronic acids, or boronic esters of type 6 can be coupled to aryl halides or triflates of type 7 in the above manner, see Scheme II-2.

SCHEME II-1

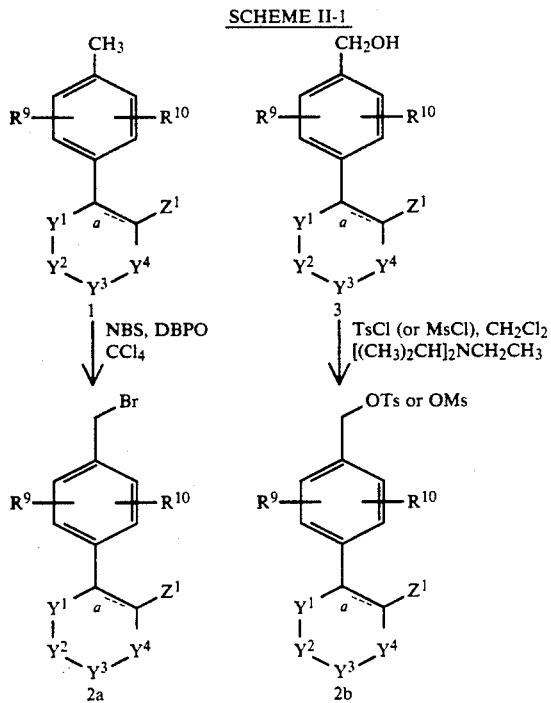

$Z^1$ = precursor or protected form of Z
a = a single or double bond

SCHEME II-2

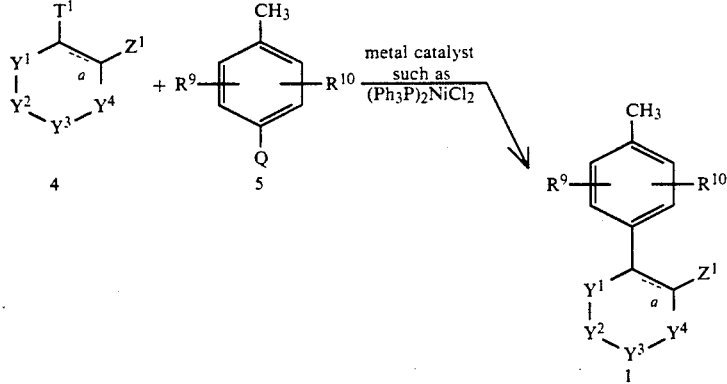

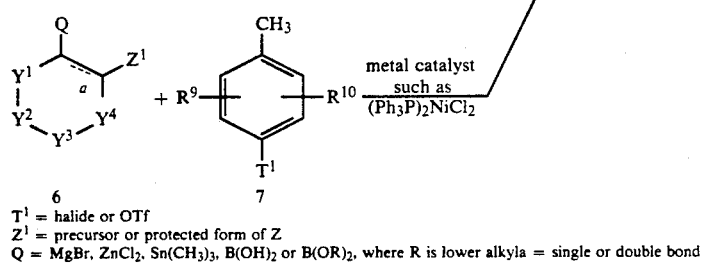

$T^1$ = halide or OTf
$Z^1$ = precursor or protected form of Z
Q = MgBr, ZnCl$_2$, Sn(CH$_3$)$_3$, B(OH)$_2$ or B(OR)$_2$, where R is lower alkyl   a = single or double bond sulfonyl chlorides 12 which in turn are reacted with amines such as tert-butyl amine to give 13. Sulfonamides 11 and 13 can be converted into alkylating agents as described in Scheme II-1 and coupled to the appropriate heterocycle to give sulfonamide 14. Compounds of type 14 are then treated with trifluoroacetic acid then acylated to give acylsulphonamides 15.

SCHEME II-3

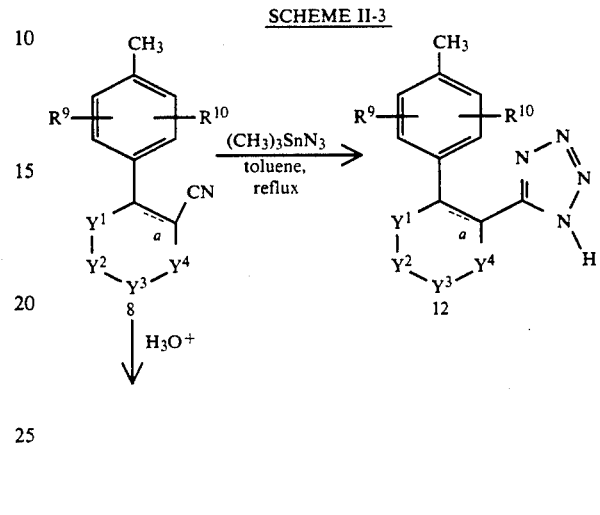

The group $Z^1$ of type 1 compounds can be further manipulated, as shown in Schemes II-3 and II-4, after biaryl coupling. Nitriles 8 can be converted into carboxylic acids 9 which in turn may undergo a Curtius rearrangement giving amines 10. Amines 10 may be converted to sulphonamides 11 or diazotized and reacted with SO$_2$ in the presence of CuCl to give intermediate -continued
SCHEME II-3

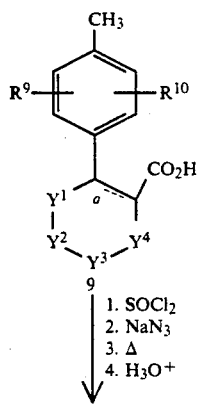

-continued
SCHEME II-3

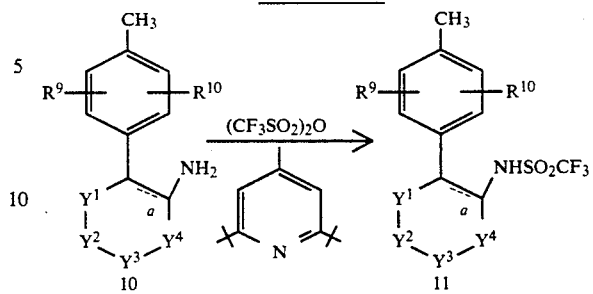

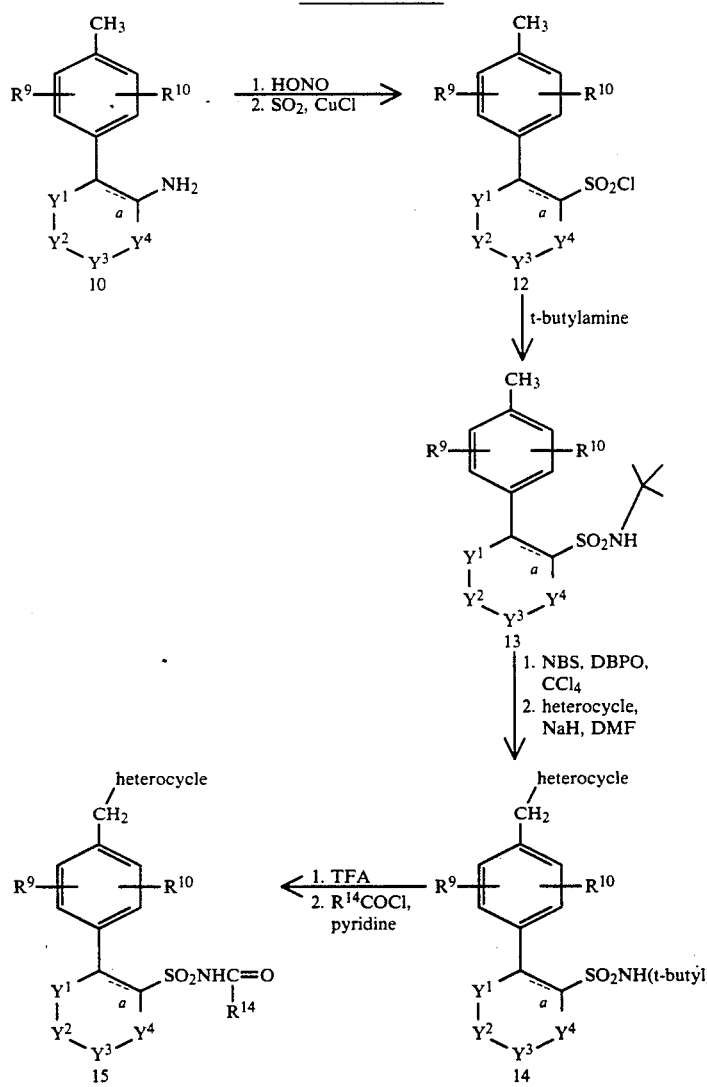

Scheme II-5 describes an alternative route from those described in Scheme II-2 for the preparation of tolyl derivatives of type 1, as well as exemplifying a route generally described in Scheme II-2. The coupling of the aryl and heteroaryl portions can be accomplished as exemplified by the preparation of 17 by reaction of pyridine 16 with phenyl chloroformate and p-tolylmagnesium bromide 17 in the presence of CuI, followed by aromatization of the dihydropyridine intermediate 18 with hot sulfur, to give the tolyl derivative 21. Alternatively, 4-bromotoluene 19, upon treatment with butyllithium and zinc chloride to generate the tolylzinc intermediate, which in the presence of a nickel catalyst and heteroaryl halide 20 gives the tolyl derivative 21.

Illustrative of one technique for the preparation of compounds of Formula I from alkylating agents of type 2a and 2b is the conversion of 21 to bromide 22, shown in Scheme II-5, followed by alkylation with heterocycle 23. Alkylation is typically accomplished by treatment of the heterocycle with sodium hydride in DMF to give the sodium salt exemplified by 24, which upon treatment with bromide 22 gives the cyano compound 25, as shown in Scheme II-6. Conversion of 25 to the tetrazole containing angiotensin II antagonist 26 is accomplished by reaction with trimethylstannyl azide, as shown in Scheme II-7. Preparation and conversion of 29 to AII antagonist 31 is shown in Scheme II-8.

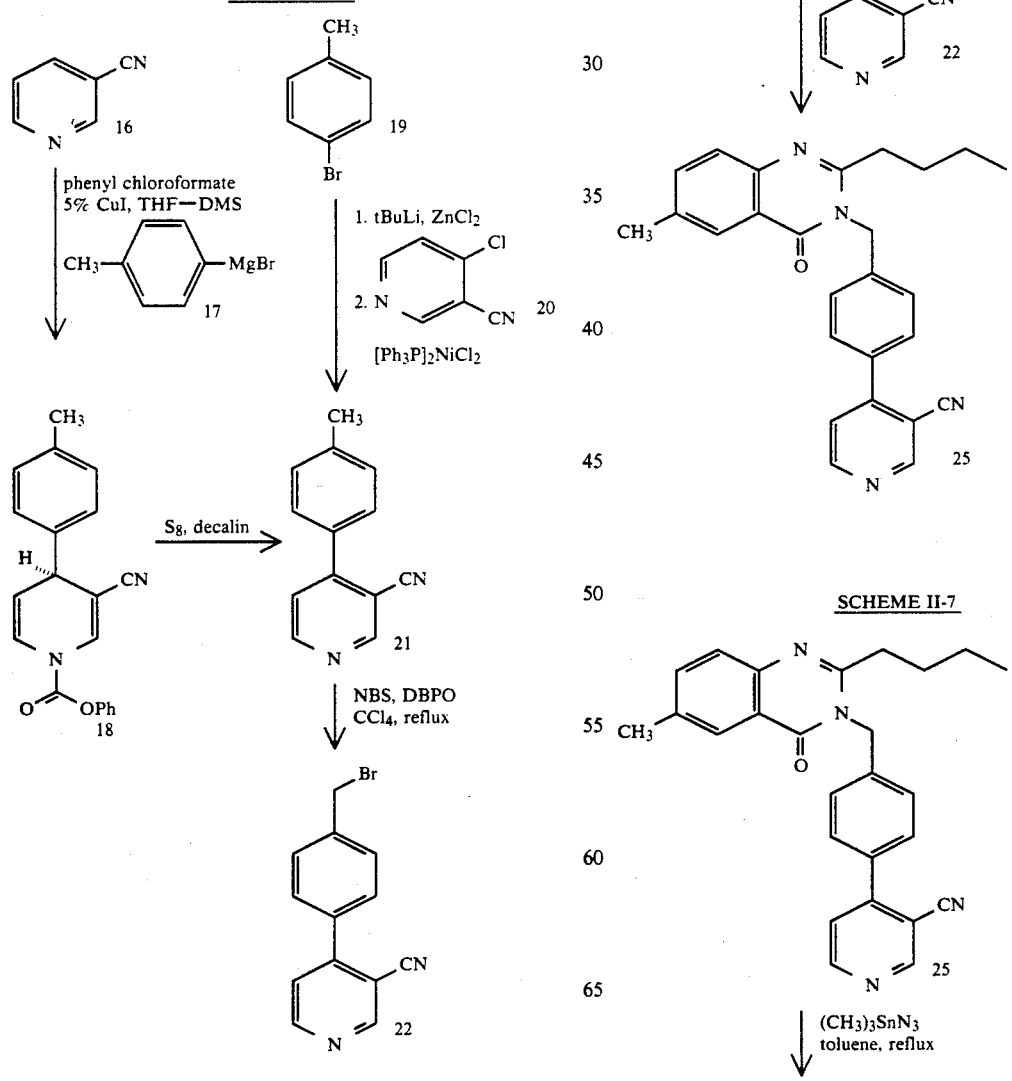

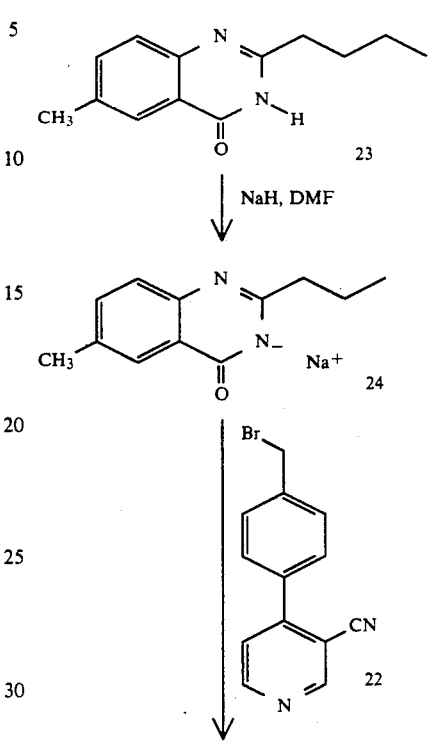

-continued
SCHEME II-7

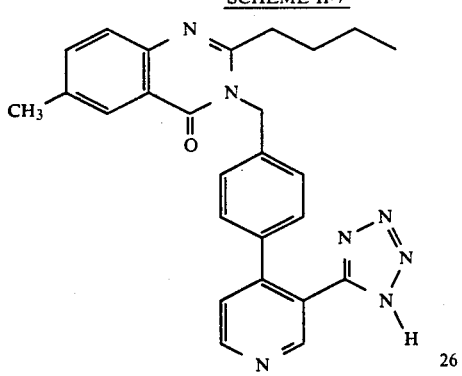

product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

SCHEME II-8

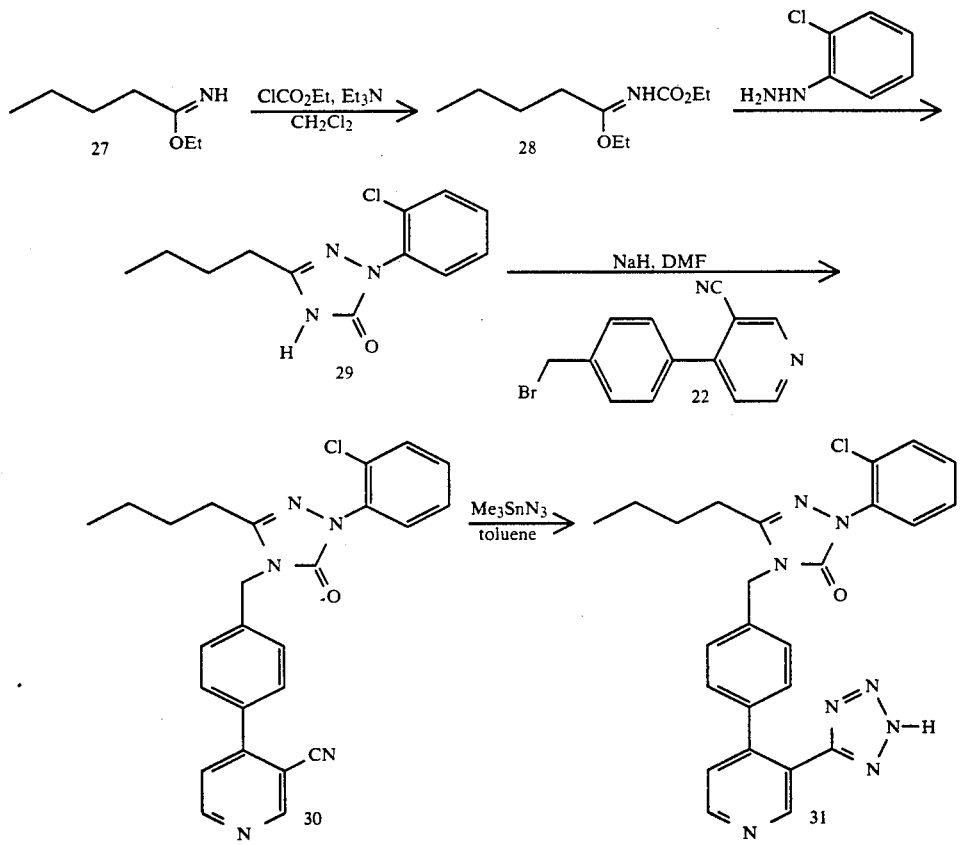

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the Three frozen rabbit aortae (obtained from Pel-Freeze Biologicals) were suspended in 5 mM Tris-0.25M Sucrose, pH 7.4 buffer (50 mL) homogenized, and then centifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}$I-Sar$^1$Ile$^8$-angiotensin II [obtained from New England Nuclear] (10 mL; 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a mesure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 mL) there was added $^3$H-angiotensin II (50 mM) (10 mL) with or without the test sample and the mixture was incubated at 37° C. for 1 hour. The mixture was then diluted with Tris buffer (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antogonists.

The potential antihypertensive effects of the compounds described in the present invention may be evaluated using the methodology described below: Male Charles River Sprague-Dawley rats (300-375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30 minute intervals and the increase in the diastolic blood pressure was recorded before and after drug or vehicle administration.

Using the methodology described above, representative compounds of the invention were evaluated and found to exhibit an activity of at least IC$_{50}$<50 mM thereby demonstrating and confirming the utility of the compounds of the invention as effective AII antagonists.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like.

Pharmaceutical formulations prepared to treat intraocular pressure would typically contain about 0.1% to 15% by weight, and preferably 0.5% to 2.0% by weight of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Preferably, the dosage range will be about 2.5 to 250 mg per patient per day; more preferably about 2.5 to 75 mg per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommeded levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg), chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus miloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 600 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended hereto.

PREPARATION OF 2-ALKYL-QUINAZOLIN-4(1H)-ONES

EXAMPLE 1

2-Butyl-6-methylquinazolin-4(1H)-one

To a solution of 3.0 g (20 mmol) of 2-amino-5-methylbenzoic acid in 20 mL of dry DMF at 0° C. was added 200 mg of DMAP followed by 6.07 g (60 mmol) of triethyl amine and 5.02 g (40 mmol) of valeryl chloride. The resulting mixture was stirred at 0° C. for 30 minutes. The mixture was heated to 110° C. and monitored by TLC for the formation of the intermediate quinoxazolone (rf=0.8, 40%EtOAc/hexane). Following complete formation of the intermediate 10 g (100 mmol) of $NH_4CO_3$ was added cautiously. Heating was continued to ensure consumption of the quinoxazolone and formation of the polar (rf=0.4, 40%EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystallized from MeOH to give 1.07 g (5 mmol) of a white crystaline solid. 25% yield overall. $^1$H-NMR (CDCl$_3$): 0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H). Anal ($C_{13}H_{16}N_2O$), C, H, N.

EXAMPLE 2

6-Methyl-2-propylquinazoline-4(1H)-one

The 2-propyl derivative was prepared in the identical fashion as the 2-butyl derivative through the use of butyryl chloride in place of valeryl chloride. The product was recrystallized from hexane/acetone to give white crystals. 32% yield. $^1$H-NMR (CDCl$_3$): 11.51 (bs, 1H), 8.08 (s, 1H), 7.60 (s, 2H), 2.78 (3 line m, 2H), 2.01 (s, 3H), 1.92 (m, 2H), 1.09 (t, 3H).

EXAMPLE 3

2-Butyl-7-methylquinazoline-4(1H)-one

Same procedure as in Example 1 with valeroyl chloride and 2-amino-4-methylbenzoic acid. The product was recrystallized from MeOH recovering 0.91 g (4.2 mmol). 21% yield overall. $^1$H-NMR (CDCl$_3$): 0.99 (t, 3H, J=7.4 Hz), 1.49 (m, 2H), 1.86 (m, 2H), 2.50 (s, 3H), 2.76 (t, 2H, J=7.81 Hz), 7.28 (d, 1H, J=8.3 Hz), 7.49 (s, 1H), 8.15 (d, 1H, J=8.3 Hz). Anal (C$_{13}$H$_{16}$N$_2$O), C, H, N.

EXAMPLE 4

2-Butyl-naphtho[2,3-e]quinazoline-4(1H)-one

Same procedure as in Example 1 with valeroyl chloride and 2-aminonapthoic acid. Product was recrystallized from MeOH. A contaminant co-crystallizes with the desired product. The contaminant is 25% of the product by $^1$H-NMR. Recovered 1.6 g (59% yield). $^1$H-NMR (CDCl$_3$): 0.97 (t, 3H, J=7.3 Hz), 1.42 (m, 2H), 1.75 (m, 2H), 2.48 (t, 2H, J=7.4 Hz), 7.42 (t, 1H, J=7.8 Hz), 7.54 (t, 1H, J=8.3 Hz), 7.77 (d, 1H, J=7.8 Hz), 7.82 (d, 1H, J=8.31 Hz), 8.07 (s, 1H), 9.08 (s, 1H), 10.89 (bs, 1H).

EXAMPLE 5

2-Butyl-5-methylquinazoline-4(1H)-one

Same procedure as in Example 1 with valeroyl chloride and 2-amino-6-methylbenzoic acid on a 16 mmol scale. The concentrated reaction mixture was diluted with 50 mL ether and 50 mL H$_2$O. The mixture was agitated for several minutes and then filtered in vacuo. On filtration further crystalline material formed in the filtrate. The filtrate was filtered again. This procedure was repeated a further two times. The precipitates were collected and combined. The ethereal phase was decanted from the aqueous phase, and concentrated to 15 mL. 25 mL of hexanes was then added and the mixture filtered. The combined precipitates were recrystallized from MeOH/H$_2$O to give 0.73 g (3.37 mmol) of fluffy white crystals. 21% yield. $^1$H-NMR (CDCl$_3$): 0.98 (t, 3H, J=7.38 Hz), 1.48 (m, 2H), 1.87 (m, 2H), 2.75 (dd, 2H, J=8.09 Hz), 2.89 (s, 3H), 7.20 (d, 1H, J=6.73 Hz), 7.56 (m, 2H), 11.68 (bs, 1H).

EXAMPLE 6

2-Butyl-6,8-dimethylquinazoline-4(1H)-one

Same procedure as in Example 1 with valeroyl chloride and 2-amino-5,8-dimethylbenzoic acid on a 12 mmol scale. The product collected from filtration of the ether/water mixture was recrystalized from MeOH. $^1$H-NMR and TLC indicated that the product isolated was a 50% mixture of the desired quinazoline and a contaminant. An aliquot of 0.5 g of this material was concentrated onto 5 mL of flash silica and applied to the surface of a flash chromatography column. The column was eluted with 60% EtOAc/hexanes. The first eluted compound (0.14 g) was collected as a TLC homogeneous sample of the desired product. $^1$H-NMR (CDCl$_3$): 0.99 (t, 3H, J=7.32 Hz), 1.48 (m, 2H), 1.85 (m, 2H), 2.44 (s, 3H), 2.58 (s, 3H), 2.75 (dd, 2H, J=7.87, 7.87 Hz), 7.43 (s, 1H), 7.91 (s, 1H), 10.70 (bs, 1H).

EXAMPLE 7

2-Butyl-8-methylquinazoline-4(1H)-one

Same procedure as in Example 1 with valeroyl chloride and 2-amino-6-methylbenzoic acid on a 1 mmol scale. The concentrated reaction mixture was diluted with 20 mL ether/20 mL H$_2$O. The mixture was filtered. The ethereal phase was seperated, dried (MgSO$_4$), filtered and concentrated. The residue was flash chromatographed over silica eluting with 50% EtOAc/hexanes to give rise to 48 mg (0.22 mmol) of a fluffy yellow solid. 22% yield. $^1$H-NMR (CDCl$_3$): 1.02 (t, 3H), 1.52 (m, 2H), 1.88 (m, 2H), 2.62 (s, 3H), 2.79 (dd, 2H), 7.35 (dd, 1H), 7.61 (d, 1H), 8.12 (d, 1H). FABMS: 217 (M+ +1) calc for C$_{13}$H$_{16}$N$_2$O.

EXAMPLE 8

2-Butyl-6-isopropylquinazolin-4(1H)-one

Same procedure as in Example 1 with valeroyl chloride and 2-amino-5-isopropylbenzoic acid on a 16 mmol scale. The concentrated reaction mixture was partitioned between 20 mL water and 20 mL of ether. A fine white precipitate was removed by filtration and recrystallized from MeOH/water. The first crop gave rise to 0.56 g of fluffy white crystals. $^1$H-NMR (CDCl$_3$): 0.99 (t, 3H, J=7.3 Hz), 1.32 (d, 6H, J=6.89 Hz), 1.48 (m, 2H), 1.85 (m, 2H), 2.77 (3 line m, 2H, J=7.9 Hz), 3.06 (m, 1H), 7.65 (m, 2H), 8.11 (s, 1H), 11.22 (bs, 1H). FABMS: 245 (M+ +1) calc for C$_{15}$H$_{20}$N$_2$O.

EXAMPLE 9

2-Butyl-6-thiomethylquinazolin-4(1H)-one

Same procedure as that described in Example 1. However on addition of ether/water to the reaction mixture a precipitate of the quinazolinone was not formed. The aqueous phase was extracted with ether and the combined ethereal extracts were washed with brine and dried over MgSO$_4$. The mixture was filtered and concentrated in vacuo to give a mixture of the desired product and 2-(N-valeroyl-amino)-5-thiomethylbenzamide. This mixture was heated with 2 equivalents of 1N NaOH solution in water at 100° C. until a clear solution was obtained. The solution was cooled, acidified, and filtered to give a pale yellow precipitate. The product was recrystalized from MeOH to give a 73% overall yield of the title compound. $^1$H-NMR (CDCl$_3$-300 MHz): 1.00 (t, 3H, J=7.3 Hz), 1.50 (m, 2H), 1.86 (m, 2H), 2.58 (s, 3H), 2.76 (3 line m, 2H, J=7.9 Hz), 7.62 (m, 2H), 8.03 (d, 1H, J=1.9 Hz), 11.11 (bs, 1H).

EXAMPLE 10

2-Butyl-6-nitroquinazolin-4(1H)-one

To a mixture of 326 mg (2 mmol) of 2-cyano-4-nitroaniline in 10 mL of CH$_2$Cl$_2$ at 0° C. was added 0.34 mL (2.4 mmol) of triethylamine and 25 mg of DMAP. To this mixture was added 0.26 ml of valeryl chloride dropwise. The reaction mixture was allowed to warm to room temperature over 1.5 hours and then concentrated in vacuo. The residue was dissolved in 40 ml of EtOAc and washed with 25 ml of water, 25 ml of saturated NaHCO$_3$ and 25 ml of brine. The organic phase was dried over Na$_2$SO$_4$, filtered and concentrated. The residue (0.46 g) was purified by flash chromatography. The residue was absorbed onto 0.6 g of silica which was applied to the surface of a 5.5"×0.75" silica flash chromatography column. The product was eluted with 20%

EtOAc/hexanes to give 0.21 g of N-valeryl-2-cyano-4-nitro-anilide (44% yield). 0.1 g (0.42 mmol) of the amide was dissolved in 1.5 mL of MeOH. To this solution was added 138 μL of a 30% hydrogen peroxide solution followed by 330 μL of a 3N NaOH solution. The solution was refluxed for 1.5 hours, cooled and concentrated in vacuo. The residue was dissolved in 10 mL of water. Dropwise addition of a saturated solution of NH$_4$Cl caused the product to precipitate out as 90 mg (0.36 mmol) of a yellow powder. (87% yield. $^1$H-NMR (CDCl$_3$): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

EXAMPLE 11

2-Butylquinazolin-4(1H)-one

To a solution of 500 mg 2-aminobenzonitrile (4.23 mmol), 514 mg triethylamine (5.08 mmol), and 50 mg DMAP (0.41 mmol) in 6 mL CH$_2$Cl$_2$ at 0° C. was added 562 mg valeryl chloride (4.66 mmol) dropwise over 1 minute. The mixture was warmed to room temperature and stirred for twenty minutes. The mixture was then diluted with water and brine and then was extracted three times with ether. The combined organic material was dried over MgSO$_4$, stripped of solvent in vacuo, and was purified by flash chromatography eluting with 20% ethyl acetate in hexane to give 2-valerylamidobenzonitrile. R$_f$ 0.22 in 20% ethyl acetate in hexane. $^1$H-NMR (300 MHz, CDCl$_3$): 8.42 (d, 1H), 7.60-7.10 (m, 2H), 6.72 (m, 1H), 4.40 (br s, 1H), 2.46 (t, 2H), 1.74 (m, 2H), 1.43 (m, 2H), 0.97 (t, 3H).

To a solution of 5.1 g of the amide in 90 mL methanol were added 21 mL 3N NaOH and 10 ml 30% H$_2$O$_2$ at room temperature. The mixture was refluxed for 30 minutes and concentrated in vacuo. Water and sat. NH$_4$Cl was added and the mixture extracted 3 times with ether. The combined organic extracts were dried over MgSO$_4$, filtered and concentrated in vacuo and the residue was recrystallized from hexane/acetone to give two crops of the product as white needles. 2.2 g, 43% yield. R$_f$ 0.16 in 20% EtOAc in CH$_2$Cl$_2$. $^1$H-NMR (CDCl$_3$): 8.29 (m, 1H), 7.81-7.68 (m, 2H), 7.47 (m, 1H), 2.79 (3 line m, 2H), 1.87 (m, 2H), 1.51 (m, 2H), 1.00 (t, 1H).

EXAMPLE 12

6-Bromomethyl-2-butylquinazolin-4(1H)-one

To a suspension of 2.6 g (12 mmol) of the product of Example 2 in 100 mL of dry CCl$_4$ was added 2.56 g of N-bromosuccinimide followed by 200 mg of benzoyl peroxide. The reaction mixture was heated to reflux for 45 minutes at which time a precipitate formed throughout. The reaction mixture was concentrated in vacuo and the residue partitioned between 150 mL of EtOAc and 100 mL of water. The mixture was shaken and then filtered to give 1.59 g of the title compound (45% yield). The filtrate was separated into two phases and the organic phases was washed with 75 mL of sat. NaHCO$_3$ solution followed by 75 mL of water and 75 mL of brine. The organic phase was dried over MgSO$_4$, filtered and the filtrate was concentrated in vacuo. The residue was purified by recrystalization from EtOAc to give 0.52 g (1.76 mmol) of the same product as was recovered above. Total yield 60%. $^1$H-NMR (CDCl$_3$): 1.00 (t, 3H, J=7.33 Hz), 1.49 (m, 2H), 1.84 (m, 2H), 2.77 (3 line m, 2H, J=7.7 Hz), 4.61 (s, 2H), 7.68 (d, 1H, J=8.4 Hz), 7.80 (dd, 1H, J=8.4, 2.1 Hz), 8.27 (d, 1H, J=2.1 Hz), 11.02 (bs, 1H).

EXAMPLE 13

5-Bromomethyl-2-butylquinazolin-4(1H)-one

The product of Example 5 was treated as in Example 13 to give a 71% yield of a white solid. $^1$H-NMR (CDCl$_3$): 1.0 (t, 3H, J=7.3 Hz), 1.53 (m, 2H), 2.90 (m, 2H), 2.81 (3 line m, 2H, J=7.98 Hz), 5.31 (s, 2H), 7.45 (m, 1H), 7.71 (m, 2H), 11.28 (bs, 1H).

EXAMPLE 14

6-Acetoxymethyl-2-butylquinazolin-4(1H)-one

To a solution of 2.1 g (7.0 mmol) of the quinazolinone prepared in Example 12 in 15 mL of dry DMF was added 1.74 g (20.0 mmol) of sodium acetate. The mixture was heated to 60° C. for 3 hours. The reaction mixture was concentrated in vacuo and the residue dissolved in 100 mL of CH$_2$Cl$_2$. The solution was washed with water (3×20 mL), brine (1×20 mL) and dried over MgSO$_4$. The mixture was filtered and concentrated in vacuo. The residue was recrystallized from MeOH/H$_2$O to give 1.31 g (4.8 mmol) of a colorless solid. 68% yield. $^1$H-NMR (CDCl$_3$): 0.99 (t, 3H, J=7.32 Hz), 1.50 (m, 2H), 1.83 (m, 2H), 2.14 (t, 3H), 2.77 (3 line m, 2H, J=7.71 Hz), 5.23 (s, 2H), 7.69-7.78 (m, 2H), 8.25 (s, 1H), 10.90 (bs, 2H).

EXAMPLE 15

5-Acetoxymethyl-2-butylquinazolin-4(1H)-one

The product of Example 13 was treated as in Example 14 to give after recrystallization from EtOAc a 77% yield of the desired acetylated product. $^1$H-NMR (CDCl$_3$): 0.98 (t, 3H, J=7.38 Hz), 1.50 (m, 2H), 1.88 (m, 2H), 2.19 (s, 3H), 2.77 (3 line m, 2H, J=7.93 Hz), 5.85 (s, 2H), 7.48 (m, 1H), 7.70 (m, 2H), 11.65 (bs, 1H).

EXAMPLE 16

6-Nitro-2-propylquinazolin-4(1H)-one

To a solution of 16.3 g (0.1 mol) of 2-amino-5-nitrobenzonitrile in 200 ml of CH$_2$Cl$_2$ at 0° C. was added 21 ml (0.15 mol) of triethyl amine followed by 0.3 g of DMAP and 11.71 g (0.11 mol) of butyryl chloride. The reaction mixture was warmed to room temperature and then heated over night at 50° C. The solution was washed with 1N HCl (1×20 ml), water (1×20 ml), saturated NaHCO$_3$ (2×20 ml) and brine (1×20 ml) and dried over MgSO$_4$. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% H$_2$O$_2$ and 50 ml of water. The mixture was refuxed for 4 hours, cooled and filtered. The filtrate was acidified with 1N HCl and the resulting precipitate recovered by filtration. The residue was recrystalized from MeOH to give 8.3 g (0.036 mol) of pale brown fluffy crystals. 36% yield. $^1$H-NMR (CDCl$_3$): 1.10 (t, 3H, J=7.4 Hz), 1.93 (m, 2H), 2.79 (3 line m, 2H, J=7.3 Hz), 7.80 (d, 1H, J=8.9 Hz), 8.55 (dd, 1H, J=2.5, 8.8 Hz), 9.14 (bs, 1H).

PREPARATION OF 5-ALKYL-2-ARYL-2,4-DIHYDRO-3H-1,2,4-TRIAZOL-3-ONES

EXAMPLE 17

2-(2-chlorophenyl)-5-Butyl-2,4-dihydro-3H-1,2,4-triazol-3-one

Step A: Preparation of ethyl valerimidate (Free Base)

A 12.7 g (76.7 mmol) sample of ethyl valerimidate hydrochloride (prepared from valeronitrile, ethanol, and hydrogen chloride gas as described by A. J. Hill and I. Rabinowitz, J. Am. Chem. Soc., 1926, 48, 734) was dissolved in 33% (w/w) potassium carbonate solution (made by dissolving 15 g of $K_2CO_3$ in 30 mL of $H_2O$) and immediately extracted with either (3×40 mL). The combined ether layers were dried over $Na_2SO_4$, filtered, and concentrated in vacuo to give 7.09 g (72%) of the product as a clear oil, which was used directly in the next step. $^1$H NMR (300 MHz, $CDCl_3$, ppm): δ0.88 (t, J=7 Hz, 3H), 1.24 (t, J=7 Hz, 3H), 1.31 (m, 2H), 1.50 (m, 2H), 2.19 (t, J=7.5 Hz, 2H), 4.06 (q, J=7 Hz, 2H), 6.84 (br s, 1H).

Step B: Preparation of ethyl N-carbethoxyvalerimidate

A solution of 6.5 g (50.3 mmol) of ethyl valerimidate (free base) in 90 mL of dry $CH_2Cl_2$ was treated with 7.71 mL (5.60 g, 55.3 mmol) of triethylamine. The resulting solution was stirred under $N_2$ at $-10°$ C. in an ice-salt bath as a solution of 4.81 mL (5.46 g, 50.3 mmol) of ethyl chloroformate in 10 mL of $CH_2Cl_2$ was added dropwise over 25 minutes. Upon completion of the addition, the cooling bath was removed, and the mixture was stirred at room temperature for 2 hours. Next, the solvent was removed by evaporation in vacuo. The residue was taken up in hexane and filtered to remove triethylamine hydrochloride. Concentration of the filtrate yielded 7.08 g (70%) of the product as a yellow oil, suitable for use in the next step without further purification. NMR indicated a mixture of syn and anti isomers. TLC (98:2 $CH_2Cl_2$—MeOH) showed a close pair of spots, $R_f$ 0.48, 0.52.

$^1$H NMR (200 MHz, $CDCl_3$, ppm): δ0.86 (distorted t, J=7.5 Hz, 3H), 2.15-2.35 (m, 8H), 2.4-2.65 (m, 2H), 2.19, 2.35 (t, J=7.5 Hz, 2H total), 4.0-4.2 (m, 4H). EI-MS: m/e 201 (M+).

Step C: Preparation of 5-butyl-2-(2-chlorophenyl)-2,4-dihydro-3H-1,2,4-triazol-3-one To a solution of 285 mg (2 mmol) of (2-chlorophenyl)hydrazine (generated from the hydrochloride by partitioning between ether and 1N $Na_2CO_3$) in 3 mL of toluene was added 442 mg (2.2 mmol) of ethyl N-carboethoxyvalerimidate (Example 4 Step B). The mixture was heated at 45°-50° C. for 45 minutes. At this time the mixture was treated with 307 mL (223 mg, 2.2 mmol) of triethylamine and then heated overnight at 95° C. The mixture was cooled and concentrated in vacuo. Flash chromatography of the residue on silica gel (gradient elution with 0.6-2% methanol in $CH_2Cl_2$) gave 257 mg (51%) of the product as an off-white solid, mp 103°-104° C., homogeneous by TLC in 19:1 $CH_2Cl_2$—MeOH.

$^1$H NMR (200 MHz, $CDCl_3$, ppm): δ0.92 (t, J=7 Hz, 3H), 1.38 (m, 2H), 1.68 (m, 2H), 2.57 (t, J=7.5 Hz, 2H), 7.3-7.55 (m, 4H), 12.04 (br s, 1H). FAB-MS: m/e 252 (M+1).

Analysis for $C_{12}H_{14}ClN_3O$: Calcd: C, 57.26; H, 5.61; N, 16.69, Found: C, 57.31; H, 5.69; N, 16.58.

PREPARATION OF 5,6 DIALKYL PYRIMIDIN-4(3H)-ONE

EXAMPLE 18

2-n-Butyl-5-ethyl-6-methylpyrimidin-4(3H)-one

A solution of 3.0 g valeramidine hydrochloride, 3.47 g ethyl 2-ethylacetoacetate, and 5.8 mL triethylamine in 20 mL DMF was heated to 120° C. for 18 hours. The mixture was diluted with brine and extracted three times with ether. The combined organic material was washed with brine, was dried over $MgSO_4$, was stripped of solvent in vacuo, and then was still flash chromatographed in 3% MeOH in $CH_2Cl_2$ to give the title compound as a white solid.

$^1$H NMR (300 MHz, $CDCl_3$) δ2.62 (3 line m, 2H), 2.51 (4 line m, 2H), 2.32 (s, 3H), 1.75 (m, 2H), 1.42 (6 line m, 2H), 1.10 (3 line m, 3H), 0.95 (3 line m, 3H).

EXAMPLE 19

2-n-Butyl-5,6-dimethylpyrimidin-4(3H)-one

The title compound is prepared using the procedure in Example 18 and ethyl 2-methylacetoacetate in place of ethyl 2-ethylacetoacetate.

PREPARATION OF 3-N-ALKYL-2-ALKYLQUINAZOLIN-4(3H)-ONES

A general procedure for the synthesis of 3-N-akylated-quinazolin-4(3H)-ones is given below.

A suspension of 1.1 mmol of NaH in 2 mL of dry DMF at 0° C. under nitrogen is treated with 1 mmol of the quinazolin-4(1H)-one as a solid (most quinazolin-4(1H)-ones prepared were insoluble in DMF). Immediate evolution of hydrogen could be observed as the quinazolin-4(1H)-one is deprotonated and dissolves. After 30 minutes the solution was warmed to room temperature for a further 30 minutes. To this solution cooled to 0° C. is added a solution of 1 mmol of the appropriate bromomethylphenyl- or methanesulfonylmethylphenyl-2-, 3-, or 4-pyridine as prepared below, in 1.5 mL of DMF. After 30 minutes, the reaction mixture is warmed to room temperature and stirred overnight. The solution is concentrated in vacuo, and the residue dissolved in 50 mL of EtOAc. The solution is washed with water (3×10 mL) and brine (2×10 mL). The organic phase is dried over $MgSO_4$, filtered and concentrated in vacuo. The residue is then chromatographed on a silica gel column.

The procedure herein described can be used to generate 5-alkyl-2-aryl-3-N-alkyl-'2,4-dihydro-1,2,4-triazol-3-ones and 2,5,6-trialkyl-3-N-alkylpyrimidin-4-(3H)-one. The general procedures for preparing the methanesulfonylmethylphenyl- and bromomethylphenyl-2-, 3-, or 4-pyridines are described below using quinazolinones:

EXAMPLE 20

2-Butyl-6-methyl-3-[[4-[3-(1H-tetrazol-5-yl)-4-pyridinyl]phenyl]methyl]quinazolin-4(3H)-one Step A: Preparation of 3-Cyano-4-(4-tolyl)pyridine To a stirred mixture of 3-cyanopyridine (10 g, 96 mmol), CuI (914 mg, 4.8 mmol), p-tolylmagnesium bromide (100 mL of a 1M solution in $Et_2O$, 100 mmol), THF (200 mL), and $Me_2S$ (100 mL) under $N_2$ at 23° C. was added phenyl chloroformate (12.6 mL, 100 mmol) over a 30 min. period. After 2 h, aqueous $NH_4Cl$ (20%, 100 mL) and $Et_2O$ (100 mL) were added and the mixture was warmed to room temperature. The organic layer was washed sequentially with 1N HCl (50 mL), H$_2$O (50 mL), a 1:1 mixture of 20% aqueous NH$_4$Cl and conc. NH$_4$OH (3×50 mL), and brine (50 mL) then dried (MgSO$_4$). Concentration gave the crude 1-phenoxycarbonyl-4-(p-tolyl)-1,4-dihydropyridine as a tan solid. A portion (8 g) of this crude dihydropyridine was treated with S$_8$ (810 mg) in decalin (25 mL) at reflux for 6 h. This reaction was cooled to rt, EtOAc (100 mL) and H$_2$O (50 mL) were added and the resulting mixture was filtered through celite ®. The organic layer was washed sequentially with 1N NaOH (30 mL), water and brine then dried over (K$_2$CO$_3$). Purification (flash chromatography, 20% EtOAc/hexanes) gave the titled compound as a tan solid.

$^1$H NMR (300 MHz, CDCl$_3$) δ8.91 (s, 1H), 8.76 (d, 1H, J=4.5 Hz), 7.52 (d, 2H, J=8 Hz), 7.44 (d, 1H, J=4.5 Hz), 7.33 (d, 2H, J=8 Hz).

Step D: 3-Cyano-4-(4-bromomethylphenyl)pyridine

A solution of 3-cyano-4-(4-tolyl)pyridine (485 mg, 2.66 mmol), N-bromosuccinimide (929 mg, 5.22 mmol), and dibenzoylperoxide (64 mg, 0.266 mmol) in CCl$_4$ (15 mL) was heated to reflux for 6 h. The mixture was cooled and water (50 mL) and CH$_2$Cl$_2$ (30 mL) were added. The organic layer was dried (MgSO$_4$) and purified by flash chromatography (10% EtOAc/hexanes). The product is not kept in concentrated form for more than 5 minutes and stored only in CH$_2$Cl$_2$ at 0° C. to minimize polymerization.

Step E: 2-Butyl-6-methyl-3-[[4-(3-cyanopyridin-4-yl)phenyl]methyl]quinazolin-4(3H)-one.

To a solution of 2-butyl-6-methylquinazolin-4(1H)-one (1.0 eq.) from Example 1 in DMF at rt is added NaH (1.0 eq.) to generate the sodium salt. After 20 min, 3-cyano-4-(4-bromomethyl phenyl)pyridine (1 mL of a 2M solution in CH$_2$Cl$_2$, 2 eq.) is added and the mixture is stirred at rt for 3 h. HOAc (100 μL) is added, the excess DMF is removed in vacuo then the crude product is isolated by extraction with EtOAc from brine. Purification by flash chromatography will give the above titled compound.

Step F: 2-Butyl-6-methyl-3-[[4-[3-(1H-tetrazol-5-yl)-4-pyridinyl]phenyl]methyl]quinazolin-4(3H)-one.

A solution of 2-butyl-6-methyl-3-[[4-(3-cyanopyridin-4-yl)phenyl]methyl]quinazolin-4(1H)-one (1.0 eq.) and trimethylstannylazide (3 eq.) in toluene is heated to reflux for 4 days. The mixture is cooled to rt, concentrated, then purified by flash chromatography on SiO$_2$ to give the titled compound.

EXAMPLE 21

2-Butyl-6-methyl-3-[[4-[2-(1H-tetrazol-5-yl)-3-pyridinyl]phenyl]methyl]quinazolin-4(3H)-one Step A: 2-Cyano-3-(4-tolyl)pyridine To a mixture of p-tolylmagnesium bromide (9.3 mL of a 1M solution in Et$_2$O, 9.28 mmol) in THF (17 mL) at −78° C. was added ZnCl$_2$ (9.3 mL of a 1M solution in Et$_2$O, 9.28 mmol). The resulting slurry was warmed to rt for 20 min then cooled to 0° C. Bis-(triphenylphosphine)nickle(II) chloride (178 mg, 0.27 mmol) and 3-bromo-2-cyanopyridine (1.0 g, 5.5 mmol); (prepared as reported: Chem. Pharm Bull., 1985, vol. 33, p 565) were added in one portion. After 1 h, saturated aqueous NH$_4$Cl (50 mL) was added and the mixture was extracted with EtOAc (2×50 mL). Purification by flash chromatography (40% EtOAc/hexanes) gave the above titled compound as a white solid.

Step B: 2-Cyano-3-(4-bromomethylphenyl)pyridine

A mixture of 2-cyano-3-(4-tolyl)pyridine (940 mg, 4.84 mmol), N-bromosuccinimide (1.03 mg, 5.81 mmol), and dibenzoylperoxide (117 mg, 0.48 mmol) in CCl$_4$ (70 mL) was heated to reflux to 2 h. The mixture was cooled then filtered through 50 g of silica gel eluting with CH$_2$Cl$_2$. The product was purified further by flash chromatography (20% EtOAc/hexanes) to give the above titled compound as a white solid.

$^1$H NMR (300 MHz, CDCl$_3$) δ8.71 (d, 1H), 7.86 (d, 1H), 7.64–7.55 (m, 5H), 4.56 (s, 2H).

Step C: 2-Butyl-6-methyl-3-[[4-(2-cyanopyridin-3-yl)phenyl]methyl]quinazolin-4(3H)-one To a solution of 2-butyl-6-methylquinazolin-4(1H)-one (1.0 eq.) from Example 1 Step B in DMF at rt is added NaH (1.5 eq. of an 80% dispersion in oil). After 20 min, 2-cyano-3-(4-bromomethylphenyl)pyridine (1.2 eq.) is added and the mixture is stirred at rt for 3 h. Brine (100 mL) and aqueous NH$_4$Cl (40 mL) are added and the product is extracted with EtOAc. Purification by flash chromatography gives the above titled compound.

Step D: 2-Butyl-6-methyl-3-[[4-[2-(1H-tetrazol-5-yl)-3-pyridinyl]phenyl]methyl]quinazolin-4(3H)-one A solution of the product of step C (1.0 eq.) is added trimethylstannylazide (3 eq.) in toluene (3 mL) and heated to reflux for 36 h. The mixture is cooled to rt, concentrated and then can be purified by flash chromatography on SiO$_2$ to give the titled compound.

EXAMPLE 22

2-Butyl-6-methyl-3-[[4-[3-(1H-tetrazol-5-yl)-2-pyridinyl]phenyl]methyl]quinazolin-4(3H)-one The title compound can be prepared according to the procedure described in Example 20 and substituting 2-chloro-3-cyanopyridine.

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-Butyl-6-methyl-3-[[4-[3-(1H-tetrazol-5-yl)-4-pyridinyl]phenyl]methyl]quinazolin-4(3H)-one | 50 |
| Lactose | 149 |
| Magnesium stearate | 1 |
| Capsule (size No. 1) | |
| | 200 |

The 2-butyl-6-methyl-3-[[4-[3-(1H-tetrazol-5-yl)-4-pyridinyl]phenyl]methyl]quinazolin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-butyl-6-methyl-3-[[4-[3-(1H-tetrazol-5-yl)-4-pyridinyl]phenyl]methyl]-quinazolin-4(3H)-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide (25 mg) and 2-butyl-6-methyl-3-[[4-[3-(1H-tetrazol-5-yl)-4-pyridinyl]phenyl]methyl]quinazolin-4(3H)-one (50 mg) pregelatinized starch USP (82 mg), microcrystalline cellulose (82 mg) and magnesium stearate (1 mg).

D: Suppository

Typical suppository formulations for rectal administration can contain 2-butyl-6-methyl-3-[[4-[3-(1H-tetrazol-5-yl)-4-pyridinyl]phenyl]methyl]quinazolin-4(3H)-one (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-butyl-6-methyl-3-[[4-[3-(1H-tetrazol-5-yl)-4-pyridinyl]-phenyl]methyl]-quinazolin-4(3H)-one sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula I:

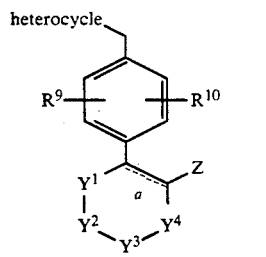

or a pharmaceutically acceptable salt, wherein the heterocycle is defined as:

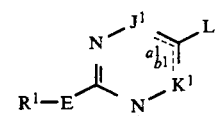

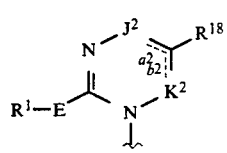

$R^1$ is:
 (a) $(C_1–C_6)$-alkyl, $(C_2–C_6)$-alkenyl or $(C_2–C_6)$-alkynyl each of which is unsubstituted or substituted with a substituent selected from the group consisting of:
  i) aryl as defined below,
  ii) $(C_3–C_7)$-cycloalkyl,
  iii) Cl, Br, I, F,
  iv) OH,
  v) $NH_2$,
  vi) $NH(C_1–C_4)$-alkyl,
  vii) $N[(C_1–C_4)$-alkyl$]_2$,
  viii) $NHSO_2R^2$,
  ix) $CF_3$,
  x) $COOR^2$, or
  xi) $SO_2NHR^2$;
 (b) aryl, wherein aryl is defined as phenyl or naphthyl unsubstituted or substituted with 1 or 2 substituents selected from the group consisting of:
  i) Br, I, Cl, F,
  ii) $(C_1–C_4)$-alkyl,
  iii) $(C_1–C_4)$-alkoxy,
  iv) $NO_2$,
  v) $CF_3$,
  vi) $SO_2NR^2R^2$,
  vii) $(C_1–C_4)$-alkylthio,
  viii) hydroxy,
  ix) amino,
  x) $(C_3–C_7)$-cycloalkyl,
  xi) $(C_3–C_{10})$-alkenyl,
  xii) $CO_2H$, or
  xiii) $CO_2—(C_1–C_4)$-alkyl;
 (c) heteroaryl, wherein heteroaryl is defined as a 5- or 6- membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, or F,
  ii) OH,
  iii) SH,
  iv) $NO_2$,
  v) $(C_1–C_4)$-alkyl,
  vi) $(C_2–C_4)$-alkenyl,
  vii) $(C_2–C_4)$-alkynyl,
  viii) $(C_1–C_4)$-alkoxy,
  ix) $CF_3$,
  x) $CO_2—(C_1–C_4)$-alkyl,
  xi) $NH_2$,
  xii) $NH[(C_1–C_4)$-alkyl], or
  xiii) $N[(C_1–C_4)$-alkyl$]_2$, or
 (d) perfluoro-$(C_1–C_4)$-alkyl;

E is:
 (a) a single bond,
 (b) $—S(O)_n(CH_2)_s—$, or
 (c) $—O—$;
n is 0 to 2;
s is 0 to 5;
$J^1$ is (a) $—C(=M)—$, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{7b}$, $R^{8a}$ and $R^{8b}$;
$K^1$ is (a) $—C(=M)—$, (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a 6-membered aromatic ring containing one nitrogen atom, substituted on the carbon atoms with $R^{7a}$, $R^{7b}$ and $R^{8b}$;

one of $a^1$ or $b^1$ is a double bond in structures Ia provided that when $J^1$ is —C(=M)— then $b^1$ is a double bond and when $K^1$ is —C(=M)— then $a^1$ is a double bond;

$J^2$ is (a) —C(=M)—, or (b) —C($R^{17}$)—;

$K^2$ is (a) —C(=M)—, or (b) —C($R^{17}$)—, provided that one and only one of $J^2$ and $K^2$ is —C(=M)—;

one of $a^2$ or $b^2$ is a double bond in structure Ic provided that when $J^2$ is —C(=M)— then $b^2$ is a double bond and when $K^2$ is —C(=M)— then $a^2$ is a double bond;

M is O, S or $NR^{15}$;

$R^2$ is:
(a) H,
(b) ($C_1$-$C_6$)-alkyl,
(c) —$CH_2$—O—C(O)$CH_3$,
(d) $CH_2$-aryl, or
(e) aryl;

$R^{7a}$ and $R^{7b}$ are independently
(a) H,
(b) ($C_1$-$C_6$)-alkyl, ($C_2$-$C_6$)-alkenyl or ($C_2$-$C_6$)-alkynyl,
(c) Cl, Br, I, F,
(d) $CF_3$, or
(e) when $R^{7a}$ and $R^{7b}$ are bonded to adjacent carbon atoms, they can be joined to form a phenyl or naphthyl ring;

$R^{8a}$ and $R^{8b}$ are independently
(a) H,
(b) aryl-($C_1$-$C_4$)-alkyl,
(c) heteroaryl-($C_1$-$C_4$)-alkyl,
(d) ($C_1$-$C_6$)-alkyl, which is unsubstituted or substituted with a substituent selected from the group consisting of: —CON($R^2$)$_2$, -heteroaryl, —S(O)$_x$—$R^{21}$, -tetrazol-5-yl, —CONHSO$_2$$R^{21}$, —SO$_2$NH-heteroaryl, —SO$_2$NHCOR$^{21}$, —PO(O$R^2$)$_2$, —PO(O$R^2$)$_2$, —SO$_2$NH—CN, —N$R^2$COOR$^{21}$, —OH, —NH$_2$, guanidino, ($C_1$-$C_4$)-alkoxy, ($C_1$-$C_4$)-alkylthio, ($C_1$-$C_4$)-alkylamino, ($C_1$-$C_4$)-dialkylamino, —COO$R^2$, —CONH$R^2$, —O—CO$R^2$, or phenyl or naphthyl,
(e) —CO-aryl,
(f) ($C_3$-$C_7$)-cycloalkyl,
(g) Cl, Br, I, F,
(h) —OH,
(i) —O$R^{21}$,
(j) —SH,
(k) —S(O)$_n$—($C_1$-$C_4$)-alkyl,
(l) —CO$R^2$,
(m) —CO$_2$H,
(n) —CO$_2$—($C_1$-$C_4$)-alkyl,
(o) —SO$_3$H,
(p) —N$R^2$$R^{21}$,
(q) —N$R^2$COR$^{21}$,
(r) —N$R^2$COOR$^{21}$,
(s) —SO$_2$NH$R^2$,
(t) —SO$_2$N$R^2$$R^2$,
(u) —NO$_2$,
(v) —NHSO$_2$CF$_3$,
(w) —CONR$^2$,
(x) —($C_1$-$C_4$)-perfluoroalkyl,
(y) —COO$R^2$,
(z) —SO$_3$H,
(aa) —N($R^2$)SO$_2$$R^{21}$,
(bb) —N$R^2$CONR$^4$$R^{21}$,
(cc) —OC(=O)N$R^{21}$$R^2$,
(dd) -aryl,
(ee) —NHSO$_2$CF$_3$,
(ff) —SO$_2$NH-heteroaryl,
(gg) —SO$_2$NHCOR$^{21}$,
(hh) —CONHSO$_2$$R^{21}$,
(ii) —PO(O$R^2$)$_2$,
(jj) -tetrazol-5-yl,
(kk) —CONH(tetrazol-5-yl),
(ll) —SO$_2$NHCN, or
(mm) -heteroaryl;

—$Y^1$—$Y^2$—$Y^3$—$Y^4$— is:
(a) —N—CR$^{11}$—CR$^{11}$=CR$^{11}$—,
(b) —CR$^{11}$=N—CR$^{11}$=CR$^{11}$—,
(c) —CR$^{11}$=CR$^{11}$—N=CR$^{11}$—,
(d) —CR$^{11}$=CR$^{11}$—CR$^{11}$=N—,
(e) —N=CR$^{11}$—N=CR$^{11}$—,
(f) —CR$^{11}$=N—CR$^{11}$=N—,
(g) —N=N—CR$^{11}$=CR$^{11}$—,
(h) —CR$^{11}$=N—N=CR$^{11}$—,
(i) —CR$^{11}$=CR$^{11}$—N=N—,
(j) —N=CR$^{11}$—CR$^{11}$=N—,

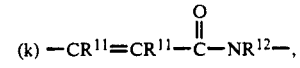

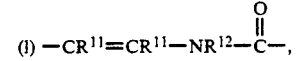

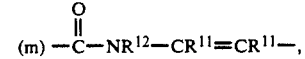

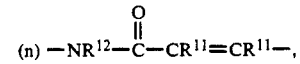

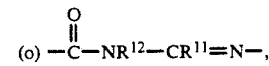

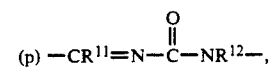

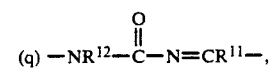

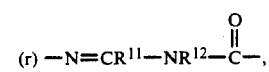

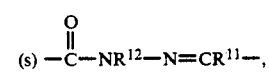

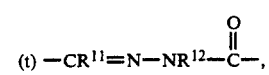

wherein a represents a double bond in each of the above definitions [(a) thru (t)]

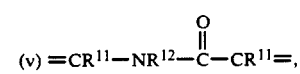

-continued (x) 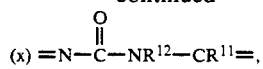

(y) 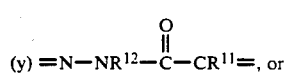

(z) 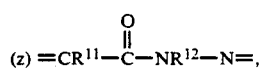

wherein a represents a single bond in each of the above definitions [(u) thru (z)];

$R^9$ and $R^{10}$ are each independently:
(a) H,
(b) Cl, Br, I, F,
(c) $NO_2$,
(d) $(C_1-C_6)$-alkyl,
(e) $(C_1-C_6)$-acyloxy,
(f) $(C_3-C_6)$-cycloalkyl,
(g) $(C_1-C_6)$-alkoxy,
(h) $-NHSO_2R^2$,
(i) hydroxy-$(C_1-C_4)$-alkyl,
(j) aryl-$(C_1-C_4)$-alkyl,
(k) $(C_1-C_4)$-alkylthio,
(l) $(C_1-C_4)$-alkylsulfinyl,
(m) $(C_1-C_4)$-alkylsulfonyl,
(n) $NH_2$,
(o) $(C_1-C_4)$-alkylamino,
(p) $(C_1-C_4)$-dialkylamino,
(q) $CF_3$,
(r) $-SO_2NHR^2$,
(s) furyl,
(t) aryl, or
(u) when $R^9$ and $R^{10}$ are bonded to adjacent carbon atoms, they can be joined to form a phenyl or naphthyl ring;

$R^{11}$ is:
(a) H,
(b) Cl, Br, I, F,
(c) $NO_2$,
(d) $NH_2$,
(e) $(C_1-C_4)$-alkylamino,
(f) di-$(C_1-C_4$-alkyl)amino
(g) $SO_2NHR^2$,
(h) $CF_3$,
(i) $(C_1-C_4)$-alkyl,
(j) $(C_1-C_4)$-alkoxy, or
(k) when two $R^{11}$ substituents are bonded to adjacent carbon atoms, they can be joined to form a phenyl or naphthyl ring;

$R^{12}$ is:
(a) H,
(b) $(C_1-C_4)$-alkyl, or
(c) phenyl or $-CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl], $N[(C_1-C_4)$-alkyl]$_2$, $NH_2$ or $CO_2R^2$;

Z is:
(a) $-CO_2R^2$,
(b) $-SO_3R^{13}$,
(c) $-NHSO_2R^{14}$,
(d) $-PO(OR^{13})_2$,
(e) $-SO_2NHR^2$,
(f) $-CONHOR^{13}$, (g) 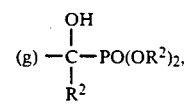

(h) $-CN$,
(i) $-SO_2NH$-heteroaryl,
(j) $-CH_2SO_2NH$-heteroaryl,
(k) $-SO_2NHC(O)R^{14}$,
(l) $-CH_2SO_2NHC(O)R^{14}$,
(m) $-C(O)NHSO_2R^{14}$,
(n) $-CH_2C(O)NHSO_2R^{14}$,
(o) $-NHSO_2NHC(O)R^{14}$,
(p) $-NHC(O)NHSO_2R^{14}$, (q) 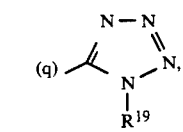

(r) $-CH_2$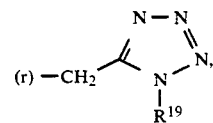

(s) $-CON$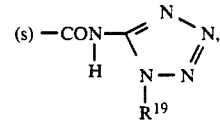
      H (t)  $-CONHNHSO_2CF_3$, (u) 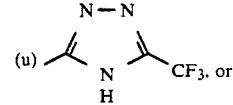, or (v) 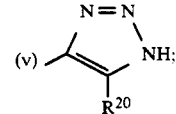;

$R^{13}$ is H, $-CH_2$-phenyl or $-CH(R^4)-O-C(O)R^4$;
$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, $-OH$, $-SH$, $(C_1-C_4)$-alkyl, $(C_1-C_4)$-alkoxy, $(C_1-C_4)$-alkylthio, $-CF_3$, Cl, Br, F, I, $-NO_2$, $-CO_2H$, $CO_2-(C_1-C_4)$-alkyl, $-NH_2$, $-N[(C_1-C_4)$-alkyl]$_2$, $-NH[(C_1-C_4)$-alkyl], $-PO_3H$ or $PO(OH)(C_1-C_4)$-alkyoxy, or
(e) $(C_1-C_4)$-perfluoroalkyl;

$R^{15}$ is
(a) H,
(b) aryl;
(c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, $-OH$, $-NH_2$, $-NH[(C_1-C_4)$-alkyl], —N[($C_1$-$C_4$)-alkyl]$_2$, —NH—SO$_2$R$^2$, —COOR$^2$, —SO$_2$NHR$^2$; or (d) heteroaryl;

$M_1$ is M or —C(O)—;

z is 0 or 1;

r and t are 0 to 2;

$R^{17}$ and $R^{18}$ are each independently selected from:
(a) H,
(b) aryl-($C_1$-$C_4$)-alkyl-,
(c) heteroaryl-($C_1$-$C_4$)-alkyl-,
(d) ($C_1$-$C_4$)-alkyl unsubstituted or substituted with a substituent selected from the group consisting of —OH, —NH$_2$, guanidino, ($C_1$-$C_4$)-alkoxy, ($C_1$-$C_4$)-alkylthio, ($C_1$-$C_4$)-alkylamino, ($C_1$-$C_4$)-dialkylamino, —COOR$^2$, —CONHR$^2$, —O—COR$^2$, CF$_3$;
(e) ($C_1$-$C_4$)-alkenyl,
(f) —CO-aryl,
(g) ($C_3$-$C_7$)-cycloalkyl,
(h) Cl, Br, I, F,
(i) —OH,
(j) —O—($C_1$-$C_4$)-alkyl,
(k) —($C_1$-$C_4$)-perfluoroalkyl,
(l) —SH,
(m) —S(O)$_n$—($C_1$-$C_4$)-alkyl,
(n) —CHO,
(o) —CO$_2$R$^2$
(p) —SO$_3$H,
(q) —NH$_2$,
(r) —NH[($C_1$-$C_4$)-alkyl],
(s) —N[($C_1$-$C_4$)-alkyl]$_2$,
(t) —NHCO$_2$—($C_1$-$C_4$)-alkyl,
(u) —SO$_2$NR$^2$R$^2$,
(v) —CH$_2$OCOR$^2$
(w) —NH—SO$_2$—($C_1$-$C_4$)-alkyl,
(x) 5 or 6 membered saturated heterocycle containing one nitrogen atom and optionally containing one other heteroatom selected from N, O, or S,
(y) aryl,
(z) heteroaryl,
(aa) tetrazol-5-yl,
(bb) —[($C_1$-$C_4$)-alkyl]NR$^2$R$^{21}$,
(cc) —[($C_1$-$C_4$)-alkyl]NR$^2$COR$^{21}$,
(dd) —[($C_1$-$C_4$)-alkyl]NR$^2$COOR$^{21}$,
(ee) —[($C_1$-$C_4$)-alkyl]CONR$^2$R$^2$,
(ff) —[($C_1$-$C_4$)-alkyl]N(R$^2$)SO$_2$R$^{21}$,
(gg) —[($C_1$-$C_4$)-alkyl]NR$^2$CONR$^2$R$^{21}$, or
(hh) —[($C_1$-$C_4$)-alkyl]OC(=O)NR$^{21}$R$^2$;

$R^{19}$ is:
(a) H,
(b) ($C_1$-$C_6$)-alkyl,
(c) ($C_2$-$C_4$)-alkenyl,
(d) ($C_1$-$C_4$)-alkoxyalkyl,
(e) —CH$_2$—O—C(O)CH$_3$, or
(f) —CH$_2$-phenyl, wherein the phenyl is unsubstituted or substituted with a substituent selected from the group consisting of: —NO$_2$, —NH$_2$, —OH or —OCH$_3$;

$R^{20}$ is:
CN, NO$_2$, CO$_2$R$^2$, ($C_1$-$C_6$)-perfluoroalkyl or CF$_3$; and $R^{21}$ is:
(a) aryl, or
(b) ($C_1$-$C_4$)-alkyl, is unsubstituted or substituted with:
i) NH$_2$,
ii) NH[($C_1$-$C_4$)-alkyl],
iii) N[($C_1$-$C_4$)-alkyl]$_2$,
iv) CO$_2$H,
v) CO$_2$($C_1$-$C_4$)-alkyl,
vi) OH,
vii) SO$_3$H, or
viii) SO$_2$NH$_2$.

2. The compound of claim 1 or a pharmaceutically acceptable salt wherein:

$R^1$ is:
(a) ($C_1$-$C_6$)-alkyl, ($C_2$-$C_6$)-alkenyl or ($C_2$-$C_6$)-alkynyl each of which can be unsubstituted or substituted with a substituent selected from the group consisting of:
   i) aryl, wherein aryl is defined as phenyl or naphthyl, unsubstituted or substituted with 1 or 2 substituents selected from the group consisting of:
      Cl, Br, I, F, ($C_1$-$C_4$)-alkyl, ($C_1$-$C_4$)-alkoxy, NO$_2$, CF$_3$, SO$_2$NR$^2$R$^2$, ($C_1$-$C_4$)-alkylthio, hydroxy, amino, ($C_3$-$C_7$)-cycloalkyl, CO$_2$H, CO$_2$—($C_1$-$C_4$)-alkyl, or ($C_3$-$C_{10}$)-alkenyl,
   ii) ($C_3$-$C_7$)-cycloalkyl,
   iii) Cl, Br, I, F,
   iv) OH,
   v) NH$_2$,
   vi) NH($C_1$-$C_4$)-alkyl,
   vii) N[($C_1$-$C_4$)-alkyl)]$_2$,
   viii) NHSO$_2$R$^2$,
   ix) CF$_3$,
   x) COOR$^2$, or
   xi) SO$_2$NHR$^2$,
(b) ($C_1$-$C_4$)-perfluoroalkyl, or
(c) ($C_3$-$C_7$)-cycloalkyl, which can be substituted or unsubstituted with a substitutent selected from the group consisting of: ($C_1$-$C_4$)-alkyl, ($C_1$-$C_4$)-perfluoroalkyl, Cl, Br, I, or F;

E is:
(a) single bond,
(b) —S—, or
(c) —O—;

n is 0, 1, or 2;

$J^1$ is (a)—C(=M)—, (b) $J^1$ and L are connected together to form a 6-carbon aromatic ring substituted with $R^{7a}$, $R^{7b}$, $R^{8a}$ and $R^{8b}$ or (c) $J^1$ and L are connected together to form a 6-membered aromatic ring containing one nitrogen atom not at $J^1$, substituted with $R^{7a}$, $R^{7b}$, $R^{8a}$ and $R^{8b}$;

$K^1$ is (a)—C(=M)—, or (b) $K^1$ and L are connected together to form a 6-carbon aromatic ring substituted with $R^{7a}$, $R^{7b}$, $R^{8a}$ and $R^{8b}$, or (c) $K^1$ and L are connected together to form a six-membered aromatic ring containing one nitrogen atom substituted with $R^{7a}$, $R^{7b}$ and $R^{8a}$ provided that one and only one of $J^1$ and $K^1$ is —C(=M)—;

one of $a^1$ or $b^1$ is a double bond in structure Ia provided that when $J^1$ is —C(=M)— then $b^1$ is a double bond and when $K^1$ is —C(=M)— then $a^1$ is a double bond;

$J^2$ is (a)—C(=M)—, or (b) —C(R$^{17}$)—;

$K^2$ is (a)—C(=M)—, or (b)—C(R$^{17}$)—, provided that one and only one of $J^2$ and $K^2$ is —C(=M)—; one of $a^2$ or $b^2$ is a double bond in structure Ic provided that when $J^2$ is —C(=M)— then $b^2$ is a double bond and when $K^2$ is —C(=M)— then $a^2$ is a double bond;

M is O, S or NR$^{15}$;

$R^2$ is:
(a) H, (b) $(C_1-C_6)$-alkyl,
(c) $-CH_2-O-C(O)CH_3$,
(d) $CH_2$-aryl, or
(e) aryl;

$R^{7a}$ and $R^{7b}$ are independently
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl or naphthyl ring;

$R^{8a}$ and $R^{8b}$ are independently
(a) H,
(b) aryl-$(C_1-C_4)$-alkyl,
(c) heteroaryl-$(C_1-C_4)$-alkyl, wherein heteroaryl is defined as a 5- or 6- membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, or F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy,
  ix) $CF_3$,
  x) $CO_2-(C_1-C_4)$-alkyl,
  xi) $NH_2$,
  xii) $NH[(C_1-C_4)$-alkyl], or
  xiii) $N[(C_1-C_4)$-alkyl]$_2$,
(d) $(C_1-C_6)$-alkyl, is unsubstituted or substituted with a substituent selected from the group consisting of: $-CON(R^2)_2$, -heteroaryl, $-S(O)_x-R^{21}$, -tetrazol-5-yl, $-CONHSO_2R^{21}$, $-SO_2NH$-heteroaryl, $-SO_2NHCOR^{21}$, $-PO(OR^2)_2$, $-PO(OR^2)_2$, $-SO_2NH-CN$, $-NR^2COOR^{21}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^2$, $-CONHR^2$, $-O-COR^2$, or aryl,
(e) $-CO$-aryl,
(f) $(C_3-C_7)$-cycloalkyl,
(g) Cl, Br, I, F,
(h) $-OH$,
(i) $-OR^{21}$,
(j) $-SH$,
(k) $-S(O)_n-(C_1-C_4)$-alkyl,
(l) $-COR^2$,
(m) $-CO_2H$,
(n) $-CO_2-(C_1-C_4)$-alkyl,
(o) $-SO_3H$,
(p) $-NR^2R^{21}$,
(q) $-NR^2COR^{21}$,
(r) $-NR^2COOR^{21}$,
(s) $-SO_2NR^2$,
(t) $-SO_2NR^2R^2$,
(u) $-NO_2$,
(v) $-NHSO_2CF_3$,
(w) $-CONR^2R^2$,
(x) $-(C_1-C_4)$-perfluoroalkyl,
(y) $-COOR^2$,
(z) $-SO_3H$,
(aa) $-N(R^2)SO_2R^{21}$,
(bb) $-NR^2CONR^2R^{21}$,
(cc) $-OC(=O)NR^{21}R^2$,
(dd) -aryl,
(ee) $-NHSO_2CF_3$,
(ff) $-SO_2NH$-heteroaryl,
(gg) $-SO_2NHCOR^{21}$,
(hh) $-CONHSO_2R^{21}$,
(ii) $-PO(OR^2)_2$,
(jj) -tetrazol-5-yl,
(kk) $-CONH$(tetrazol-5-yl),
(ll) $-SO_2NHCN$, or
(mm) -heteroaryl;

$-Y^1-Y^2-Y^3-Y^4-$ is:
(a) $-N-CR^{11}=CR^{11}=CR^{11}-$,
(b) $-CR^{11}=N-CR^{11}=CR^{11}-$,
(c) $-CR^{11}=CR^{11}-N=CR^{11}-$, or
(d) $-CR^{11}=CR^{11}-CR^{11}=N-$,
wherein a represents a double bond in each of the above definitions [(a) thru (d)];

$R^9$ and $R^{10}$ are each independently:
(a) H,
(b) Cl, Br, I, F,
(c) $CF_3$,
(d) $(C_1-C_6)$-alkyl,
(e) $(C_1-C_6)$-acyloxy,
(f) $(C_3-C_6)$-cycloalkyl,
(g) $(C_1-C_6)$-alkoxy,
(h) hydroxy-$(C_1-C_4)$-alkyl,
(i) aryl-$(C_1-C_4)$-alkyl,
(j) $(C_1-C_4)$-alkylthio,
(k) $(C_1-C_4)$-alkylsulfinyl,
(l) $(C_1-C_4)$-alkylsulfonyl, or
(m) when $R^9$ and $R^{10}$ are bonded to adjacent carbon atoms, they can be joined to form a phenyl or naphthyl ring;

$R^{11}$ is:
(a) H,
(b) Cl, Br, I, F,
(c) $NO_2$,
(d) $NH_2$,
(e) $(C_1-C_4)$-alkylamino,
(f) di-$(C_1-C_4$-alkyl)amino
(g) $SO_2NHR^2$,
(h) $CF_3$,
(i) $(C_1-C_4)$-alkyl,
(j) $(C_1-C_4)$-alkoxy, or
(k) when two $R^{11}$ substituents are bonded to adjacent carbon atoms, they can be joined to form a phenyl or naphthyl ring;

$R^{12}$ is:
(a) H,
(b) $(C_1-C_4)$-alkyl, or
(c) phenyl or $-CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl], $N[(C_1-C_4)$-alkyl]$_2$, $NH_2$ or $CO_2R^2$;

Z is:
(a) $-CO_2R^2$,
(b) $-CN$,
(c) $-SO_2NH$-heteroaryl,
(d) $-CH_2SO_2NH$-heteroaryl,
(e) $-SO_2NHC(O)R^{14}$,
(f) $-C(O)NHSO_2R^{14}$,
(g) $-NHSO_2R^{14}$, or
(h) $-1H$-tetrazol-5-yl;

$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, —OH, —SH, $(C_1-C_4)$-alkyl, $(C_1-C_4)$-alkoxy, $(C_1-C_4)$-alkylthio, —$CF_3$, Cl, Br, F, I, —$NO_2$, —$CO_2H$, $CO_2$—$(C_1-C_4)$-alkyl, —$NH_2$, —$N[(C_1-C_4)$-alkyl$]_2$, —$NH[(C_1-C_4)$-alkyl], —$PO_3H$, $PO(OH)(C_1-C_4)$-alkyoxy, or
(e) $(C_1-C_4)$-perfluoroalkyl;

$R^{15}$ is:
(a) H,
(b) aryl,
(c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, —OH, —$NH_2$, —$NH[(C_1-C_4)$-alkyl], —$N[(C_1-C_4)$-alkyl$]_2$, —NH—$SO_2R^2$, —$COOR^2$, —$SO_2NHR^2$, or
(d) heteroaryl;

$R^{17}$ and $R^{18}$ are independently
(a) H,
(b) aryl-$(C_1-C_4)$-alkyl-,
(c) heteroaryl-$(C_1-C_4)$-alkyl-,
(d) $(C_1-C_4)$-alkyl, unsubstituted or substituted with a substituent selected from the group consisting of: —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^2$, —$CONHR^2$, or —O—$COR^2$, $CF_3$,
(e) $(C_1-C_4)$-alkenyl,
(f) —CO—aryl,
(g) $(C_3-C_7)$-cycloalkyl,
(h) Cl, Br, I, F,
(i) —OH,
(j) —O—$(C_1-C_4)$-alkyl,
(k) —$(C_1-C_4)$-perfluoroalkyl,
(l) —SH,
(m) —$S(O)_n$—$(C_1-C_4)$-alkyl,
(n) —CHO,
(o) —$CO_2R^2$,
(p) —$SO_3H$,
(q) —$NH_2$,
(r) —$NH[(C_1-C_4)$-alkyl],
(s) —$N[(C_1-C_4)$-alkyl$]_2$,
(t) —$NHCO_2$—$(C_1-C_4)$-alkyl,
(u) —$SO_2NR^2R^2$,
(v) —$CH_2OCOR^2$,
(w) —NH—$SO_2$—$(C_1-C_4)$-alkyl,
(x) 5 or 6 membered saturated heterocycle containing one nitrogen atom and optionally containing one other heteroatom selected from N, O, or S,
(y) aryl,
(z) heteroaryl,
(aa) tetrazol-5-yl, or
(bb) —$[(C_1-C_4)$-alkyl]$NR^2R^{21}$,
(cc) —$[(C_1-C_4)$-alkyl]$NR^2COR^{21}$,
(dd) —$[(C_1-C_4)$-alkyl]$NR^2COOR^{21}$,
(ee) —$[(C_1-C_4)$-alkyl]$CONR^2R^2$,
(ff) —$[(C_1-C_4)$-alkyl]$N(R^2)SO_2R^{21}$,
(gg) —$[(C_1-C_4)$-alkyl]$NR^2CONR^2R^{21}$, or
(hh) —$[(C_1-C_4)$-alkyl]OC(=O)$NR^{21}R^2$; and $R^{21}$ is:
(a) aryl, or
(b) $(C_1-C_4)$-alkyl which is unsubstituted or substituted with:
  i) $NH_2$,
  ii) $NH[(C_1-C_4)$-alkyl],
  iii) $N[(C_1-C_4)$-alkyl$]_2$,
  iv) $CO_2H$,
  v) $CO_2(C_1-C_4)$-alkyl,
  vi) OH,
  vii) $SO_3H$, or
  viii) $SO_2NH_2$.

3. The compound of claim 1 a pharmaceutically acceptable salt wherein:
$R^1$ is:
(a) $(C_1-C_6)$-alkyl $(C_2-C_6)$-alkenyl or $(C_2-C_6)$-alkynyl each of which is unsubstituted or substituted with a substituent selected from the group consisting of:
  i) $(C_1-C_4)$-alkylthio,
  ii) $(C_1-C_4)$-alkoxy,
  iii) $CF_3$,
  iv) $CF_2CF_3$, or
  v) $(C_3-C_5)$-cycloalkyl,
(b) perfluoro-$(C_1-C_4)$-alkyl, or
(c) $(C_3-C_7)$-cycloalkyl, which can be substituted or unsubstituted with a substituent selected from the group consisting of: $(C_1-C_4)$-alkyl, $(C_1-C_4)$-perfluoroalkyl, Cl, Br, I or F;

E is a single bond;
n is 0 to 2;
$J^1$ and L are connected together to form a 6-carbon aromatic ring substituted with $R^{7a}$, $R^{7b}$, $R^{8a}$ and $R^{8b}$; or $J^1$ and L are connected together to form a 6-membered aromatic ring containing one nitrogen atom not at $J^1$, substituted with $R^{7a}$, $R^{7b}$, $R^{8a}$ and $R^{8b}$;
$K^1$ is —C(=M)—;
$a^1$ is a double bond;
$J^2$ is —$C(R^{17})$—;
$K^2$ is —C(=M)—;
$a^2$ is a double bond;
M is O, or $NR^{15}$;
$R^2$ is:
(a) H,
(b) $(C_1-C_6)$-alkyl,
(c) —$CH_2$—O—$C(O)CH_3$,
(d) benzyl, or
(e) phenyl;

$R^{7a}$ and $R^{7b}$ are independently
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently
(a) H,
(b) aryl-$(C_1-C_4)$-alkyl, wherein aryl is defined as phenyl or naphthyl unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $NO_2$,
  v) $CF_3$,
  vi) $SO_2NR^2R^2$, vii) (C$_1$-C$_4$)-alkylthio,
viii) hydroxy,
ix) amino,
x) (C$_3$-C$_7$)-cycloalkyl,
xi) (C$_3$-C$_{10}$)-alkenyl,
xii) CO$_2$H, or
xiii) CO$_2$—(C$_1$-C$_4$)-alkyl;

(c) heteroaryl-(C$_1$-C$_4$)-alkyl, wherein heteroaryl is defined as a 5- or 6- membered heteroaromatic moiety, which can contain one or two members selected from the group consisting of N, O, S and wherein the heteroaryl is unsubstituted, monosubstituted or disubstituted with substituents selected from the group consisting of:
 i) Cl, Br, I, or F,
 ii) OH,
 iii) SH,
 iv) NO$_2$,
 v) (C$_1$-C$_4$)-alkyl,
 vi) (C$_2$-C$_4$)-alkenyl,
 vii) (C$_2$-C$_4$)-alkynyl,
 viii) (C$_1$-C$_4$)-alkoxy,
 ix) CF$_3$,
 x) CO$_2$—(C$_1$-C$_4$)-alkyl,
 xi) NH$_2$,
 xii) NH[(C$_1$-C$_4$)-alkyl], or
 xiii) N[(C$_1$-C$_4$)-alkyl]$_2$, (d) (C$_1$-C$_6$)-alkyl, unsubstituted or substituted with a substituent selected from the group consisting of: —CON(R$^2$)$_2$, -heteroaryl, —S(O)$_n$—R$^{21}$, tetrazol-5-yl, —CONHSO$_2$R$^{21}$, —SO$_2$NH-heteroaryl, —SO$_2$NHCOR$^{21}$, —PO(OR$^2$)$_2$, —PO(OR$^2$)$_2$, —SO$_2$NH—CN, —NR$^2$COOR$^{21}$, —OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^2$, —CONHR$^2$, —O—COR$^2$, or aryl,
(e) —CO-aryl,
(f) (C$_3$-C$_7$)-cycloalkyl,
(g) Cl, Br, I, F,
(h) —OH,
(i) —OR$^{21}$,
(j) —SH,
(k) —S(O)$_n$—(C$_1$-C$_4$)-alkyl,
(l) —COR$^2$,
(m) —CO$_2$H,
(n) —CO$_2$—(C$_1$-C$_4$)-alkyl,
(o) —SO$_3$H,
(p) —NR$^2$R$^{21}$,
(q) —NR$^2$COR$^{21}$,
(r) —NR$^2$COOR$^{21}$,
(s) —SO$_2$NR$^2$,
(t) —SO$_2$NR$^2$R$^2$,
(u) —NO$_2$,
(v) —NHSO$_2$CF$_3$,
(w) —CONR$^2$R$^2$,
(x) —(C$_1$-C$_4$)-perfluoroalkyl,
(y) —COOR$^2$,
(z) —SO$_3$H,
(aa) —N(R$^2$)SO$_2$R$^{21}$,
(bb) —NR$^2$CONR$^2$R$^{21}$,
(cc) —OC(=O)NR$^{21}$R$^2$,
(dd) -aryl,
(ee) —NHSO$_2$CF$_3$,
(ff) —SO$_2$NH-heteroaryl,
(gg) —SO$_2$NHCOR$^{21}$,
(hh) —CONHSO$_2$R$^{21}$,
(ii) —PO(OR$^2$)$_2$,
(jj) -tetrazol-5-yl,
(kk) —CONH(tetrazol-5-yl),
(ll) —SO$_2$NHCN, or
(mm) -heteroaryl;

—Y$^1$—Y$^2$—Y$^3$—Y$^4$— is:
 (a) —N=CR$^{11}$—CR$^{11}$=CR$^{11}$—,
 (b) —CR$^{11}$=N—CR$^{11}$=CR$^{11}$—,
 (c) —CR$^{11}$=CR$^{11}$—N=CR$^{11}$—, or
 (d) —CR$^{11}$=CR$^{11}$—CR$^{11}$=N—,
wherein a represents a double bond in each of the above definitions [(a) thru (d)];

R$^9$ and R$^{10}$ are each independently:
 (a) H,
 (b) Cl, Br, I, F,
 (c) CF$_3$,
 (d) (C$_1$-C$_6$)-alkyl,
 (e) (C$_1$-C$_6$)-acyloxy,
 (f) (C$_3$-C$_6$)-cycloalkyl,
 (g) (C$_1$-C$_6$)-alkoxy,
 (h) hydroxy-(C$_1$-C$_4$)-alkyl,
 (i) aryl-(C$_1$-C$_4$)-alkyl,
 (j) (C$_1$-C$_4$)-alkylthio,
 (k) (C$_1$-C$_4$)-alkylsulfinyl,
 (l) (C$_1$-C$_4$)-alkylsulfonyl, or
 (m) when R$^9$ and R$^{10}$ are bonded to adjacent carbon atoms, they can be joined to form a phenyl or naphthyl ring;

R$^{11}$ is:
 (a) H,
 (b) Cl, Br, I, F,
 (c) NO$_2$,
 (d) NH$_2$,
 (e) (C$_1$-C$_4$)-alkylamino,
 (f) di-(C$_1$-C$_4$-alkyl)amino
 (g) SO$_2$NHR$^2$,
 (h) CF$_3$,
 (i) (C$_1$-C$_4$)-alkyl,
 (j) (C$_1$-C$_4$)-alkoxy, or
 (k) when two R$^{11}$ substituents are bonded to adjacent carbon atoms, they can be joined to form a phenyl or naphthyl ring;

R$^{12}$ is:
 (a) H,
 (b) (C$_1$-C$_4$)-alkyl, or
 (c) phenyl or —CH$_2$-phenyl, in which the phenyl is unsubstituted or substituted with one or two substituents selected from the group consisting of: Cl, Br, I, F, (C$_1$-C$_4$)-alkyl, or (C$_1$-C$_4$)-alkoxy, CF$_3$, NH[(C$_1$-C$_4$)-alkyl], N[(C$_1$-C$_4$)-alkyl]$_2$, NH$_2$ or CO$_2$R$^2$;

Z is:
 (a) —CO$_2$R$^2$,
 (b) —CN,
 (c) —SO$_2$NH-heteroaryl,
 (d) —CH$_2$SO$_2$NH-heteroaryl,
 (e) —SO$_2$NHC(O)R$^{14}$,
 (f) —C(O)NHSO$_2$R$^{14}$,
 (g) —NHSO$_2$R$^{14}$, or
 (h) —1H-tetrazol-5-yl;

R$^{14}$ is
 (a) aryl,
 (b) heteroaryl,
 (c) (C$_3$-C$_7$)-cycloalkyl,
 (d) (C$_1$-C$_4$)-alkyl, unsubstituted or substituted with a substituent selected from the group consisting of: aryl, heteroaryl, —OH, —SH, (C$_1$-C$_4$)-alkyl, (C$_1$-C$_4$)-alkoxy, (C$_1$-C$_4$)-alkylthio, —CF$_3$, Cl, Br, F, I, —NO$_2$, —CO$_2$H, CO$_2$—(C$_1$-C$_4$)-alkyl, —NH$_2$, —N[(C$_1$-C$_4$)-alkyl]$_2$, —NH[(C$_1$-C$_4$)-alkyl], —PO$_3$H, PO(OH)(C$_1$-C$_4$)-alkyoxy, or
(e) (C$_1$-C$_4$)-perfluoroalkyl;

R$^{15}$ is:
(a) H,
(b) aryl,
(c) (C$_1$-C$_6$)-alkyl, (C$_2$-C$_6$)-alkenyl or (C$_2$-C$_6$)-alkynyl each of which is unsubstituted or substituted with one or more substituents selected from the group consisting of aryl as defined above, (C$_3$-C$_7$)-cycloalkyl, Cl, Br, I, F, —OH, —NH$_2$, —NH[(C$_1$-C$_4$)-alkyl], —N[(C$_1$-C$_4$)-alkyl]$_2$, —NH—SO$_2$R$^2$, —COOR$^2$, —SO$_2$NHR$^2$; or
(d) heteroaryl;

R$^{17}$ and R$^{18}$ are independently:
(a) H,
(b) aryl-(C$_1$-C$_4$)-alkyl-,
(c) heteroaryl-(C$_1$-C$_4$)-alkyl-,
(d) (C$_1$-C$_4$)-alkyl, unsubstituted or substituted with a substituent selected from the group consisting of: —OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^2$, —CONHR$^2$, —O—COR$^2$, CF$_3$;
(e) (C$_1$-C$_4$)-alkenyl,
(f) —CO-aryl,
(g) (C$_3$-C$_7$)-cycloalkyl,
(h) Cl, Br, I, F,
(i) —OH,
(j) —O—(C$_1$-C$_4$)-alkyl,
(k) —(C$_1$-C$_4$)-perfluoroalkyl,
(l) —SH,
(m) —S(O)$_n$—(C$_1$-C$_4$)-alkyl,
(n) —CHO,
(o) —CO$_2$R$^2$,
(p) —SO$_3$H,
(q) —NH$_2$,
(r) —NH[(C$_1$-C$_4$)-alkyl],
(s) —N[(C$_1$-C$_4$)-alkyl]$_2$,
(t) —NHCO$_2$—(C$_1$-C$_4$)-alkyl,
(u) —SO$_2$NR$^2$R$^2$,
(v) —CH$_2$OCOR$^2$
(w) —NH—SO$_2$—(C$_1$-C$_4$)-alkyl,
(x) 5 or 6 membered saturated heterocycle containing one nitrogen atom and optionally containing one other heteroatom selected from N, O, or S,
(y) aryl,
(z) heteroaryl, or
(aa) tetrazol-5-yl; and R$^{21}$ is:
(a) aryl, or
(b) (C$_1$-C$_4$)-alkyl which is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$.

4. A compound of formula:

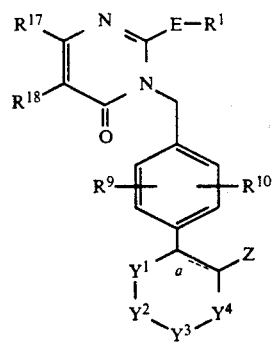

or its pharmaceutically acceptable salt wherein:
R$^1$ is:
(a) (C$_1$-C$_6$)-alkyl (C$_2$-C$_6$)-alkenyl or (C$_2$-C$_6$)-alkynyl each of which is unsubstituted or substituted with a substituent selected from the group consisting of:
  i) (C$_1$-C$_4$)-alkylthio,
  ii) (C$_1$-C$_4$)-alkoxy,
  iii) CF$_3$,
  iv) CF$_2$CF$_3$, or
  v) (C$_3$-C$_5$)-cycloalkyl,
(b) perfluoro-(C$_1$-C$_4$)-alkyl, or
(c) (C$_3$-C$_7$)-cycloalkyl, which can be substituted or unsubstituted with a substitutent selected from the group consisting of: (C$_1$-C$_4$)-alkyl, (C$_1$-C$_4$)-perfluoroalkyl, Cl, Br, I or F;

R$^2$ is:
(a) H,
(b) (C$_1$-C$_6$)-alkyl,
(c) —CH$_2$—O—C(O)CH$_3$,
(d) benzyl, or
(e) phenyl;

—Y$^1$—Y$^2$—Y$^3$—Y$^4$— is:
(a) —N—CR$^{11}$—CR$^{11}$=CR$^{11}$—,
(b) —CR$^{11}$=N—CR$^{11}$=CR$^{11}$—,
(c) —CR$^{11}$=CR$^{11}$—N=CR$^{11}$—, or
(d) —CR$^{11}$=CR$^{11}$—CR$^{11}$=N—,
wherein a represents a double bond in each of the above definitions [(a) thru (d)];

R$^9$ and R$^{10}$ are independently:
(a) H, or
(b) (C$_1$-C$_4$)-alkyl;

R$^{11}$ is:
(a) H,
(b) Cl, Br, I, F,
(c) NO$_2$,
(d) NH$_2$,
(e) (C$_1$-C$_4$)-alkylamino,
(f) di-(C$_1$-C$_4$-alkyl)amino
(g) SO$_2$NHR$^2$,
(h) CF$_3$,
(i) (C$_1$-C$_4$)-alkyl,
(j) (C$_1$-C$_4$)-alkoxy, or
(k) when two R$^{11}$ substituents are bonded to adjacent carbon atoms, they can be joined to form an aryl ring;

R$^{12}$ is:
(a) H,
(b) (C$_1$-C$_4$)-alkyl, or
(c) phenyl or —CH$_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl], $N[(C_1-C_4)$-alkyl]$_2$, $NH_2$ or $CO_2R^2$;

Z is:
(a) $-CO_2R^2$,
(b) $-CN$,
(c) $-SO_2NH$-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: $-OH$, $-SH$, $-(C_1-C_4)$-alkyl, $-(C_1-C_4)$-alkoxy, $-CF_3$, Cl, Br, F, I, $-NO_2$, $-CO_2H$, $-CO_2-(C_1-C_4)$-alkyl, $-NH_2$, $NH[(C_1-C_4)$-alkyl] or $-N[(C_1-C_4)$-alkyl]$_2$,
(d) $-CH_2SO_2NH$-heteroaryl,
(e) $-SO_2NHC(O)R^{14}$,
(f) $-C(O)NHSO_2R^{14}$,
(g) $-NHSO_2R^{14}$, or
(h) $-1H$-tetrazol-5-yl;

$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, $-OH$, $-SH$, $(C_1-C_4)$-alkyl, $(C_1-C_4)$-alkoxy, $(C_1-C_4)$-alkylthio, $-CF_3$, Cl, Br, F, I, $-NO_2$, $-CO_2H$, $CO_2-(C_1-C_4)$-alkyl, $-NH_2$, $-N[(C_1-C_4)$-alkyl]$_2$, $-NH[(C_1-C_4)$-alkyl], $-PO_3H$, $PO(OH)(C_1-C_4)$-alkyoxy, or
(e) $(C_1-C_4)$-perfluoroalkyl; and $R^{17}$ is:
(a) H,
(b) F,
(c) $(C_1-C_4)$-alkyl,
(d) $(C_1-C_4)$-perfluoroalkyl,
(e) $-S-(C_1-C_3)$-alkyl, or
(f) $-O-(C_1-C_4)$-alkyl; and $R^{18}$ is:
(a) H,
(b) F,
(c) $(C_1-C_4)$-alkyl,
(d) $(C_1-C_4)$-perfluoroalkyl,
(e) phenyl or $-(C_1-C_4)$-alkyl-phenyl, wherein phenyl can be unsubstituted or substituted with one or two substituents selected from the group consisting of:
 (i) Br, Cl, I, F,
 (ii) $(C_1-C_4)$-alkyl,
 (iii) $(C_1-C_4)$-alkoxy,
 (iv) $CF_3$,
 (v) $(C_1-C_4)$-alkylthio,
 (vi) $CO_2H$, or
 (vii) $CO_2-(C_1-C_4)$-alkyl;
(f) heteroaryl,
(g) tetrazol-5-yl, or
(h) $CO_2R^2$.

5. The compound of claim 1 of structural formula

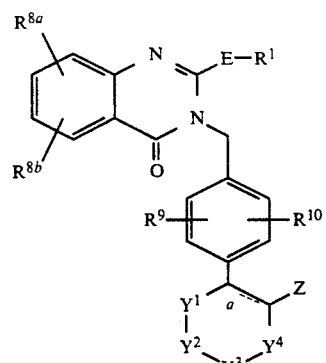

or a pharmaceutically acceptable salt thereof.

6. The compound of claim 1 of structural formula

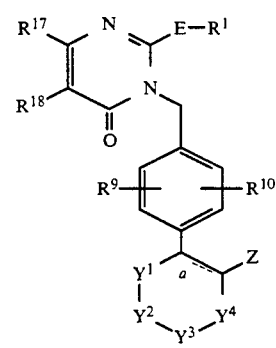

or a pharmaceutically acceptable salt thereof.

7. The compound of claim 1 of structural formula

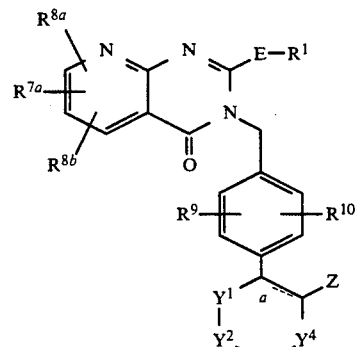

or a pharmaceutically acceptable salt thereof.

8. The compound of claim 1 of structural formula or a pharmaceutically acceptable salt thereof.

9. A compound of structural formula wherein:

R¹ is:
- (a) $(C_1-C_6)$-alkyl $(C_2-C_6)$-alkenyl or $(C_2-C_6)$-alkynyl each of which is unsubstituted or substituted with a substituent selected from the group consisting of:
  - i) $(C_1-C_4)$-alkylthio,
  - ii) $(C_1-C_4)$-alkoxy,
  - iii) $CF_3$,
  - iv) $CF_2CF_3$, or
  - v) $(C_3-C_5)$-cycloalkyl,
- (b) perfluoro-$(C_1-C_4)$-alkyl, or
- (c) $(C_3-C_7)$-cycloalkyl, which can be substituted or unsubstituted with a substituent selected from the group consisting of: $(C_1-C_4)$-alkyl, $(C_1-C_4)$-perfluoroalkyl, Cl, Br, I or F;

R² is:
- (a) H,
- (b) $(C_1-C_6)$-alkyl,
- (c) —CH₂—O—C(O)CH₃,
- (d) benzyl, or
- (e) phenyl;

R$^{8b}$ is:
- (a) H,
- (b) aryl-$(C_1-C_4)$-alkyl,
- (c) heteroaryl-$(C_1-C_4)$-alkyl,
- (d) $(C_1-C_6)$-alkyl, unsubstituted or substituted with a substituent selected from the group consisting of: —CON(R²)₂, -heteroaryl, —S(O)$_n$—R²¹, -tetrazol-5-yl, —CONHSO₂R²¹, —SO₂NH-heteroaryl, —SO₂NHCOR²¹, —PO(OR²)₂, —PO(OR²)₂, —SO₂NH—CN, —NR²COOR²¹, —OH, —NH₂, guanidino, $(C_1-C_4)$-alkoxy, $(C_1-C_4)$-alkylthio, $(C_1-C_4)$-alkylamino, $(C_1-C_4)$-dialkylamino, —COOR², —CONHR², —O—COR², or aryl,
- (e) —CO-aryl,
- (f) $(C_3-C_7)$-cycloalkyl,
- (g) Cl, Br, I, F,
- (h) —OH,
- (i) —OR²¹,
- (j) —SH,
- (k) —S(O)$_n$—$(C_1-C_4)$-alkyl,
- (l) —COR²,
- (m) —CO₂H,
- (n) —CO₂—$(C_1-C_4)$-alkyl,
- (o) —SO₃H,
- (p) —NR²R²¹,
- (q) —NR²COR²¹,
- (r) —NR²COOR²¹,
- (s) —SO₂NR²,
- (t) —SO₂NR²R²,
- (u) —NO₂,
- (v) —NHSO₂CF₃,
- (w) —CONR²R²,
- (x) —$(C_1-C_4)$-perfluoroalkyl,
- (y) —COOR²,
- (z) —SO₃H,
- (aa) —N(R²)SO₂R²¹,
- (bb) —NR²CONR²R²¹,
- (cc) —OC(=O)NR²¹R²,
- (dd) -aryl,
- (ee) —NHSO₂CF₃,
- (ff) —SO₂NH-heteroaryl,
- (gg) —SO₂NHCOR²¹,
- (hh) —CONHSO₂R²¹,
- (ii) —PO(OR²)₂,
- (jj) -tetrazol-5-yl,
- (kk) —CONH(tetrazol-5-yl),
- (ll) —SO₂NHCN, or
- (mm) -heteroaryl;

—Y¹—Y²—Y³—Y⁴— is:
- (a) —N—CR¹¹—CR¹¹=CR¹¹—,
- (b) —CR¹¹=N—CR¹¹=CR¹¹—,
- (c) —CR¹¹=CR¹¹—N=CR¹¹—, or
- (d) —CR¹¹=CR¹¹—CR¹¹=N—, wherein a represents a double bond in each of the above definitions [(a) thru (d)];

R⁹ and R¹⁰ are independently:
- (a) H, or
- (b) $(C_1-C_4)$-alkyl;

R¹¹ is:
- (a) H,
- (b) Cl, Br, I, F,
- (c) NO₂,
- (d) NH₂,
- (e) $(C_1-C_4)$-alkylamino,
- (f) di-$(C_1-C_4$-alkyl)amino
- (g) SO₂NHR²,
- (h) CF₃,
- (i) $(C_1-C_4)$-alkyl,
- (j) $(C_1-C_4)$-alkoxy, or
- (k) when two R¹¹ substituents are bonded to adjacent carbon atoms, they can be joined to form an aryl ring;

R¹² is:
- (a) H,
- (b) $(C_1-C_4)$-alkyl, or
- (c) phenyl or —CH₂-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)\text{-alkyl}]$, $N[(C_1-C_4)\text{-alkyl}]_2$, $NH_2$ or $CO_2R^2$;

Z is:
- (a) $-CO_2R^2$,
- (b) $-CN$,
- (c) $-SO_2NH$-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: $-OH$, $-SH$, $-(C_1-C_4)$-alkyl, $-(C_1-C_4)$-alkoxy, $-CF_3$, Cl, Br, F, I, $-NO_2$, $-CO_2H$, $-CO_2-(C_1-C_4)$-alkyl, $-NH_2$, $NH[(C_1-C_4)\text{-alkyl}]$ or $-N[(C_1-C_4)\text{-alkyl}]_2$,
- (d) $-CH_2SO_2NH$-heteroaryl,
- (e) $-SO_2NHC(O)R^{14}$,
- (f) $-C(O)NHSO_2R^{14}$,
- (g) $-NHSO_2R^{14}$, or
- (h) $-1H$-tetrazol-5-yl;

$R^{14}$ is
- (a) aryl,
- (b) heteroaryl,
- (c) $(C_3-C_7)$-cycloalkyl,
- (d) $(C_1-C_4)$-alkyl, unsubstituted or substituted with a substituent selected from the group consisting of: aryl, heteroaryl, $-OH$, $-SH$, $(C_1-C_4)$-alkyl, $(C_1-C_4)$-alkoxy, $(C_1-C_4)$-alkylthio, $-CF_3$, Cl, Br, F, I, $-NO_2$, $-CO_2H$, $CO_2-(C_1-C_4)$-alkyl, $-NH_2$, $-N[(C_1-C_4)\text{-alkyl}]_2$, $-NH[(C_1-C_4)\text{-alkyl}]$, $-PO_3H$, $PO(OH)(C_1-C_4)$-alkyoxy, or
- (e) $(C_1-C_4)$-perfluoroalkyl; and $R^{21}$ is:
- (a) aryl, or
- (b) $(C_1-C_4)$-alkyl which is unsubstituted or substituted with:
  - i) $NH_2$,
  - ii) $NH[(C_1-C_4)\text{-alkyl}]$,
  - iii) $N[(C_1-C_4)\text{-alkyl}]_2$,
  - iv) $CO_2H$,
  - v) $CO_2(C_1-C_4)$-alkyl,
  - vi) OH,
  - vii) $SO_3H$, or
  - viii) $SO_2NH_2$;

or a pharmaceutically acceptable salts thereof.

10. A pharmaceutical composition useful in the treatment of hypertension which comprises a pharmaceutically acceptable carrier and a therapeutically effective amount of a compound of claim 1.

11. A method of treating hypertension which comprises administering to a patient in need of such treatment a therapeutically effective amount of a compound of claim 1.

12. A method of treating ocular hypertension comprising topical ocular administration to a patient in need of such treatment of an effective ocular antihypertensive amount of a compound of claim 1.

13. A method of treating cognitive dysfunction, anxiety, or depression comprising administering to a patient in need of such treatment, a therapeutically effective amount of a compound of claim 1.

* * * * *